(12) United States Patent
Weng et al.

(10) Patent No.: US 8,447,526 B2
(45) Date of Patent: May 21, 2013

(54) METHODS AND COMPUTER SYSTEMS FOR ANALYZING HIGH-THROUGHPUT ASSAYS

(75) Inventors: Lee Weng, Bellevue, WA (US);
Hongyue Dai, Kenmore, WA (US);
Steven R. Bartz, Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 1554 days.

(21) Appl. No.: 11/440,195

(22) Filed: May 23, 2006

(65) Prior Publication Data

US 2007/0015135 A1    Jan. 18, 2007

Related U.S. Application Data

(60) Provisional application No. 60/684,128, filed on May 23, 2005.

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC ............... 702/19; 702/22; 703/11; 703/12

(58) Field of Classification Search
None
See application file for complete search history.

(56) References Cited

U.S. PATENT DOCUMENTS

| | | | |
|---|---|---|---|
| 5,569,588 A | 10/1996 | Ashby et al. | |
| 6,004,941 A | 12/1999 | Bujard et al. | |
| 6,218,122 B1 | 4/2001 | Friend et al. | |
| 6,691,042 B2 | 2/2004 | Weng et al. | |
| 2003/0226098 A1 | 12/2003 | Weng | |
| 2004/0143399 A1* | 7/2004 | Weng | 702/19 |
| 2005/0181385 A1* | 8/2005 | Linsley et al. | 435/6 |

FOREIGN PATENT DOCUMENTS

| | | |
|---|---|---|
| WO | WO 98/38329 | 9/1998 |
| WO | WO 99/58708 | 11/1999 |
| WO | WO 99/59037 | 11/1999 |
| WO | WO 99/66067 | 12/1999 |
| WO | WO 00/24936 | 5/2000 |
| WO | WO 00/39336 | 7/2000 |
| WO | WO 2005/018534 | 3/2005 |

OTHER PUBLICATIONS

Aebersold et al., "Quantitative analysis of complex protein mixtures using isotope-coded affinity tags," 1999, Nat. Biotechnol. 10:994-999.

Alley et al., "Feasibility of Drug Screening with Panels of Human Tumor Cell Lines Using a Microculture Tetrazolium Assay," 1988, Cancer Res. 48: 589-601.

(Continued)

*Primary Examiner* — Larry D Riggs, II
(74) *Attorney, Agent, or Firm* — Klarquist Sparkman, LLP

(57) ABSTRACT

The present invention provides methods and computer programs for detecting variations in measurements of a biological variable, e.g., variations in cell viability, under different conditions, e.g., with or without treatment of a drug, under the treatments of different drugs, or under different environmental conditions. The methods and programs of the invention determine a metric of difference between measurements under different condition, and make use of predetermined errors of the measurements, e.g., errors determined from an error model, to estimate the errors in the metric of difference. Such an approach provides a more accurate estimate of the errors of measurements, which, in turn, provides a more accurate estimate of the error of the difference metric.

19 Claims, 16 Drawing Sheets

OTHER PUBLICATIONS

Bailey et al., "*Applications of Transfected Cell Microarrays in High Through-Out Drug Discovery*," 2002, DDT vol. 7, No. 18 (supplement):1-6.

Beaumont et al., "*Integrated Technology Platform for Fluorence 2-D Difference Gel Electrophoresis*," 2001, Life Science News 7, pp. 3-5, Amersham Pharmacia Biotech.

Blanchard et al., "*Sequence to Array: Probing the Genome's Secret*," 1996, Nature Biotechnology 14:1649.

Boden et al., "*Promoter choice affects the potency of HIV-1 specific RNA interference*," 2003, Nucleic Acids Res. 31:5033-5038.

Brummelkamp et al., "*A System for Stable Expression of Short Interfering RNAs in Mammalian Cells*," 2002, Science 296:550-553.

Carmichael et al., "*Evaluation of a Tetrazolium-based Semiautomated Colorimetric Assay: Assessment of Chemosensitivity Testing*," 1987, Cancer Res. 47:936-942.

de Wildt et al., "*Antibody arrays for high-throughput screening of antibody-antigen interactions*," 2000, Nat. Biotechnol. 18:989-994.

Farkas et al., "*Multimode Light Microscopy and the Dynamics of Molecules, Cells, and Tissues*," 1993, Ann. Rev. Physiol. 55:785-817.

Ferrari et al., "*MTT colorimetric assay for testing macrophage cytotoxic activity in vitro*," 1990, J. Immunol. Methods 131: 165-172.

Gerlier et al., "*Use of MTT colorimetric assay to measure cell activation*," 1986, J. Immunol. Methods 65:55-63.

Giuliano et al., In Optical Microscopy for Biology. B. Herman and K. Jacobson (eds.), Wiley-Liss, New York, 1990, pp. 543-557.

Giuliano et al., "*Fluorescent Protein Biosensors: Measurement of Molecular Dynamics in Living Cells*," 1995, Ann. Rev. Biophys. Biomol. Struct. 24:405-434.

Giuliano et al., "*Measurement and Manipulation of Cytoskelal Dynamics in Living Cells*," 1995, Curr. Op. Cell Biol. 7:4-12.

Goffeau et al., "Life with 6000 Genes", 1996, *Science* 274:546-567.

Gossen et al, "*Transcriptional Activation by Tetracyclines in Mammalian Cells*," 1995, Science 268:1766-1769.

Hahn et al., "*Patterns of Elevated Free Calcium and Calmulin Activation in Living Cells*," 1992, Nature 359:736-738.

Hames et al., "*Gel Electrophoresis of Proteins: A Practical Approach*," IRL Press, New York, 1990, pp. 217-270.

Kawasaki et al., "*Short hairpin type of dsRNAs that are controlled by tRNAVal promoter significantly induce RNAi-mediated gene silencing in the cytoplasm of human cells*," 2003, Nucleic Acids Res. 31:700-707.

Kwak et al., "*RNA Interference With Small Hairpin RNAs Transcribed From a Human U6 Promoter-Driven DNA Vector*," 2003, J. Pharmacol. Sci. 93:214-217.

Lander, "The New Genomics: Global Views of Biology 1996," *Science* 274:536-539.

Li et al., "*tsg101: A Novel Tumor Susceptibility Gene Isolated by Controlled Homozygous Functional Knockout of Allelic Loci in Mammalian Cells*," 1996, Cell 85:319-329.

Lockhart et al., "*Expression Monitoring by Hybridization to High-Density Oligonucleotide Arrays*," 1996, Nat. Biotechnol. 14:1675-1680.

Lucas et al, "*Hormone Response Domains in Gene Transcription*," 1992, Annu. Rev. Biochem. 61:1131.

MacBeath et al., "*Printing Proteins as Microarrays for High-Throughput Function Determination*," 2000, Science 289:1760-63.

Miyagishi et al., "*U6 Promoter-Driven siRNAs with Four Uridine 3' Overhangs Efficiently Suppressed Targeted Gene Expression in Mammalian Cells*," 2002, Nat. Biotechnol., 20:497-500.

Mosmann, "*Rapid Colorimetric Assay for Cellular Growth and Survival: Application to Proliferation and Cytotoxicity Assays*," 1983, J. Immunological Methods 65:55-63.

Ohno et al., "*Rapid colorimetric assay for the quantification of leukemia inhibitory factor (LIF) and interleukin-6 (IL-6)*," 1991, J. Immunol. Methods 145:199-203.

D. Holder, et al., "*Quantitation of Gene Expression for High-Density Oligonucleotide Arrays: A SAFER Approach*", [online], Nov. 19, 2001 [retrieved on Jun. 8, 2009]. Retrieved from the Internet:<URL: http://oz.berkeley.edu/users/terry/zarray/Affy/GL_WorkshoplHolder.ppt>.

Paddison et al., "Short hairpin RNAs (shRNAs) induce sequence-specific silencing in mammalian cells," 2002, *Genes Dev.* 16:948-958.

Page et al., "*A New Fluorometric Assay for Cytotoxicity Measurements In Vitro*," 1993, Int. J. Oncol. 3:473-476.

Paul et al., "*Effective Expression of Small Interfering RNA in Human Cells*," 2002, Nat. Biotechnol. 20:505-508.

Pollock et al., "*Delivery of a stringent dimerizer-regulated gene expression system in a single retroviral vector*," 2000, Proc. Natl. Acad. Sci. USA 97:13221-13226.

Roberts et al, "*Signaling and Circuitry of Multiple MAPK Pathways Revealed by a Matrix of Global Gene Expression Profiles*," 2000, Science, 287:873-880.

Rocke et al., "*A Model for Measurement Error for Gene Expression Arrays*," 2001, J. Computational Biology 8:557-569.

Saez et al., "*Identification of ligands and coligands for the ecdysone-regulated gene switch*," 2000, Proc. Natl. Acad. Sci. USA 97:14512-14517.

Sagliocco et al., "Identification of Proteins of the Yeast Protein Map using Genetically Manipulated Strains and Peptide-Mass k+ingerprinting," 1996, *Yeast* 12:1519-1533.

Schena et al., "*Quantitative Monitoring of Gene Expression Patterns with a Complementary DNA Microarray*," 1995, Science 270:467-470.

Shevchenko et al., "Linking genome and proteome by mass spectrometry: Large-scale identification of yeast proteins from two dimensional gels," 1996, *Proc. Natl. Acad. Sci. USA* 93:1440-1445.

Sui et al., "*A DNA vector-based RNAi technology to suppress gene expression in mammalian cells*," 2002, Proc. Natl. Acad. Sci. 99:5515-5520.

van de Loosdrechet, et al., "*A tetrazolium-based colorimetric MTT assay to quantitate human monocyte mediated cytotoxicity against leukemic cells from cell lines and patients with acute myeloid leukemia*," 1994, J. Immunol. Methods 174:311-320.

Waggoner et al., "*Multiparameter fluorescence imaging microscopy: reagents and instruments*," 1996, Hum. Pathol. 27:494-502.

Yu et al., "*RNA interference by expression of short-interfering RNAs and hairpin RNAs in mammalian cells*," 2002, Proc. Natl. Acad. Sci. 99:6047-6052.

Zhu et al., "*Global Analysis of Protein Activities Using Proteome Chips*," 2001, Science 293:2101-2105.

Ziauddin et al., "*Microarrays of cells expressing defined cDNAs*," 2001, Nature 411:107-110.

\* cited by examiner

METHODS AND COMPUTER SYSTEMS FOR ANALYZING HIGH-THROUGHPUT ASSAYS

This application claims the benefit under 35 U.S.C. §119 (e) of U.S. Provisional Patent Application No. 60/684,128, filed on May 23, 2005, which is incorporated by reference herein in its entirety.

1. FIELD OF THE INVENTION

The present invention relates to methods and computer systems for analyzing high-throughput assays, e.g., cell-based drug screening assays. The invention also relates to methods and computer systems for quantitative comparison of data generated in independently performed high-throughput assays.

2. BACKGROUND OF THE INVENTION

Cell-based assays have become indispensable tools in drug discovery and development and biological investigations. Cell-based assays are used for monitoring cell health and cell death under various conditions. For example, cell-based assays allow quantitation of cell viability and cell proliferation. Cell-based assays are also used for monitoring molecular processes in cells, such as activation of particular signaling pathways, receptor binding, ion concentrations, membrane potential, specific translocations, enzyme activities, gene expression, as well as the presence, amounts and patterns of cellular molecules, e.g., metabolites, proteins, lipids, carbohydrates, and nucleic acid sequences. Thus, cell-based assays allow investigation of molecular mechanisms of diseases and drug effects. Cell-based assays can be performed with either living cells or fixed-cell preparations, and either on a single cell basis or on a cell population basis. In drug development, cell-based assays are now used in almost all phases from primary screening to in vitro toxicity evaluation.

Cell-based assays are commensurate with high-throughput screen (HTS) and high-content screen (HCS). This is especially important in drug discovery. High-throughput screens are often carried out using a parallel assay format in which multiple samples are screened concurrently. For example, high throughput screens of a large number of different chemical compounds and/or biological agents are often carried out using arrays of wells, e.g., in standard microtiter plates with 96, 384 or 1536 wells. The signal measured from each well, e.g., fluorescence emission or optical density, integrates the signal from all the material in the well to give an overall population average of all the molecules in the well. Large scale cell-based screens of interactions between drugs and an siRNA library was disclosed in U.S. Patent Application Publication No. 2005-0181385, published on Aug. 18, 2005.

High-content screens allow monitoring multiple molecules and/or processes. For example, high-content screens can be performed with multiple fluorescence labels of different colors (Giuliano et al., 1995, Curr. Op. Cell Biol. 7:4; Giuliano et al., 1995, Ann. Rev. Biophys. Biomol. Struct. 24:405). In a high-content screen, both spatial and temporal dynamics of various cellular processes can be monitored (Farkas et al., 1993, Ann. Rev. Physiol. 55:785; Giuliano et al., 1990, In Optical Microscopy for Biology. B. Herman and K. Jacobson (eds.), pp. 543-557, Wiley-Liss, New York; Hahn et al., 1992, Nature 359:736; Waggoner et al., 1996, Hum. Pathol. 27:494). Single cell measurements can also be performed. Each cell can be treated as a "well" that has spatial and temporal information on the activities of the labeled constituents.

In addition to microtiter plate and flow cytometry, cell-based assays can also be performed using cell microarrays (Ziauddin et al., Nature 411:107-110; Bailey et al., DDT 7, No. 18 (supplement): 1-6). Cell microarrays can be generated by printing cDNA-containing plasmids on a surface. The printed arrays are then exposed to a lipid transfection reagent to form lipid-DNA complexes on the surface. Cells are then added to the surface. Clusters of cells transfected by cDNA contained in a plasmid printed on the surface are generated at the location of the printed plasmid. Such cell microarrays can contain as high as 6,000 to 10,000 spots per slide. Each spot contains a cluster of about 100 transfected cells.

High-throughput DNA array technologies have made it possible to monitor the expression level of a large number of genetic transcripts at any one time (see, e.g., Schena et al., 1995, Science 270:467-470; Lockhart et al., 1996, Nature Biotechnology 14:1675-1680; Blanchard et al., 1996, Nature Biotechnology 14:1649; Ashby et al., U.S. Pat. No. 5,569,588, issued Oct. 29, 1996). By simultaneously monitoring tens of thousands of genes, DNA array technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., Stoughton et al., International Publication No. WO 00/39336, published Jul. 6, 2000; Friend et al., International Publication No. WO 00/24936, published May 4, 2000). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Stoughton, International Publication No. WO 99/66067 (published Dec. 23, 1999); Stoughton and Friend, International Publication No. WO 99/58708 (published Nov. 18, 1999); Friend and Stoughton, International Publication No. WO 99/59037 (published Nov. 18, 1999); Friend et al., U.S. Pat. No. 6,218,122.

Protein microarrays are used to monitor the genome-wide protein expression in cells (i.e., the "proteome," Goffeau et al., 1996, Science 274:546-567; Aebersold et al., 1999, Nature Biotechnology 10:994-999). Protein microarrays contain binding sites comprise immobilized, preferably monoclonal, antibodies specific to a plurality of protein species encoded by the cell genome (see, e.g., Zhu et al., 2001, Science 293:2101-2105; MacBeath et al., 2000, Science 289:1760-63; de Wildt et al., 2000, Nature Biotechnology 18:989-994). Protein expression in a cell can also be separated and measured by two-dimensional gel electrophoresis techniques. Two-dimensional gel electrophoresis is well-known in the art and typically involves iso-electric focusing along a first dimension followed by SDS-PAGE electrophoresis along a second dimension. See, e.g., Hames et al., 1990, Gel Electrophoresis of Proteins: A Practical Approach, IRL Press, New York; Shevchenko et al., 1996, Proc. Natl. Acad. Sci. USA 93:1440-1445; Sagliocco et al., 1996, Yeast 12:1519-1533; Lander, 1996, Science 274:536-539; and Beaumont et al., Life Science News 7, 2001, Amersham Pharmacia Biotech. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

In these screens, it is often desirable to compare a measurement of a variable in a sample of interest with that in a reference sample to determine the change in the measurement relative to the reference sample (see, e.g., U.S. Patent Application Publication No. 2005-0181385, published on Aug. 18, 2005). For example, in a cell-based drug screen assay, it is often desirable to determine the difference in growth rate of cells under the treatment of a drug versus that of cells not under the treatment. Thus, in such screens, measurements of one or more reference samples are often made concurrently with the treated sample. A metric of the difference between the measurement of the test sample and the reference sample is used as a measure of the change. The measured changes under different conditions are then compared. In order to reliably compare changes, the errors in the measured changes are needed. Because the reference contains errors, the error of the metric must include reference errors. However, due to low number of replicate reference measurements, error estimation for the reference measurements using the traditional approach is often not accurate. There is therefore a need for a more accurate method of estimating reference errors.

High content, high throughput and miniature assays are most easily achieved using fluorescence detection. For example, fluorescence dye-based assays for cell viability and cytotoxicity are reliable and easy to perform. Multiple samples may be monitored concurrently. Fluorescence-based assays require low volumes of reagents and test compounds. Fluorescence-based assays permit monitoring multiple variables by using fluorescence labels of different emission wavelengths. For example, simultaneous two-color measurements of numbers of live and dead cells permit assaying the viability status of mixed-cell populations.

The measured fluorescence intensity for each probe site, be it a single cell or a population of cells, comes from various sources, e.g., signal from the intended species, noise due to background, etc. The average intensity within a probe site can be measured by the median image value on the site. This intensity serves as a measure of the total photons emitted from the sample for the measured wavelength. The median is used as the average to mitigate the effect of outlying pixel values created by noise. See, e.g., U.S. Patent Application Publication No. 2003-0226098, published on Dec. 4, 2003

Measurement error in a measured signal comes from various sources, including those that fall into the following three categories: additive error, multiplicative error, and Poisson error. The signal magnitude-independent or intensity-independent additive error includes errors resulted from, e.g., background fluctuation, or site-to-site variations (e.g., well-to-well variations in microtiter plate experiment and spot-to-spot variations in a microarray experiment) in signal intensity among negative control sites, etc. The signal magnitude-dependent or intensity-dependent multiplicative error, which is proportional to the signal intensity, includes errors resulted from, e.g., the scatter observed for ratios that should be unity. The multiplicative error is also termed fractional error. The third type of error is a result of variation in number of available binding sites in a spot. This type of error depends on the square-root of the signal magnitude, e.g., measured intensity. It is also called the Poisson error, because it is believed that the number of binding sites on a microarray spot follows a Poisson distribution, and has a variance which is proportional to the average number of binding sites. Errors in measured data can be described by error models (see, e.g., Supplementary material to Roberts et al., 2000, Science, 287:873-880; U.S. Patent Application Publication No. 2003-0226098, published on Dec. 4, 2003; and Rocke et al., 2001, J. Computational Biology 8:557-569). U.S. Patent Application Publication No. 2003-0226098, published on Dec. 4, 2003, discloses methods for analyzing measurement errors in measured signals obtained in an experiment, e.g., measured intensity signals obtained in a microarray gene expression experiment. The application discloses a method for transforming measured signals into a domain in which the measurement errors in the transformed signals are normalized by errors as determined from an error model. The methods are particularly useful for analyzing measurement errors in signals in which at least portion of the error is dependent on the magnitudes of the signals. Such transformed signals permit analysis of data using traditional statistical methods, e.g., ANOVA and regression analysis. Magnitude-independent errors can also be used for comparing level of measurement errors in signals of different magnitudes.

U.S. Pat. No. 6,691,042 discloses methods for generating differential profiles A vs. B, i.e., differential profiles between samples having been subject to condition A and condition B, from data obtained in separately performed experimental measurements A vs. C and B vs. D. When C and D are the same, i.e., common, the methods involve determination of systematic measurement errors or biases between measurements carried out in different experimental reactions, i.e., cross-experiment errors or biases, using data measured for samples under the common condition and for removal or reduction of such cross-experiment errors. U.S. Pat. No. 6,691,042 also provides methods for generating differential profiles A vs. B from data obtained in separately performed single-channel measurements A and B.

U.S. Patent Application Publication No. 2004-0143399, published on Jul. 22, 2004, discloses improved ANOVA methods for analyzing measured data and transformed data. The improved ANOVA method takes two data types as its input, the measurements and a predetermined error associated with the measurements. The latter can come from a technology/platform-specific error model. Because of the additional input information, the statistical power is increased.

Discussion or citation of a reference herein shall not be construed as an admission that such reference is prior art to the present invention.

3. SUMMARY OF THE INVENTION

The invention provides a method of determining an effect of a perturbation on a biological variable in one or more cells of a cell type relative to one or more cells of said cell type under a reference condition, comprising (a) determining (i) a reference mean $\bar{y}$ of one or more reference measurements $\{y_i\}$ of said biological variable in one or more respective reference cell samples each comprising one or more cells of said cell type under said reference condition, wherein i=1, 2, . . . , $n_r$, $n_r$ being the number of reference measurements; and (ii) a reference error $\sigma_y$, wherein said reference error comprises a propagated error $\sigma_p$ and a scattered error $\sigma_s$, said propagated error being determined based on predetermined experiment errors of said reference measurements, and said scattered error being determined based on deviation of each of said reference measurements with respect to said reference mean; (b) determining a metric of difference between (iii) a measurement x of said biological variable in a cell sample comprising one or more cells of said cell type under said perturbation and (iv) said reference mean; and (c) determining an error of said metric based on a predetermined experiment error $\sigma_x$ of said measurement x and said reference error $\sigma_y$, wherein said metric and said error of said metric represent said effect.

In one embodiment, said propagated error is determined according to the equation $$\sigma_p = \frac{\sqrt{\sum_i \sigma_y^2(i)}}{n_r}$$

where $\sigma_y^2(i)$ is a predetermined experiment error of measurement $y_i$; wherein said scattered error is determined according to the equation $$\sigma_s = \underset{i \in 1, \ldots, n_r}{stdev(y_i)} / \sqrt{n_r}$$

and wherein said reference error is determined according to the equation $$\sigma_y = \frac{\sigma_p + (n_r - 1) \cdot \sigma_s}{n_r}.$$

In one embodiment, the method further comprises: prior to said step (a) a step of determining said predetermined experiment error $\sigma_y(i)$ for each said measurement $y_i$; and prior to said step (b) a step of determining said predetermined experiment error $\sigma_x$ for said measurement x.

In one embodiment, said predetermined experiment error $\sigma_x$ for said measurement x and said predetermined error $\sigma_y(i)$ for said measurement $y_i$ are determined according to an error model. In a preferred embodiment, said error model is a three-term error model according to the equations $$\sigma_x = \sqrt{\sigma_{bkg}^2 + b^2 \cdot x + a^2 \cdot x^2}$$

and $$\sigma_y(i) = \sqrt{\sigma_{bkg}^2 + b^2 \cdot y_i + a^2 \cdot y_i^2}$$

wherein a is a fractional error coefficient, b is a Poisson error coefficient, and $\sigma_{bkg}$ is a standard deviation of background noise. In another preferred embodiment, said error model is a two-term error model according to the equations $$\sigma_x = \sqrt{\sigma_{bkg}^2 + a^2 \cdot x^2}$$

and $$\sigma_y(i) = \sqrt{\sigma_{bkg}^2 + a^2 \cdot y_i^2}$$

wherein a is a fractional error coefficient and $\sigma_{bkg}$ is a standard deviation of background noise.

In one embodiment, said $\sigma_{bkg}$ is determined based on one or more measurements of said biological variable in a negative control sample, e.g., a sample that comprises no cells.

In a preferred embodiment, said metric of difference is a ratio of said measurement x and said reference mean $\bar{y}$: $x/\bar{y}$. In one embodiment, said error of said metric is determined according to the equation $$\sigma_{ratio} = \sqrt{\sigma_{Logx}^2 + \sigma_{Logy}^2} \cdot \frac{x/\bar{y}}{Log_{10}(e)}$$

where $$\sigma_{Logx} = Log_{10}(e) \cdot \frac{\sigma_x}{x}$$

and $$\sigma_{Logy} = Log_{10}(e) \cdot \frac{\sigma_y}{y}$$

In one embodiment, said measurement of said biological variable is a fluorescence intensity.

In some embodiments, said biological variable is an abundance of a protein. In other embodiments, said biological variable is an abundance of a transcript of a gene. In still other embodiments, said biological variable is a survival rate of cells as represented by the number of living cells measured after a chosen period of time after said perturbation.

In some embodiments, said reference condition is a condition free of said perturbation, and said ratio represents viability of cells of said cell type under said perturbation. In one embodiment, said reference condition is selected from the group consisting of a mock treatment of cells of said cell type, a negative control condition, and a positive control condition.

In one embodiment, said perturbation comprises subjecting cells of said cell type to one or more agents. In one embodiment, said one or more agents comprise a drug. In another embodiment, said one or more agents comprise an siRNA targeting a gene in a cell of said cell type. In another embodiment, said one or more agents comprise both a siRNA and a drug. In one embodiment that uses siRNA, said reference condition comprises subjecting cells of said cell type to an siRNA targeting luciferase.

In another aspect, the invention provides a method of comparing effects of a first perturbation on a biological variable in one or more cells of a cell type and a second perturbation on said biological variable in one or more cells of said cell type, comprising (a) determining (ai) a first metric of difference $z_1$ between a first measurement $x_1$ of said biological variable in a cell sample comprising one or more cells of said cell type under said first perturbation and one or more first reference measurements $\{y_{1,i}\}$ of said biological variable in one or more respective first reference cell samples each comprising one or more cells of said cell type under a first reference condition and (aii) an error $\sigma_1$ of said first metric, wherein i=1, 2, . . . , $n_{1r}$, $n_{1r}$ being the number of said first reference measurements, by a method comprising (a1) determining (a1i) a first reference mean $\bar{y}_1$ of said one or more first reference measurements and (a1ii) a first reference error $\sigma_{1,y}$, wherein said first reference error comprises a first propagated error $\sigma_{1,p}$ and a first scattered error $\sigma_{1,s}$, said first propagated error being determined based on predetermined experiment errors of said first reference measurements, and said first scattered error being determined based on deviations of said one or more first reference measurements with respect to said first reference mean; (a2) determining said first metric of difference $z_1$ based on said first measurement $x_1$ and said first reference mean $\bar{y}_1$; (a3) determining said error $\sigma_1$ of said first metric based on (a3i) a predetermined experiment error $\sigma_{1,x}$ for said measurement $x_1$, and (a3ii) said first reference error $\sigma_{1,y}$; (b) determining (bi) a second metric of difference $z_2$ between a second measurement $x_2$ of said biological variable in a cell sample comprising one or more cells of said cell type under said second perturbation and one or more second reference measurements $\{y_{2,j}\}$ of said biological variable in one or more respective second reference cell samples each comprising one or more cells of said cell type under a second reference condition, and (bii) an error $\sigma_2$ of said second metric, wherein $j=1, 2, \ldots, n_{2,r}$, $n_{2,r}$ being the number of said second reference measurements, by a method comprising (b1) determining (b1i) a second reference mean $\bar{y}_2$ of said one or more second reference measurements, and (b2i) a second reference error $\sigma_{2,y}$, wherein said second reference error comprises a second propagated error $\sigma_{2,p}$ and a second scattered error $\sigma_{2,s}$, said second propagated error being determined based on predetermined experiment errors of said second reference measurements, and said second scattered error being determined based on deviations of said second reference measurements with respect to said second reference mean; (b2) determining said second metric of difference $z_2$ based on said second measurement $x_2$ and said second reference mean $\bar{y}_2$; (b3) determining said error $\sigma_2$ of said second metric based on a predetermined experiment error $\sigma_{2,x}$ for said measurement $x_2$ and said second reference error $\sigma_{2,y}$; and (c) comparing $z_1$, $\sigma_1$ with $z_2$, $\sigma_2$, thereby comparing said effects of said first and second perturbation.

In one embodiment, said step (c) is carried out by a method comprising determining (c1) a parameter xdev according to the equation $$xdev = \frac{z_1 - z_2}{\sqrt{\sigma_1^2 + \sigma_2^2}},$$

and (c2) a p-value for said parameter xdev according to the equation $$p\text{-value} = 2 \cdot Erf(|xdev|)$$

wherein said xdev and p-value are measures of said comparison.

In another embodiment, said step (c) further comprises determining (c3) a log ratio according to the equation $$l\text{ratio} = \log_{10}(z_1/z_2)$$

and (c4) an error of said log ratio according to the equation $$\sigma_{lratio} = \left|\frac{lratio}{xdev}\right|.$$

In one embodiment, said first and second propagated errors are determined according to equations $$\sigma_{1,p} = \frac{\sqrt{\sum_i \sigma_{1,y}^2(i)}}{n_{1,r}} \text{ and } \sigma_{2,p} = \frac{\sqrt{\sum_j \sigma_{2,y}^2(j)}}{n_{2,r}}, \text{ respectively,}$$

where $\sigma_{1,y}^2(i)$ and $\sigma_{2,y}^2(j)$ are predetermined experiment errors of measurement $y_{1,i}$ and $y_{1,j}$, respectively, wherein said first and second scattered errors are determined according to equations $$\sigma_{1,s} = \underset{i \in 1,2,\ldots,n_{1,r}}{stdev(y_{1,i})} \Big/ \sqrt{n_{1,r}} \text{ and } \sigma_{2,s} = \underset{j \in 1,2,\ldots,n_{2,r}}{stdev(y_{2,j})} \Big/ \sqrt{n_{2,r}}, \text{ respectively,}$$

and wherein said first and second reference errors are determined according to equation $$\sigma_{1,y} = \frac{\sigma_{1,p} + (n_{1,r}-1) \cdot \sigma_{1,s}}{n_{1,r}} \text{ and } \sigma_{2,y} = \frac{\sigma_{2,p} + (n_{2,r}-1) \cdot \sigma_{2,s}}{n_{2,r}}, \text{ respectively.}$$

In one embodiment, the method further comprises (i) prior to said step (a1) a step of determining said predetermined experiment error $\sigma_{1,y}(i)$ for each said measurement $y_{1,i}$ and prior to said step (a3) a step of determining said predetermined experiment error $\sigma_{1,x}$ for said measurement $x_1$, and (ii) prior to said step (b1) a step of determining said predetermined experiment error $\sigma_{2,y}(j)$ for each said measurement $y_{2,j}$ and prior to said step (b3) a step of determining said predetermined experiment error $\sigma_{2,x}$ for said measurement $x_2$.

In one embodiment, said predetermined experiment errors of said measurements $x_1$ and $x_2$, and said measurements $\{y_{1,i}\}$ and $\{y_{2,j}\}$ are determined according to an error model. In a preferred embodiment, said error model is a three-term error model according to equations $$\sigma_{1,x} = \sqrt{\sigma_{bkg}^2 + b^2 \cdot x_1 + a^2 \cdot x_1^2} \text{ and } \sigma_{2,x} = \sqrt{\sigma_{bkg}^2 + b^2 \cdot x_2 + a^2 \cdot x_2^2}$$

and equations $$\sigma_{1,y}(i) = \sqrt{\sigma_{bkg}^2 + b^2 \cdot y_{1,i} + a^2 \cdot y_{1,i}^2} \text{ and } \sigma_{2,y}(j) = \sqrt{\sigma_{bkg}^2 + b^2 \cdot y_{2,j} + a^2 \cdot y_{2,j}^2}$$

wherein a is a fractional error coefficient, b is a Poisson error coefficient, and $\sigma_{bkg}$ is a standard deviation of background noise. In another preferred embodiment, said error model is a two-term error model according to equations $$\sigma_{1,x} = \sqrt{\sigma_{bkg}^2 + a^2 \cdot x_1^2} \text{ and } \sigma_{2,x} = \sqrt{\sigma_{bkg}^2 + a^2 \cdot x_2^2}$$

and equations $$\sigma_{1,y}(i) = \sqrt{\sigma_{bkg}^2 + a^2 \cdot y_{1,i}^2} \text{ and } \sigma_{2,y}(j) = \sqrt{\sigma_{bkg}^2 + a^2 \cdot y_{2,j}^2}$$

wherein a is a fractional error coefficient, and $\sigma_{bkg}$ is a standard deviation of background noise.

In one embodiment, said $\sigma_{bkg}$ is determined based on one or more measurements of said biological variable in a negative control sample, e.g., a sample that comprises no cells.

In one embodiment, said first metric of difference is a ratio of said first measurement $x_1$ and said first reference mean $\bar{y}_1$: $z_1 = x_1/\bar{y}_1$ and said second metric of difference is a ratio of said second measurement $x_2$ and said second reference mean $\bar{y}_2$: $z_2 = x_2/\bar{y}_2$.

In one embodiment, said first and second errors of said metric is determined according to equations $$\sigma_{1,ratio} = \sqrt{\sigma_{1,Logx}^2 + \sigma_{1,Logy}^2} \cdot \frac{z_1}{\text{Log}_{10}(e)} \text{ and }$$

$$\sigma_{2,ratio} = \sqrt{\sigma_{2,Logx}^2 + \sigma_{2,Logy}^2} \cdot \frac{z_2}{\text{Log}_{10}(e)}$$

respectively, where $$\sigma_{1,Logx} = \text{Log}_{10}(e) \cdot \frac{\sigma_{1,x}}{x_1} \text{ and } \sigma_{2,Logx} = \text{Log}_{10}(e) \cdot \frac{\sigma_{2,x}}{x_2}$$

and $$\sigma_{1,Logy} = \text{Log}_{10}(e) \cdot \frac{\sigma_{1,y}}{\bar{y}_1} \text{ and } \sigma_{2,Logy} = \text{Log}_{10}(e) \cdot \frac{\sigma_{2,y}}{\bar{y}_2}$$

In one embodiment, said measurement of said biological variable is a fluorescence intensity.

In some embodiments, said biological variable is an abundance of a protein. In other embodiments, said biological variable is an abundance of a transcript of a gene. In still other embodiments, said biological variable is a survival rate of cells as represented by the number of living cells measured after a chosen period of time after said first and second perturbation.

In one embodiment, said first and second reference conditions are conditions free from said first and second perturbations, and each said ratio represents viability of cells of said cell type under the respective perturbation. In one embodiment, said first perturbation comprises subjecting cells of said cell type to one or more first agents and said second perturbation comprises subjecting cells of said cell type to one or more second agents. In a specific embodiment, said first and second reference conditions are the same condition selected from the group consisting of a mock treatment of cells of said cell type, a negative control condition, and a positive control condition.

In one embodiment, said one or more first agents comprise a first drug and said one or more second agents comprise a second drug. In a specific embodiment, said first drug and said second drug are the same drug of different doses.

In another embodiment, said one or more first agents comprise a first siRNA targeting a first gene of said cell type and said one or more second agents comprise a second siRNA targeting a second gene, different from said first gene, of said cell type. In one embodiment, said first and second reference conditions are the same condition that comprises subjecting cells of said cell type to an siRNA targeting luciferase. In another embodiment, said one or more first agents comprise both a first drug and said first siRNA and said one or more second agents comprise both said second siRNA and a second drug.

In one embodiment, said first and second reference conditions are the same. In another embodiment, said first and second reference measurements are the same.

In yet another aspect, the invention provides a method of evaluating effects of a plurality of K different perturbations on one or more cells of a cell type, wherein K is an integer, based on measurement data comprising (i) one or more measurements $\{x_m(k)\}$ of a biological variable in one or more respective cell samples each comprising one or more cells of said cell type for each said perturbation, wherein m=1, 2, . . . , $n_k$, $n_k$ being the number of measurements for the kth perturbation, and (ii) one or more reference measurements $\{y_i\}$ of said biological variable in one or more respective reference cell samples each comprising one or more cells of said cell type under a reference condition, wherein i=1, 2, . . . , $n_r$, $n_r$ being the number of reference measurements, said method comprising (a) determining a reference mean $\bar{y}$ of said one or more reference measurements and a reference error $\sigma_y$, wherein said reference error comprises a propagated error $\sigma_p$ and a scattered error $\sigma_s$, said propagated error being determined based on predetermined experiment errors of said reference measurements, and said scattered error being determined based on deviations of said reference measurements with respect to said reference mean; (b) determining for each said measurement $x_m(k)$ a metric of difference between said measurement $x_m(k)$ and said reference mean; and (c) determining for each said measurement $x_m(k)$ an error of said metric based on a predetermined experiment error $\sigma_{x,m}(k)$ of said measurement $x_m(k)$ and said reference error $\sigma_y$, wherein said metric and said error of said metric of said measurement $x_m(k)$ is a measure of said effect of the respective perturbation. In one embodiment, said one or more measurements are replicates.

In one embodiment, said propagated error is determined according to the equation $$\sigma_p = \frac{\sqrt{\sum_i \sigma_y^2(i)}}{n_r}$$

where $\sigma_y^2(i)$ is a predetermined experiment error of measurement $y_i$, and wherein said scattered error is determined according to the equation $$\sigma_s = stdev(y_i)/\sqrt{n_r}$$

and wherein said reference error is determined according to the equation $$\sigma_y = \frac{\sigma_p + (n_r - 1) \cdot \sigma_s}{n_r}.$$

In one embodiment, the method further comprises prior to said step (b) a step of determining said predetermined experiment error $\sigma_y(i)$ for each said measurement $y_i$ and prior to said step (c) a step of determining for each said measurement $x_m(k)$ said predetermined experiment error $\sigma_{x,m}(k)$.

In one embodiment, each said predetermined experiment error $\sigma_{x,m}(k)$ and said predetermined experiment error $\sigma_y(i)$ for said measurement $y_i$ are determined according to an error model. In a preferred embodiment, said error model is a three-term error model according to equations $$\sigma_{x,m}(k) = \sqrt{\sigma_{bkg}^2 + b^2 \cdot x_m(k) + a^2 \cdot x_m(k)^2}$$

and $$\sigma_y(i) = \sqrt{\sigma_{bkg}^2 + b^2 \cdot y_i + a^2 \cdot y_i^2}$$

wherein a is a fractional error coefficient, b is a Poisson error coefficient, and $\sigma_{bkg}$ is a standard deviation of background noise. In another preferred embodiment, said error model is a two-term error model according to equations $$\sigma_{x,m}(k) = \sqrt{\sigma_{bkg}^2 + a^2 \cdot x_m(k)^2}$$

and $$\sigma_y(i) = \sqrt{\sigma_{bkg}^2 + a^2 \cdot y_i^2}$$

wherein a is a fractional error coefficient, b is a Poisson error coefficient, and $\sigma_{bkg}$ is a standard deviation of background noise.

In one embodiment, said metric of difference for each said measurement $x_m(k)$ is a ratio of said measurement $x_m(k)$ and said reference mean $\bar{y}$: $x_m(k)/\bar{y}$.

In one embodiment, said error of said metric is determined according to equation $$\sigma_{ratio,m}(k) = \sqrt{\sigma_{Logx,m}^2(k) + \sigma_{Logy}^2} \cdot \frac{x_m(k)/\bar{y}}{\text{Log}_{10}(e)}$$

where $$\sigma_{Logx,m}(k) = \text{Log}_{10}(e) \cdot \frac{\sigma_{x,m}(k)}{x_m(k)}$$

and $$\sigma_{Logy} = \text{Log}_{10}(e) \cdot \frac{\sigma_y}{\bar{y}}$$

In one embodiment, said measurement of said biological variable is a fluorescence intensity.

In some embodiments, said biological variable is an abundance of a protein. In other embodiments, said biological variable is an abundance of a transcript of a gene. In still other embodiments, said biological variable is a survival rate of cells as represented by the number of living cells measured after a chosen period of time after said perturbation.

In some embodiments, said reference condition is a condition free of the respective perturbation, and said ratio represents viability of cells of said cell type under said perturbation. In one embodiment, said reference condition is selected from the group consisting of a mock treatment of cells of said cell type, a negative control condition, and a positive control condition.

In one embodiment, said perturbation comprises subjecting cells of said cell type to one or more agents. In one embodiment, said one or more agents comprise a drug. In another embodiment, said one or more agents comprise an siRNA targeting a gene in a cell of said cell type. In another embodiment, said one or more agents comprise both a siRNA and a drug. In one embodiment that uses siRNA, said reference condition comprises subjecting cells of said cell type to an siRNA targeting luciferase.

The plurality of K perturbations can comprise at least 5, 10, 50, 100, 1,000, or 10,000 different perturbations. In one embodiment, said measurements of said plurality of K perturbations are obtained in one parallel experiment.

The invention also provides a method of evaluating effects of a plurality of N different sets of K different perturbations on cells of a cell type, wherein N and K are integers, wherein said measurement data comprises one or more measurements $\{x_m(n, k)\}$, where n=1, 2, ..., N, m=1, 2, ..., $n_k$, and k=1, 2, ..., K, using a method comprising carrying out the above mentioned method for each n∈{1, N}. In one embodiment, said measurement data further comprise for each kth group of one or more measurements one or more control measurements $\{u_l\}$ of said biological variable in a cell of said cell type under a control condition, wherein l=1, 2, ..., $n_k$, $n_k$ being the number of control measurements, and wherein said method further comprising normalizing each of said measurements $x_m(n, k)$ with an average of all of said control measurements.

In still another aspect, the invention provides a method of determining an effect of a perturbation on a biological variable in one or more cells of a cell type relative to one or more cells of said cell type under a reference condition, comprising (a) determining, for each of one or more measurements $\{x_i\}$ of said biological variable in one or more respective cell samples each comprising one or more cells of said cell type under said perturbation, a metric of difference $D_i$ between said measurement and a reference mean $\bar{y}(i)$, wherein i=1, 2, ..., $n_x$, $n_x$ being the number of said one or more measurements, wherein said reference mean $\bar{y}(i)$ is a mean of one or more reference measurements $\{y_j(i)\}$ of said biological variable in one or more respective reference cell samples each comprising one or more cells of said cell type under said reference condition, wherein j=1, 2, ..., $n_y(i)$, $n_y(i)$ being the number of reference measurements associated with measurement $x_i$; (b) determining, for each of said metric of difference $D_i$, an error $\sigma_D(i)$ based on (bi) a predetermined experiment error $\sigma_x(i)$ of said measurement $x_i$ and (bii) a reference error $\sigma_y(i)$, wherein said reference error comprises a propagated error $\sigma_{y,p}(i)$ and a scattered error $\sigma_{y,s}(i)$, said propagated error being determined based on predetermined experiment errors of said reference measurements $\{y_j(i)\}$, and said scattered error being determined based on deviations of said reference measurements $\{y_j(i)\}$ with respect to said reference mean $\bar{y}(i)$; (c) determining a mean $\bar{D}$ of said metric of difference; and (d) determining an error $\sigma_D$ for said mean $\bar{D}$ of said metric of difference, wherein said error $\sigma_D$ comprises a propagated error $\sigma_{D,p}$ and a scattered error $\sigma_{D,s}$, said propagated error being determined based on said $\sigma_D(i)$, and said scattered error being determined based on deviations of said metric of difference $\{D_i\}$ with respect to said mean $\bar{D}$ of said metric of difference, wherein said mean $\bar{D}$ of said metric of difference and said error $\sigma_D$ are a measure of said effect.

In one embodiment, said mean $\bar{D}$ of said metric of difference is a weighted mean according to the equation $$\bar{D} = \frac{\sum_i w_i D(i)}{\sum_i w_i},$$

wherein $$w_i = \frac{1}{\sigma_D^2(i)},$$

and wherein said propagated error $\sigma_{D,p}$ is determined according to equation $$\sigma_{D,p}^2 = \frac{1}{\sum_i w_i}$$

and said scattered error $\sigma_{D,s}$ is determined according to the equation $$\sigma_{D,s}^2 = \frac{1}{(n_x - 1) \cdot \sum_i w_i} \cdot \sum_i w_i \cdot [D(i) - \bar{D}]^2.$$

In one embodiment, each said metric of difference $D_i$ is a ratio of said measurement $x_i$ and said reference mean $\bar{y}(i)$: $x_i/\bar{y}(i)$.

In one embodiment, each said error $\sigma_D(i)$ is determined according to the equation $$\sigma_D(i) = \sqrt{\sigma_{Logx}^2(i) + \sigma_{Logy}^2(i)} \cdot \frac{x_i/\bar{y}(i)}{Log_{10}(e)}$$

where $$\sigma_{Logx}(i) = Log_{10}(e) \cdot \frac{\sigma_{x_i}}{x_i}$$

and $$\sigma_{Logy}(i) = Log_{10}(e) \cdot \frac{\sigma_y(i)}{\bar{y}(i)}.$$

In one embodiment, each said propagated error $\sigma_{y,p}(i)$ is determined according to equation $$\sigma_{y,p}(i) = \frac{\sqrt{\sum_j \sigma_{y,j}^2(i)}}{n_{y,i}}$$

where $\sigma_{y,j}(i)$ is a predetermined experiment error of reference measurement $y_j(i)$, wherein said scattered error $\sigma_{y,s}(i)$ is determined according to equation $$\sigma_{y,s}(i) = \operatorname*{stdev}_{i \in 1, \ldots, n_y(i)}(y_j(i)) \Big/ \sqrt{n_y(i)}$$

and wherein said reference error is determined according to equation $$\sigma_y(i) = \frac{\sigma_{y,p} + [n_y(i) - 1] \cdot \sigma_{y,s}}{n_y(i)}.$$

In another embodiment, the method further comprises prior to said step (a) a step of determining said predetermined experiment error $\sigma_{y,j}(i)$ for each said measurement $y_j(i)$; and prior to said step (b) a step of determining each said predetermined experiment error $\sigma_x(i)$ of said measurement $x_i$.

In one embodiment, said predetermined experiment error of each said measurement $x_i$ and each said reference measurement $y_j(i)$ are determined according to an error model. In a preferred embodiment, said error model is a three-term error model according to equations $$\sigma_x(i) = \sqrt{\sigma_{bkg}^2 + b^2 \cdot x_i + a^2 \cdot x_i^2}$$

and $$\sigma_{y,j}(i) = \sqrt{\sigma_{bkg}^2 + b^2 \cdot y_j(i) + a^2 \cdot y_j^2(i)}$$

wherein a is a fractional error coefficient, b is a Poisson error coefficient, and $\sigma_{bkg}$ is a standard deviation of background noise. In another preferred embodiment, said error model is a two-term error model according to equations $$\sigma_x(i) = \sqrt{\sigma_{bkg}^2 + a^2 \cdot x_i^2}$$

and $$\sigma_{y,j}(i) = \sqrt{\sigma_{bkg}^2 + a^2 \cdot y_j^2(i)}$$

wherein a is a fractional error coefficient and $\sigma_{bkg}$ is a standard deviation of background noise.

In one embodiment, said $\sigma_{bkg}$ is determined based on one or more measurements of said biological variable in a negative control sample, e.g., a sample that comprises no cells.

In one embodiment, said measurement of said biological variable is a fluorescence intensity.

In some embodiments, said biological variable is an abundance of a protein. In other embodiments, said biological variable is an abundance of a transcript of a gene. In still other embodiments, said biological variable is a survival rate of cells as represented by the number of living cells measured after a chosen period of time after said perturbation.

In some embodiments, said reference condition is a condition free of said perturbation, and said ratio represents viability of cells of said cell type under said perturbation. In one embodiment, said reference condition is selected from the group consisting of a mock treatment of cells of said cell type, a negative control condition, and a positive control condition.

In one embodiment, said perturbation comprises subjecting cells of said cell type to one or more agents. In one embodiment, said one or more agents comprise a drug. In another embodiment, said one or more agents comprise an siRNA targeting a gene in a cell of said cell type. In another embodiment, said one or more agents comprise both a siRNA and a drug. In one embodiment that uses siRNA, said reference condition comprises subjecting cells of said cell type to an siRNA targeting luciferase.

In still another aspect, the invention provides a method of determining an effect of a perturbation on a biological variable in one or more cells of a cell type relative to one or more cell of said cell type under a reference condition, comprising (a) determining a mean $\bar{x}$ of one or more measurements $\{x_i\}$ of said biological variable in one or more respective cell samples each comprising one or more cells of said cell type under said perturbation, wherein $i=1, 2, \ldots, n_x$, $n_x$ being the number of said one or more measurements; (b) determining an error $\sigma_{\bar{x}}$ of said mean $\bar{x}$, wherein said error comprises a propagated error $\sigma_{x,p}(i)$ and a scattered error $\sigma_{x,s}(i)$, said propagated error being determined based on predetermined experiment errors of said one or more measurements $\{x_i\}$, and said scattered error being determined based on deviation of said measurements $\{x_i\}$ with respect to said mean $\bar{x}$; (c) determining a metric of difference D between said mean $\bar{x}$ and a reference mean $\bar{y}$, wherein said reference mean $\bar{y}$ is a mean of one or more reference measurements $\{y_j\}$ of said biological variable in one or more respective reference cell samples each comprising one or more cells of said cell type under said reference condition, wherein $j=1, 2, \ldots, n_y$, $n_y$ being the number of reference measurements; and (d) determining (di) an error $\sigma_D$ for said metric of difference D based on said $\sigma_{\bar{x}}$, and (dii) a reference error $\sigma_{\bar{y}}$, wherein said reference error comprises a propagated error $\sigma_{y,p}$ and a scattered error $\sigma_{y,s}$, said propagated error being determined based on predetermined experiment errors of said reference measurements $\{y_j\}$, and said scattered error being determined based on deviations of said reference measurements $\{y_j\}$ with respect to said reference mean $\bar{y}$, wherein said metric of difference D and said error $\sigma_D$ are a measure of said effect.

In one embodiment, said mean $\bar{x}$ and said reference mean $\bar{y}$ are each a weighted mean according to equations $$\bar{x} = \frac{\sum_i w_{x,i} x_i}{\sum_i w_{x,i}} \text{ and } \bar{y} = \frac{\sum_j w_{y,j} y_j}{\sum_j w_{y,j}}, \text{ respectively}$$

wherein $$w_{x,i} = \frac{1}{\sigma_x^2(i)} \text{ and } w_{y,j} = \frac{1}{\sigma_y^2(j)},$$

and wherein said propagated errors $\sigma_{x,p}$ and $\sigma_{y,p}$ are determined according to equations $$\sigma_{x,p}^2 = \frac{1}{\sum_i w_{x,i}} \text{ and } \sigma_{y,p}^2 = \frac{1}{\sum_j w_{y,j}}, \text{ respectively}$$

and said scattered errors $\sigma_{x,s}$ and $\sigma_{y,s}$ are determined according to equations $$\sigma_{x,s}^2 = \frac{1}{(n_x - 1) \cdot \sum_i w_{x,i}} \cdot \sum_i w_{x,i} \cdot (x_i - \bar{x})^2$$

and $$\sigma_{y,s}^2 = \frac{1}{(n_y - 1) \cdot \sum_j w_{y,j}} \cdot \sum_j w_{y,j} \cdot (y_j - \bar{y})^2.$$

In one embodiment, said metric of difference is a ratio of said mean $\bar{x}$ and said reference mean $\bar{y}$: $\bar{x}/\bar{y}$.

In one embodiment, said error of said metric $\sigma_D$ is determined according to equation $$\sigma_D = \sqrt{\sigma_{Logx}^2 + \sigma_{Logy}^2} \cdot \frac{\bar{x}/\bar{y}}{\text{Log}_{10}(e)}$$

where $$\sigma_{Logx} = \text{Log}_{10}(e) \cdot \frac{\sigma_{\bar{x}}}{\bar{x}}$$

and $$\sigma_{Logy} = \text{Log}_{10}(e) \cdot \frac{\sigma_{\bar{y}}}{\bar{y}}.$$

In one embodiment, each said propagated error $\sigma_{y,p}(i)$ is determined according to equation $$\sigma_{y,p}(i) = \frac{\sqrt{\sum_j \sigma_{y,j}^2(i)}}{n_{y,i}}$$

where $\sigma_{y,j}(i)$ is a predetermined experiment error of reference measurement $y_j(i)$, wherein said scattered error $\sigma_{y,s}(i)$ is determined according to equation $$\sigma_{y,s}(i) = \underset{i \in 1, \ldots, n_y(i)}{stdev}(y_j(i)) \Big/ \sqrt{n_y(i)}$$

and wherein said reference error is determined according to equation $$\sigma_y(i) = \frac{\sigma_{y,p} + [n_y(i) - 1] \cdot \sigma_{y,s}}{n_y(i)}.$$

In another embodiment, the method further comprises prior to said step (a) a step of determining said predetermined experiment error $\sigma_{y,j}(i)$ for each said measurement $y_j(i)$ and prior to said step (b) a step of determining each said predetermined experiment error $\sigma_x(i)$ of said measurement $x_i$.

In one embodiment, said predetermined experiment error of each said measurement $x_i$ and each said reference measurement $y_j(i)$ are determined according to an error model. In a preferred embodiment, said error model is a three-term error model according to equations $$\sigma_x(i) = \sqrt{\sigma_{bkg}^2 + b^2 \cdot x_i + a^2 \cdot x_i^2}$$

and $$\sigma_{y,j}(i) = \sqrt{\sigma_{bkg}^2 + b^2 \cdot y_j(i) + a^2 \cdot y_j^2(i)}$$

wherein a is a fractional error coefficient, b is a Poisson error coefficient, and $\sigma_{bkg}$ is a standard deviation of background noise. In another preferred embodiment, said error model is a two-term error model according to equations $$\sigma_x(i) = \sqrt{\sigma_{bkg}^2 + a^2 \cdot x_i^2}$$

and $$\sigma_{y,j}(i) = \sqrt{\sigma_{bkg}^2 + a^2 \cdot y_j^2(i)}$$

wherein a is a fractional error coefficient and $\sigma_{bkg}$ is a standard deviation of background noise.

In one embodiment, said $\sigma_{bkg}$ is determined based on one or more measurements of said biological variable in a negative control sample, a sample that comprises no cells.

In one embodiment, said measurement of said biological variable is a fluorescence intensity.

In some embodiments, said biological variable is an abundance of a protein. In other embodiments, said biological variable is an abundance of a transcript of a gene. In still other embodiments, said biological variable is a survival rate of cells as represented by the number of living cells measured after a chosen period of time after said perturbation.

In some embodiments, said reference condition is a condition free of said perturbation, and said ratio represents viability of cells of said cell type under said perturbation. In one embodiment, said reference condition is selected from the group consisting of a mock treatment of cells of said cell type, a negative control condition, and a positive control condition.

In one embodiment, said perturbation comprises subjecting cells of said cell type to one or more agents. In one embodiment, said one or more agents comprise a drug. In another embodiment, said one or more agents comprise an siRNA targeting a gene in a cell of said cell type. In another embodiment, said one or more agents comprise both a siRNA and a drug. In one embodiment that uses siRNA, said reference condition comprises subjecting cells of said cell type to an siRNA targeting luciferase.

In still another aspect, the invention provides a method of comparing effect of a first perturbation on a biological variable in one or more cells of a cell type and a second perturbation on said biological variable in one or more cells of said cell type, comprising (a) determining (ai) a first mean of a first metric of difference $\overline{D}_1$; and (aii) an error $\sigma_{D,1}$ for said first mean by a method comprising (a1) determining, for each of one or more first measurements $\{x_{1,i}\}$ of said biological variable in one or more respective first cell samples each comprising one or more cells of said cell type under said first perturbation, a first metric of difference $D_{1,i}$ between said first measurement and a first reference mean $\overline{y}_1(i)$, wherein i=1, 2, ..., $n_{1,x}$, $n_{1,x}$ being the number of said one or more first measurements, wherein said first reference mean $\overline{y}(i)$ is a mean of one or more first reference measurements $\{y_{1,j}(i)\}$ of said biological variable in one or more respective first reference cell samples each comprising one or more cells of said cell type under said reference condition, wherein j=1, 2, ..., $n_{1,y}(i)$, $n_{1,y}(i)$ being the number of first reference measurements associated with measurement $x_{1,i}$; (a2) determining, for each said first metric of difference $D_{1,i}$, an error $\sigma_{1,D}(i)$ based on a predetermined experiment error $\sigma_{1,x}(i)$ of said measurement $x_{1,i}$ and a first reference error $\sigma_{1,y}(i)$, wherein said first reference error comprises a propagated error $\sigma_{1,y,p}(i)$ and a scattered error $\sigma_{1,y,s}(i)$, said propagated error being determined based on predetermined experiment errors of said reference measurements $\{y_{1,j}(i)\}$, and said scattered error being determined based on deviations of said reference measurements $\{y_{1,j}(i)\}$ with respect to said reference mean $\overline{y}_1(i)$; (a3) determining a mean $\overline{D}_1$ of said first metric of difference; and (a4) determining an error $\sigma_{1,D}$ for said mean $\overline{D}_1$ of said first metric of difference, wherein said error $\sigma_{1,D}$ comprises a first propagated error $\sigma_{1,D,p}$ and a first scattered error $\sigma_{1,D,s}$, said first propagated error being determined based on each said $\sigma_{1,D}(i)$, and said first scattered error being determined based on deviations of said first metrics of difference $\{D_{1,i}\}$ with respect to said first mean $\overline{D}_1$ of said first metric of difference; (b) determining (bi) a second mean $\overline{D}_2$ of a second metric of difference, and (bii) an error $\sigma_{2,D}$ for said second mean by a method comprising (b1) determining, for each of one or more second measurements $\{x_{2,k}\}$ of said biological variable in one or more respective second cell samples each comprising one or more cells of said cell type under said second perturbation, a second metric of difference $D_{2,k}$ between said second measurement and a second reference mean $\overline{y}_2(k)$, wherein k=1, 2, ..., $n_{2,x}$, $n_{2,x}$ being the number of said one or more second measurements, wherein said second reference mean $\overline{y}_2(k)$ is a mean of one or more second reference measurements $\{y_{2,l}(k)\}$ of said biological variable in one or more respective second reference cell samples each comprising one or more cells of said cell type under said reference condition, wherein l=1, 2, ..., $n_{2,l}(k)$, $n_{2,l}(k)$ being the number of second reference measurements corresponding to measurement $x_{1,j}$; (b2) determining, for each said second metric of difference $D_{2,k}$, an error $\sigma_{2,D}(k)$ based on a predetermined experiment error $\sigma_{2,x}(k)$ of said measurement $x_{2,i}$ and a reference error $\sigma_{2,y}(k)$, wherein said second reference error comprises a propagated error $\sigma_{2,y,p}(k)$ and a scattered error $\sigma_{2,y,s}(k)$, said propagated error being determined based on predetermined experiment errors of said reference measurements $\{y_{2,i}(k)\}$, and said scattered error being determined based on deviations of said reference measurements $\{y_{2,i}(k)\}$ with respect to said reference mean $\bar{y}_2(k)$; (b3) determining a mean $\bar{D}_2$ of said second metric of difference; and (b4) determining an error $\sigma_{2,D}$ for said mean $\bar{D}_2$ of said second metric difference, wherein said error $\sigma_{2,D}$ comprises a second propagated error $\sigma_{2,D,p}$ and a second scattered error $\sigma_{2,D,s}$, said second propagated error being determined based on each said $\sigma_{2,D}(k)$, and said second scattered error being determined based on deviations of said second metrics of difference $\{D_{2,k}\}$ with respect to said second mean $\bar{D}_2$ of said second metric of difference; and (c) comparing $\bar{D}_1$, $\sigma_{1,D}$ with $\bar{D}_2$, $\sigma_{2,D}$, thereby comparing said effect of said first perturbation and said second perturbation.

In one embodiment, said step (c) is carried out by a method comprising determining (c1) a parameter xdev according to equation $$xdev = \frac{\bar{D}_1 - \bar{D}_2}{\sqrt{\sigma_{1,D}^2 + \sigma_{2,D}^2}},$$

and (c2) a p-value for said parameter xdev according to equation $$p\text{-value}=2\cdot Erf(|xdev|)$$

wherein said xdev and p-value are measures of said comparison.

In another embodiment, said step (c) further comprises determining (c3) a log ratio according to equation $$lratio=\log_{10}(\bar{D}_1/\bar{D}_2)$$

and (c4) an error of said log ratio according to equation $$\sigma_{lratio} = \left|\frac{lratio}{xdev}\right|.$$

In another embodiment, said first and second propagated errors are determined according to equations $$\sigma_{1,p} = \frac{\sqrt{\sum_i \sigma_{1,y}^2(i)}}{n_{1,r}} \text{ and } \sigma_{2,p} = \frac{\sqrt{\sum_j \sigma_{2,y}^2(j)}}{n_{2,r}}, \text{ respectively,}$$

where $\sigma_{1,y}^2(i)$ and $\sigma_{2,y}^2(j)$ are predetermined experiment errors of measurement $y_{1,i}$ and $y_{1,h}$, respectively, wherein said first and second scattered errors are determined according to equations $$\sigma_{1,s} = \underset{i\in 1,2,\ldots,n_{1,r}}{stdev(y_{1,i})}\Big/\sqrt{n_{1,r}} \text{ and } \sigma_{2,s} = \underset{j\in 1,2,\ldots,n_{2,r}}{stdev(y_{2,j})}\Big/\sqrt{n_{2,r}}, \text{ respectively,}$$

and wherein said first and second reference errors are determined according to equation $$\sigma_{1,y} = \frac{\sigma_{1,p} + (n_{1,r}-1)\cdot\sigma_{1,s}}{n_{1,r}} \text{ and } \sigma_{2,y} = \frac{\sigma_{2,p} + (n_{2,r}-1)\cdot\sigma_{2,s}}{n_{2,r}},$$

respectively.

In one embodiment, the method further comprises (i) prior to said step (a1) a step of determining said predetermined experiment error $\sigma_{1,y}(i)$ for each said measurement $y_{1,i}$ and prior to said step (a3) a step of determining said predetermined experiment error $\sigma_{1,x}$ for said measurement $x_1$; and (ii) prior to said step (b1) a step of determining said predetermined experiment error $\sigma_{2,y}(j)$ for each said measurement $y_{2,j}$ and prior to said step (b3) a step of determining said predetermined experiment error $\sigma_{2,x}$ for said measurement $x_2$.

In one embodiment, said predetermined experiment errors of said measurements $x_1$ and $x_2$, and said reference measurements $\{y_{1,i}\}$ and $\{y_{2,j}\}$ are determined according to an error model. In a preferred embodiment, said error model is a three-term error model according to equations $$\sigma_{1,x}=\sqrt{\sigma_{bkg}^2+b^2\cdot x_1+a^2\cdot x_1^2} \text{ and } \sigma_{2,x}=\sqrt{\sigma_{bkg}^2+b^2\cdot x_2+a^2\cdot x_2^2}$$

and equations $$\sigma_{1,y}(i)=\sqrt{\sigma_{bkg}^2+b^2\cdot y_{1,i}+a^2\cdot y_{1,i}^2} \text{ and } \sigma_{2,y}(j)=\sqrt{\sigma_{bkg}^2+b^2\cdot y_{2,j}+a^2\cdot y_{2,j}^2}$$

wherein a is a fractional error coefficient, b is a Poisson error coefficient, and $\sigma_{bkg}$ is a standard deviation of background noise. In another preferred embodiment, said error model is a two-term error model according to equations $$\sigma_{1,x}=\sqrt{\sigma_{bkg}^2+a^2\cdot x_1^2} \text{ and } \sigma_{2,x}=\sqrt{\sigma_{bkg}^2+a^2\cdot x_2^2}$$

and equations $$\sigma_{1,y}(i)=\sqrt{\sigma_{bkg}^2+a^2\cdot y_{1,i}^2} \text{ and } \sigma_{2,y}(j)=\sqrt{\sigma_{bkg}^2+a^2\cdot y_{2,j}^2}$$

wherein a is a fractional error coefficient, and $\sigma_{bkg}$ is a standard deviation of background noise.

In another embodiment, said $\sigma_{bkg}$ is determined based on one or more measurements of said biological variable in a negative control sample, e.g., a sample that comprises no cells.

In one embodiment, said first metric of difference is a ratio of said first measurement $x_1$ and said first reference mean $\bar{y}_1$: $z_1=x_1/\bar{y}_1$ and said second metric of difference is a ratio of said second measurement $x_2$ and said second reference mean $\bar{y}_2$: $z_2=x_2/\bar{y}_2$. In one embodiment, said first and second errors of said metric is determined according to equations $$\sigma_{1,ratio} = \sqrt{\sigma_{1,Logx}^2 + \sigma_{1,Logy}^2}\cdot\frac{z_1}{\text{Log}_{10}(e)} \text{ and } \sigma_{2,ratio} = \sqrt{\sigma_{2,Logx}^2 + \sigma_{2,Logy}^2}\cdot\frac{z_2}{\text{Log}_{10}(e)}$$

respectively, where $$\sigma_{1,Logx} = \text{Log}_{10}(e)\cdot\frac{\sigma_{1,x}}{x_1} \text{ and } \sigma_{2,Logx} = \text{Log}_{10}(e)\cdot\frac{\sigma_{2,x}}{x_2}$$

and $$\sigma_{1,Logy} = \text{Log}_{10}(e)\cdot\frac{\sigma_{1,y}}{\bar{y}_1} \text{ and } \sigma_{2,Logy} = \text{Log}_{10}(e)\cdot\frac{\sigma_{2,y}}{\bar{y}_2}$$

In one embodiment, said measurement of said biological variable is a fluorescence intensity.

In some embodiments, said biological variable is an abundance of a protein. In other embodiments, said biological variable is an abundance of a transcript of a gene. In still other embodiments, said biological variable is a survival rate of cells as represented by the number of living cells measured after a chosen period of time after said first and second perturbation.

In one embodiment, said first and second reference conditions are conditions free from said first and second perturbations, and each said ratio represents viability of cells of said cell type under the respective perturbation. In one embodiment, said first perturbation comprises subjecting cells of said cell type to one or more first agents and said second perturbation comprises subjecting cells of said cell type to one or more second agents. In a specific embodiment, said first and second reference conditions are the same condition selected from the group consisting of a mock treatment of cells of said cell type, a negative control condition, and a positive control condition.

In one embodiment, said one or more first agents comprise a first drug and said one or more second agents comprise a second drug. In a specific embodiment, said first drug and said second drug are the same drug of different doses.

In another embodiment, said one or more first agents comprise a first siRNA targeting a first gene of said cell type and said one or more second agents comprise a second siRNA targeting a second gene, different from said first gene, of said cell type. In one embodiment, said first and second reference conditions are the same condition that comprises subjecting cells of said cell type to an siRNA targeting luciferase. In another embodiment, said one or more first agents comprise both a first drug and said first siRNA and said one or more second agents comprise both said second siRNA and a second drug.

In one embodiment, said first and second reference conditions are the same. In another embodiment, said first and second reference measurements are the same.

In still another aspect, the invention provides a method of comparing effects of a plurality of M perturbations on a biological variable in one or more cells of a cell type, comprising (a) determining a set of metrics of difference and the associated errors $\{D_{m,i}, \sigma_{m,D}(i)\}$ for each of said M perturbations, wherein m=1, 2, ..., M, wherein i=1, 2, ..., $n_{m,x}$, $n_{m,x}$ being the number of measurements for the mth perturbation, by a method comprising, for each of one or more measurements of the mth perturbation $\{x_{m,i}\}$ of said biological variable in one or more respective cell samples each comprising one or more cells of said cell type under said mth perturbation, (a1) determining a metric of difference $D_{m,i}$ between said ith measurement and a reference mean $\bar{y}_m(i)$, wherein said reference mean $\bar{y}_m(i)$ is a mean of one or more reference measurements $\{y_{m,j}(i)\}$ of said biological variable in one or more respective reference cell samples each comprising one or more cells of said cell type under a reference condition, wherein j=1, 2, ..., $n_{m,j}(i)$, $n_{m,j}(i)$ being the number of reference measurements associated with measurement $x_{m,j}$; and (a2) determining, for each of said ith metric of difference $D_{m,i}$, (a2i) an error $\sigma_{m,D}(i)$ based on a predetermined experiment error $\sigma_{m,x}(i)$ of said measurement $x_{1,i}$, and (a2ii) a reference error $\sigma_{m,y}(i)$, wherein said reference error comprises a propagated error $\sigma_{m,y,p}(i)$ and a scattered error $\sigma_{m,y,s}(i)$, said propagated error being determined based on predetermined experiment errors of said reference measurements $\{y_{m,j}(i)\}$, and said scattered error being determined based on deviations of said reference measurements $y_{m,j}(i)$ with respect to said reference mean $\bar{y}_m(i)$; and (b) comparing said M sets of metrics of difference and associated errors $\{D_{m,i}, \sigma_{m,D}(i)\}$, thereby comparing said effect of said plurality of perturbations.

In one embodiment, said step (a) further comprises the steps of (a3) determining a mean $\bar{D}_m$ of said mth metric of difference; and (a4) determining an error $\sigma_{m,D}$ for said mean $\bar{D}_m$ of said mth metric of difference, wherein said error $\sigma_{m,D}$ comprises a mth propagated error $\sigma_{m,D,p}$ and a mth scattered error $\sigma_{m,D,s}$, said mth propagated error being determined based on each said $\sigma_{m,D}(i)$, and said mth scattered error being determined based on deviation of each said mth metric of difference $D_{m,i}$ with respect to said mean $\bar{D}_m$ of said mth metric of difference, and said step (b) is carried out by a method comprising comparing the sets $\{\bar{D}_m, \sigma_{m,D}\}$.

In one embodiment, said step (b) is carried out by a method comprising determining (b1) a parameter xdev between sets data characterizing two perturbations $\{\bar{D}_{m_1}, \sigma_{m_1,D}\}$ and $\{\bar{D}_{m_2}, \sigma_{m_2,D}\}$ according to equation $$xdev = \frac{\bar{D}_{m_1} - \bar{D}_{m_2}}{\sqrt{\sigma_{m_1,D}^2 + \sigma_{m_2,D}^2}},$$

where $m_1, m_2 \in \{1, 2, ..., K\}$ and (b2) a p-value for said parameter xdev according to equation $p$-value=$2 \cdot Erf(|xdev|)$ wherein said xdev and p-value are measures of said comparing.

In another embodiment, said step (b) further comprises determining (b3) a log ratio according to equation $lratio = \log_{10}(\bar{D}_{m_1}/\bar{D}_{m_2})$ and (b4) an error of said log ratio according to equation $$\sigma_{lratio} = \left|\frac{lratio}{xdev}\right|.$$

In one embodiment, said step (c) is carried out by a method comprising carrying out ANOVA analysis of said sets $\{D_{m,i}, \sigma_{m,D}(i)\}$.

In one embodiment, each said propagated error is determined according to equation $$\sigma_{m,p} = \frac{\sqrt{\sum_i \sigma_{m,y}^2(i)}}{n_{m,r}},$$

where $\sigma_{m,y}(i)$ is a predetermined experiment error of measurement $y_{m,i}$, wherein each said scattered error is determined according to equation $$\sigma_{m,s} = stdev(y_{m,i})_{i \in 1,2,...,n_{m,r}} / \sqrt{n_{m,r}}$$

and wherein each said reference error is determined according to equation $$\sigma_{m,y} = \frac{\sigma_{m,p} + (n_{m,r} - 1) \cdot \sigma_{m,s}}{n_{m,r}}.$$

In another embodiment, the method further comprises, for each said perturbation, prior to said step (a1) a step of determining said predetermined experiment error $\sigma_{m,y}(i)$ for each said measurement $y_{m,i}$, and prior to said step (a3) a step of determining said predetermined experiment error $\sigma_{m,x}$ for said measurement $x_m$.

In one embodiment, said predetermined experiment errors of said measurements $x_m$ and said measurements $\{y_{m,i}\}$ are determined according to an error model. In a preferred embodiment, said error model is a three-tern error model according to the equation $$\sigma_{m,x} = \sqrt{\sigma_{bkg}^2 + b^2 \cdot x_m + a^2 \cdot x_m^2}$$

and the equation $$\sigma_{m,y}(i) = \sqrt{\sigma_{bkg}^2 + b^2 \cdot y_{m,i} + a^2 \cdot y_{m,i}^2}$$

wherein a is a fractional error coefficient, b is a Poisson error coefficient, and $\sigma_{bkg}$ is a standard deviation of background noise. In another preferred embodiment, said error model is a two-term error model according to the equation $$\sigma_{m,x} = \sqrt{\sigma_{bkg}^2 + a^2 \cdot x_m^2}$$

and the equation $$\sigma_{m,y}(i) = \sqrt{\sigma_{bkg}^2 + a^2 \cdot y_{m,i}^2}$$

wherein a is a fractional error coefficient, and $\sigma_{bkg}$ is a standard deviation of background noise.

In one embodiment, said $\sigma_{bkg}$ is determined based on one or more measurements of said biological variable in a negative control sample, e.g., a sample that comprises no cells.

In one embodiment, each said metric of difference is a ratio of measurement $x_m$ and the corresponding reference mean $\bar{y}_m$: $D_m = x_m / \bar{y}_m$.

In one embodiment, each said error of said metric is determined according to equation $$\sigma_{m,ratio} = \sqrt{\sigma_{m,Logx}^2 + \sigma_{m,Logy}^2} \cdot \frac{D_m}{Log_{10}(e)}$$

where $$\sigma_{m,Logx} = Log_{10}(e) \cdot \frac{\sigma_{m,x}}{x_m}$$

and $$\sigma_{m,Logy} = Log_{10}(e) \cdot \frac{\sigma_{m,y}}{\bar{y}_m}$$

In one embodiment, said measurement of said biological variable is a fluorescence intensity.

In some embodiments, said biological variable is an abundance of a protein. In other embodiments, said biological variable is an abundance of a transcript of a gene. In still other embodiments, said biological variable is a survival rate of cells as represented by the number of living cells measured after a chosen period of time after said first and second perturbation.

In one embodiment, said first and second reference conditions are conditions free from said first and second perturbations, and each said ratio represents viability of cells of said cell type under the respective perturbation. In one embodiment, said first perturbation comprises subjecting cells of said cell type to one or more first agents and said second perturbation comprises subjecting cells of said cell type to one or more second agents. In a specific embodiment, said first and second reference conditions are the same condition selected from the group consisting of a mock treatment of cells of said cell type, a negative control condition, and a positive control condition.

In one embodiment, said one or more first agents comprise a first drug and said one or more second agents comprise a second drug. In a specific embodiment, said first drug and said second drug are the same drug of different doses.

In another embodiment, said one or more first agents comprise a first siRNA targeting a first gene of said cell type and said one or more second agents comprise a second siRNA targeting a second gene, different from said first gene, of said cell type. In one embodiment, said first and second reference conditions are the same condition that comprises subjecting cells of said cell type to an siRNA targeting luciferase. In another embodiment, said one or more first agents comprise both a first drug and said first siRNA and said one or more second agents comprise both said second siRNA and a second drug.

In one embodiment, said first and second reference conditions are the same. In another embodiment, said first and second reference measurements are the same.

The invention also provides a system for detecting a change in measurement of a biological variable in a cell sample of a cell type relative to measurement of said biological variable in a reference cell sample of said cell type, comprising (a) means for determining a reference mean $\bar{y}$ of one or more reference measurements $\{y_i\}$ of said biological variable in said reference cell sample, wherein i=1, 2, . . . , $n_r$, $n_r$ being the number of reference measurements, and a reference error $\sigma_y$, wherein said reference error comprises a propagated error $\sigma_p$ and a scattered error $\sigma_s$, said propagated error being determined based on predetermined experiment errors of said reference measurements, and said scattered error being determined based on deviation of said reference measurements with respect to said reference mean; (b) means for determining a metric of difference between a measurement x of said biological variable in said cell sample and said reference mean; and (c) means for determining an error of said metric based on a predetermined experiment error $\sigma_x$ of said measurement x and said reference error $\sigma_y$, wherein said metric and said error for said metric is a measure of said change.

The invention further provides a method of evaluating effects of a plurality of K different perturbations on cells of a cell type, wherein K is an integer, wherein said K different perturbations are measured in L different experiments, each of said L different experiments comprises l perturbations such that the K different perturbations are measured in said L experiments, wherein said measurement data comprises (i) one or more measurements $\{x_{m,l}(k)\}$ of a biological variable in cells of said cell type for each said perturbation, wherein m=1, 2, . . . , $n_l$, $n_l$ being the number of measurements for the lth experiment, and (ii) one or more control measurements $\{y_{l}\}$ of said biological variable in cells of said cell type for the lth experiment, said method comprising (a) calculating an average of said control measurements over said L experiments; and (b) normalizing each said measurement $x_{m,l}(k)$ using said average, wherein each said normalized measurement represents the effect of a corresponding perturbation.

The invention further provides a computer system comprising a processor, and a memory coupled to said processor and encoding one or more programs, wherein said one or more programs cause the processor to carry out any one of the methods of the invention.

The invention further provides a computer program product for use in conjunction with a computer having a processor and a memory connected to the processor, said computer program product comprising a computer readable storage medium having a computer program mechanism encoded thereon, wherein said computer program mechanism may be

4. BRIEF DESCRIPTION OF FIGURES

Figure 6A:
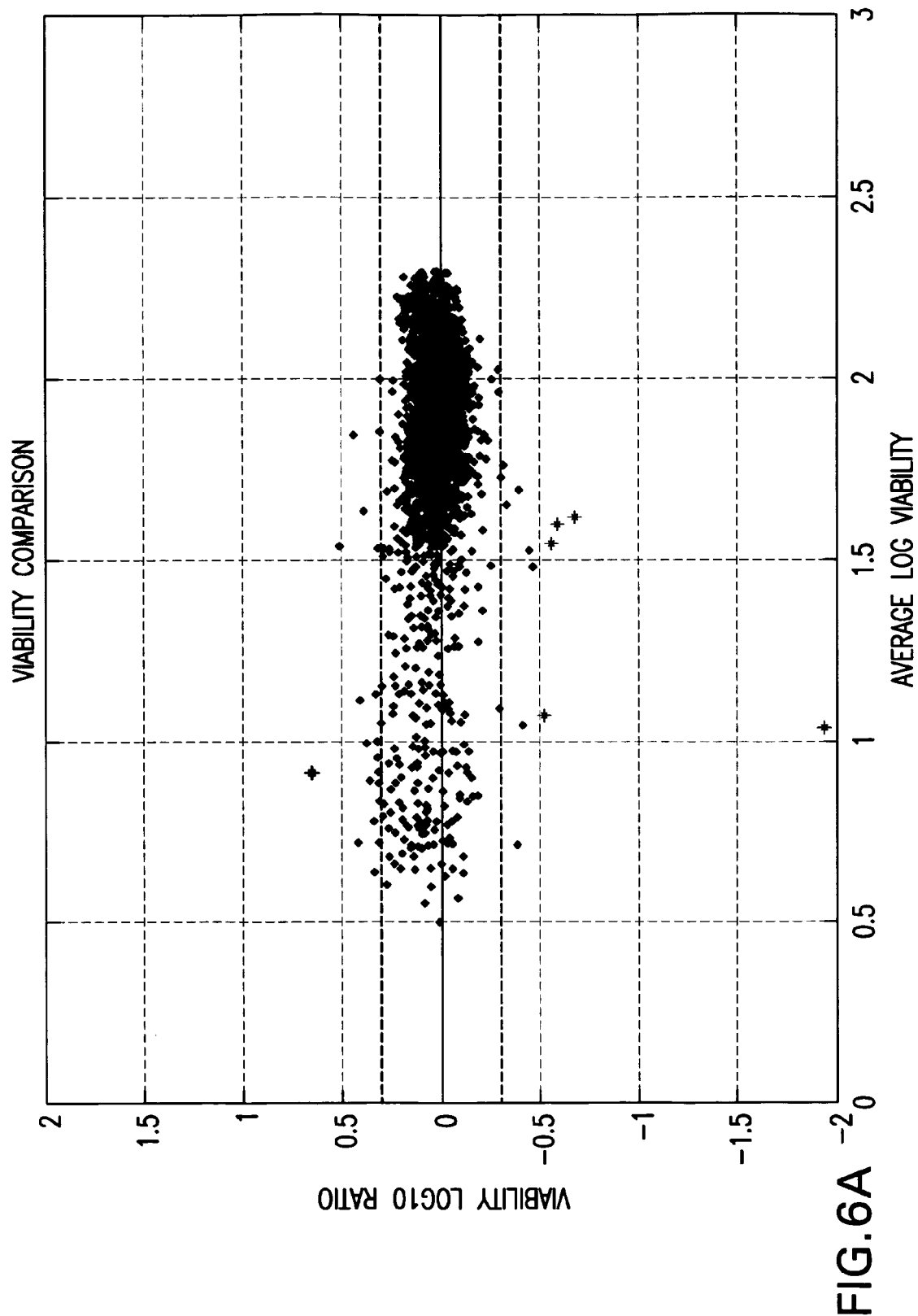
Figure 6B:
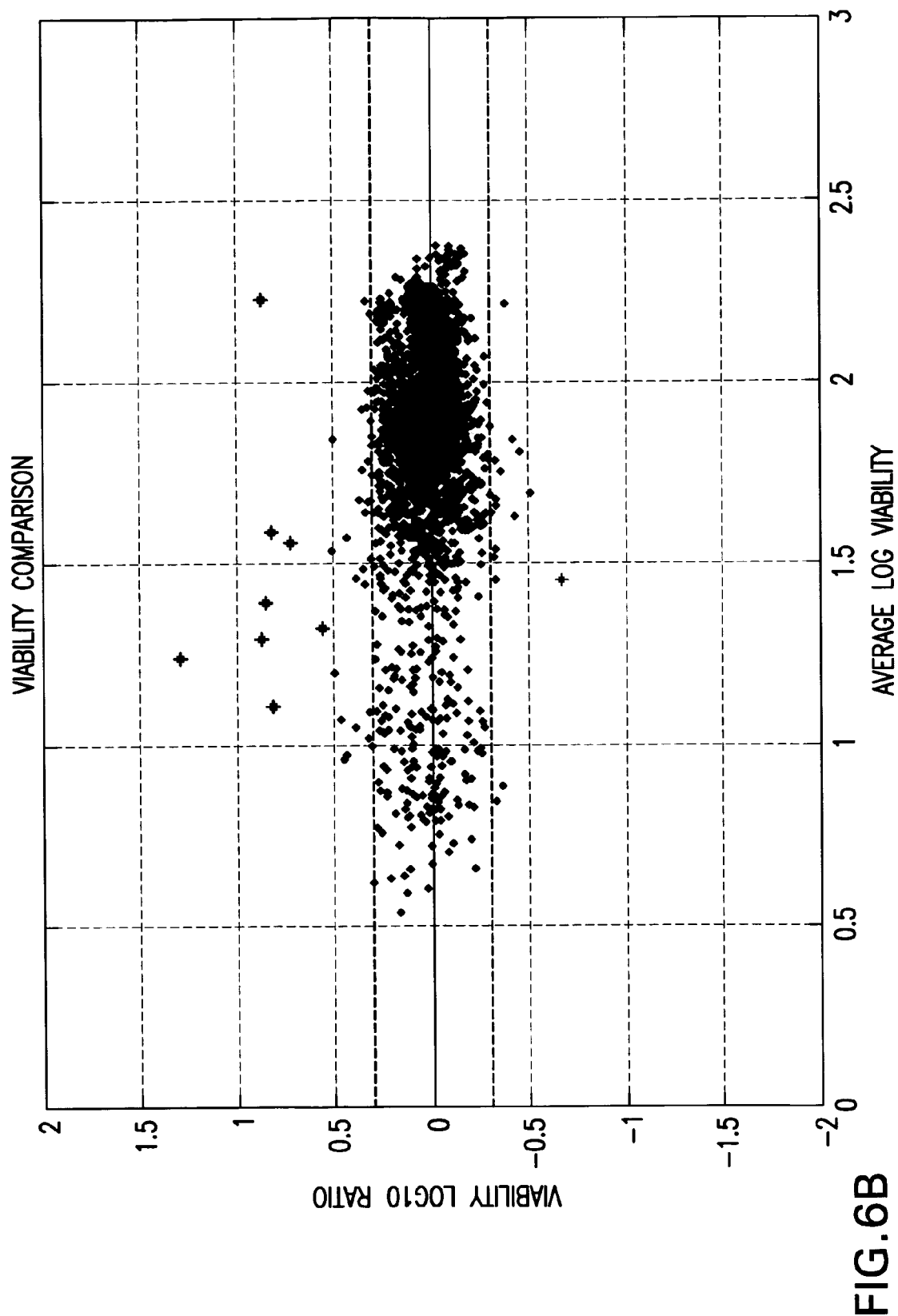

FIG. 6 shows a signature plot of a same-vs.-same experiment when P-Value<0.01, (a) no-drug; (b) low-drug: 7-gemcitabine. Up-regulated genes are shown in large dark star symbols (*), down-regulated in large light star symbols (*). Small dots are genes considered no change in differential viability. Two parallel dash lines indicate 2-fold changes.

Figure 7:
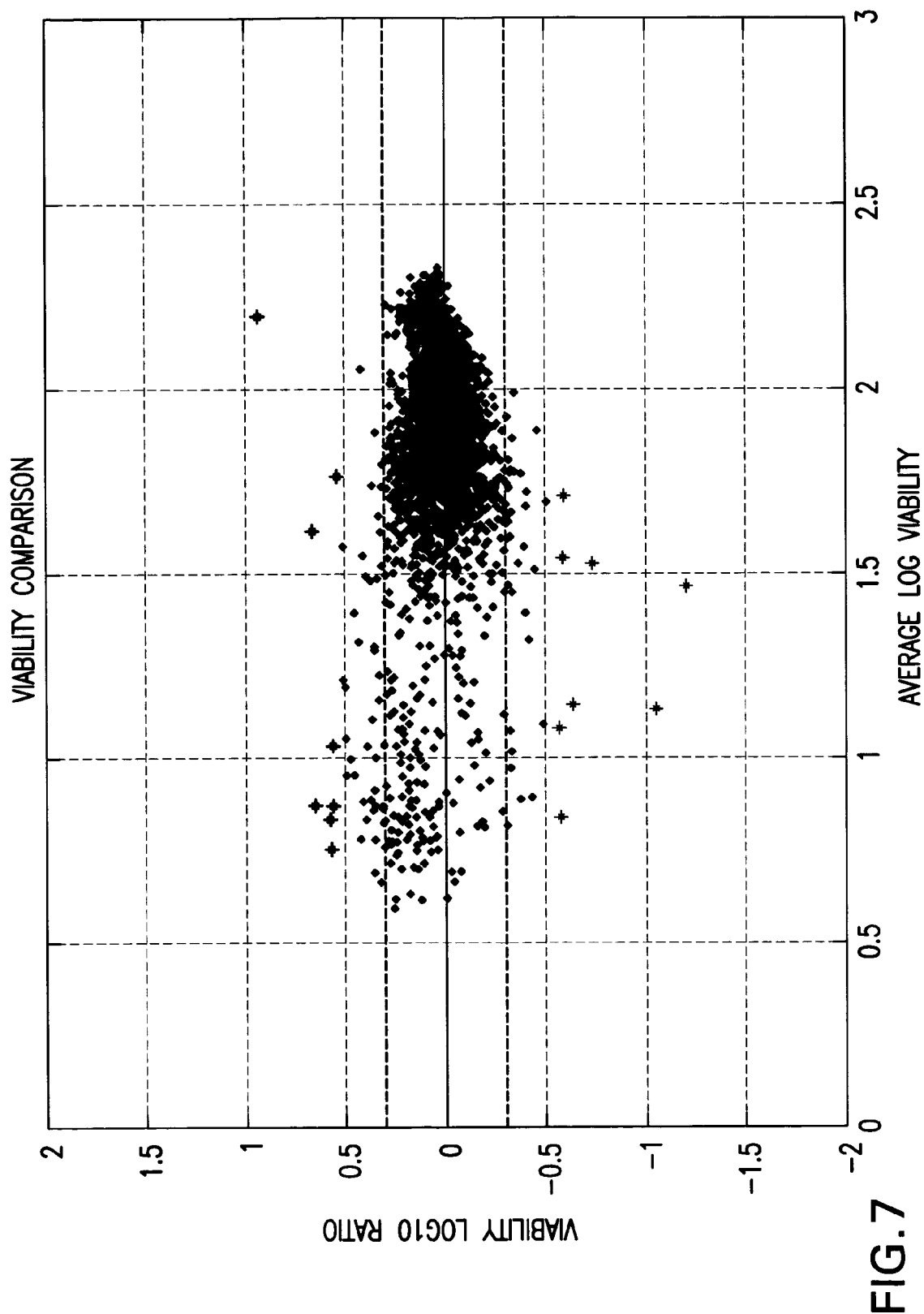

FIG. 7 shows a signature plot of a no-drug versus low-drug (7-gemcitabine) experiment without replicates (P-Value<0.01).

Figure 8:
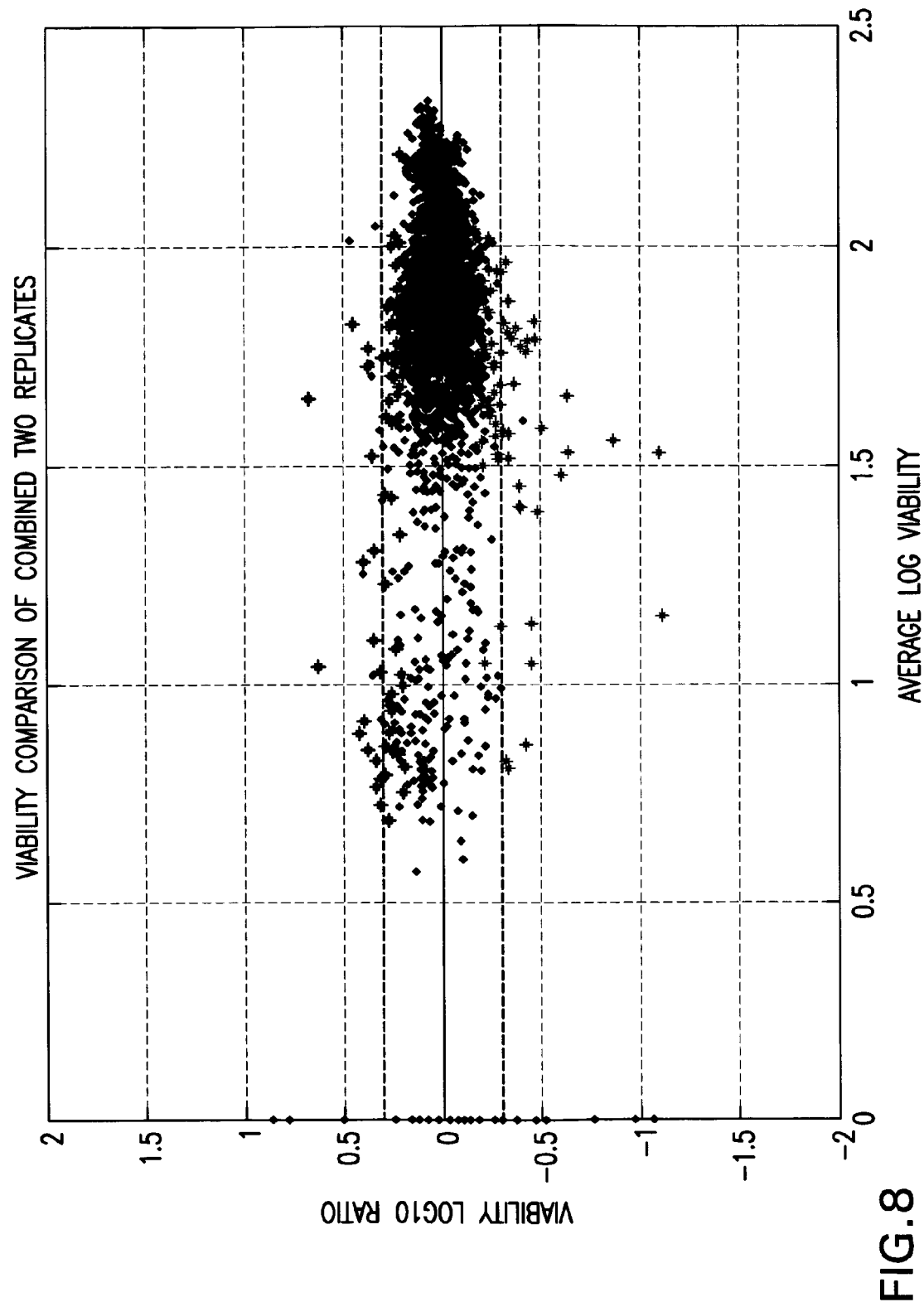

FIG. 8 shows a signature plot of a no-drug versus low-drug (7-gemcitabine) experiment with two replicates for each condition (P-Value<0.01).

Figure 9:
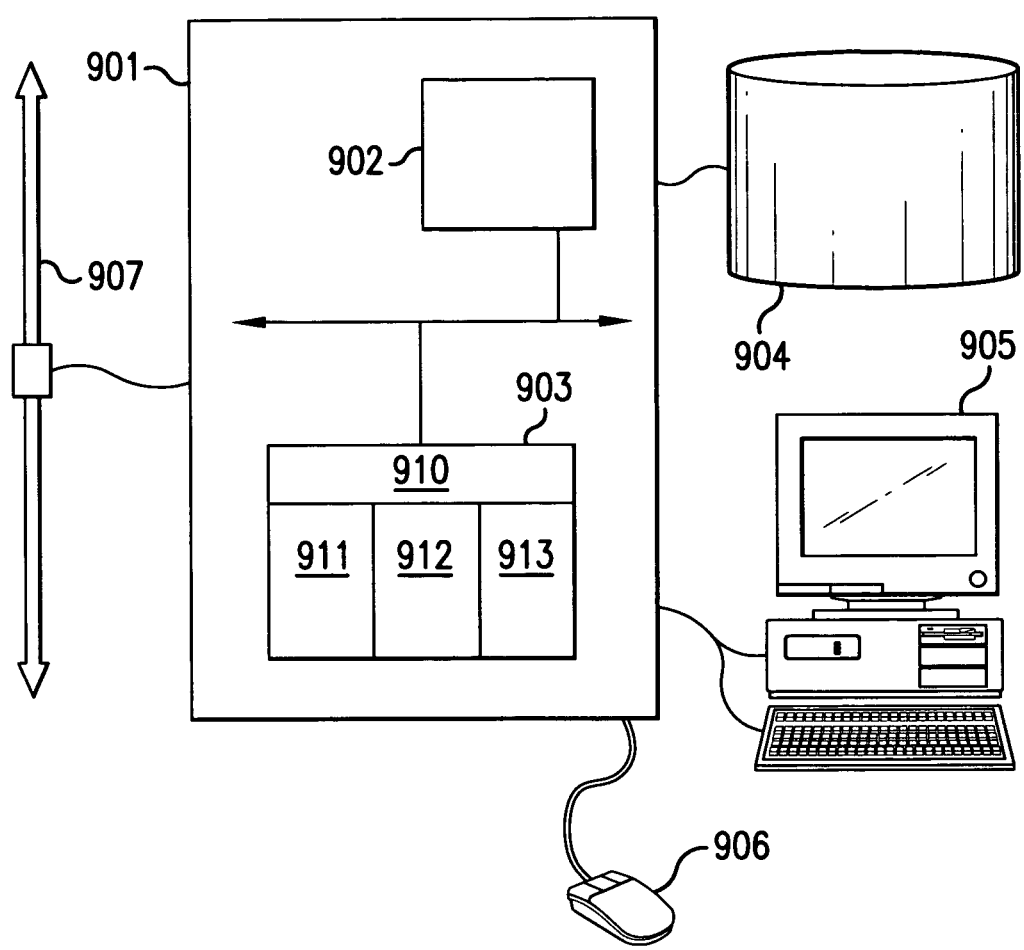

FIG. 9 illustrates an exemplary embodiment of a computer system useful for implementing the methods of this invention.

Figure 10A:
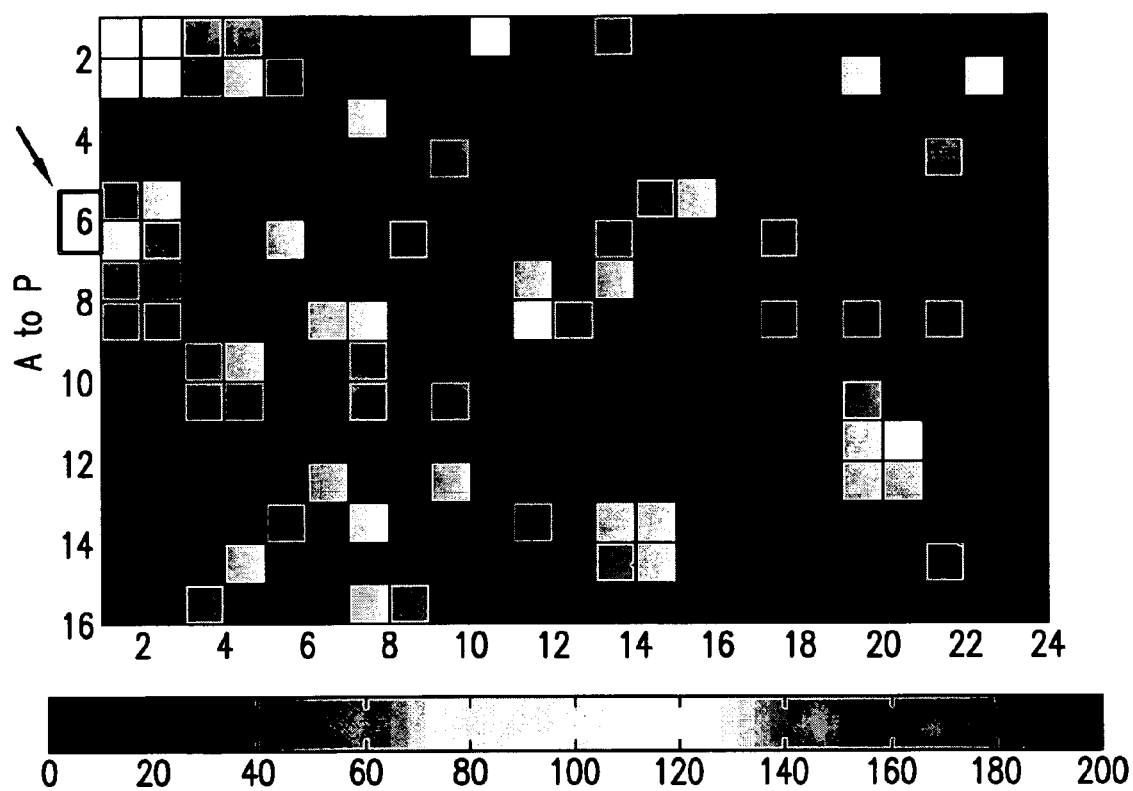
Figure 10B:
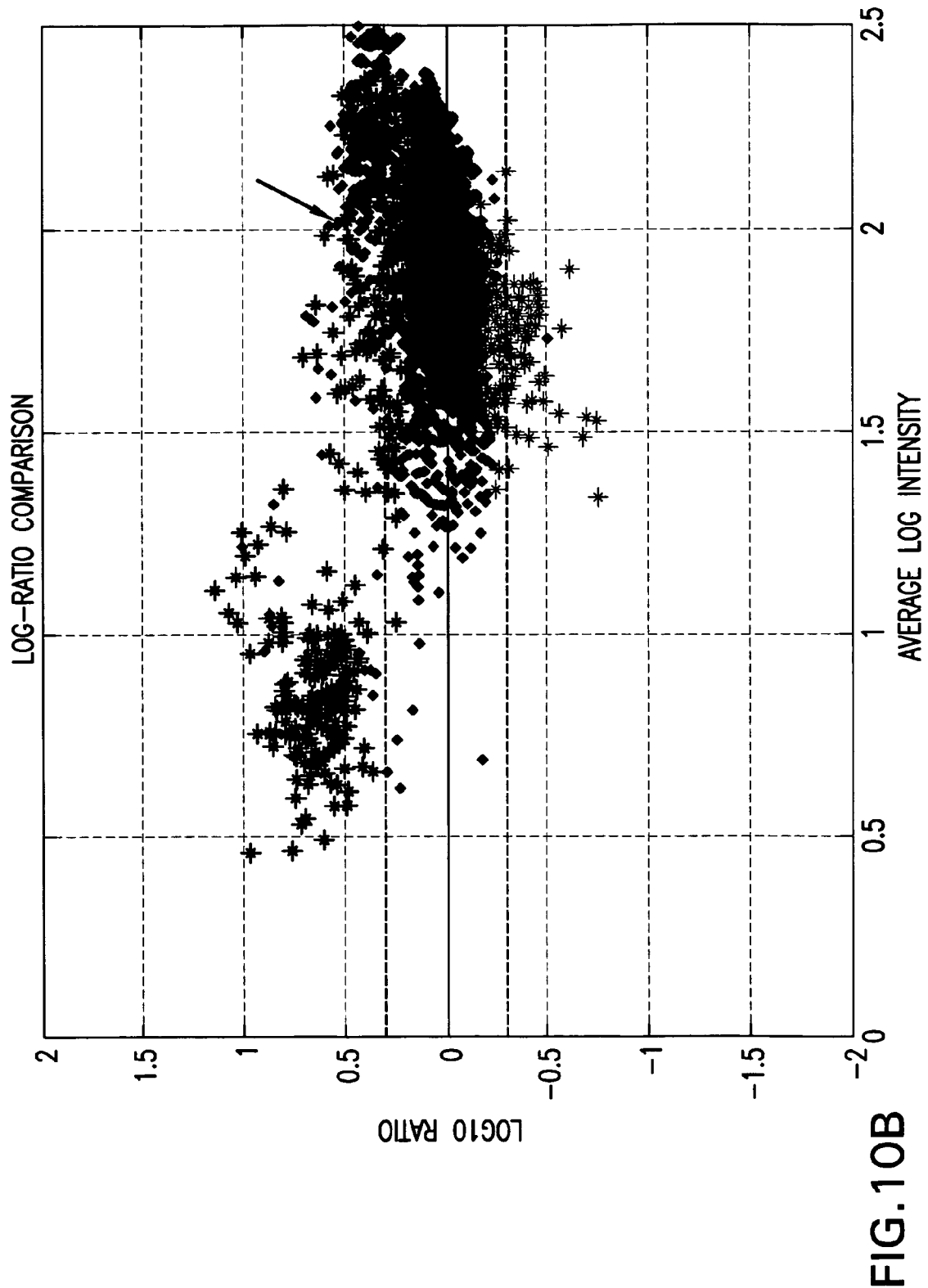

FIG. 10 shows an example of benefit from using the error model when the Luc reference is noisy; (a) four Luc wells in a high-drug (200 ug/ml cisplatin) plate are noisy, which cause significant up-biases of viabilities in other wells; (b) When comparing to no-drug, the affected data have high fold changes (the group of small dots above the dashed line, as indicated by the arrow), but are not called as changed due to their increased error estimation. (p-value<0.01). The statistically significant signatures shown are from the plates with consistent Luc measurements.

Figure 11:
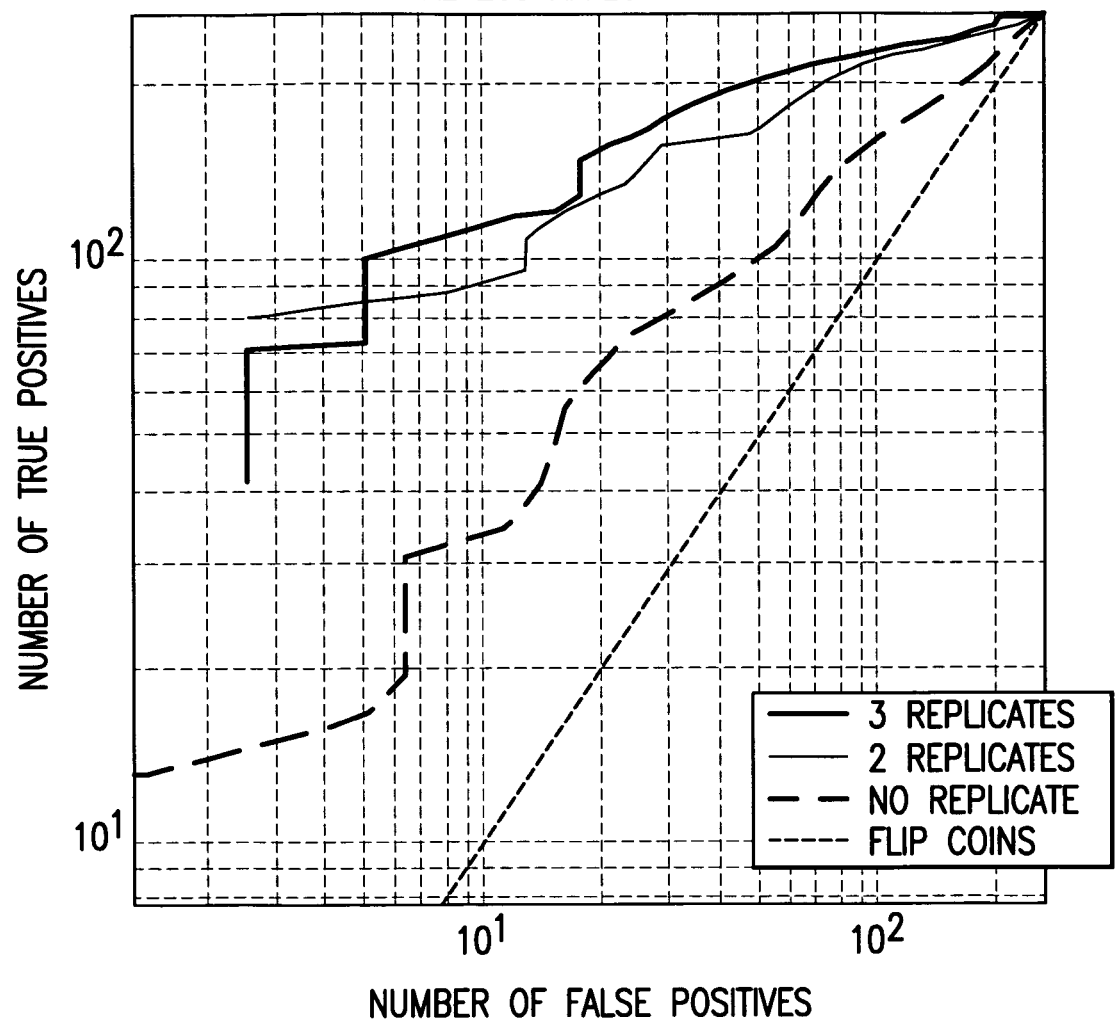

FIG. 11 shows ROC comparison of the detection power (sensitivity and specificity) using different numbers of replicate RNAi screens. A higher ROC curve indicates higher detection sensitivity for a given specificity.

FIG. 12 shows viability comparison histogram plots of same-versus-same non-control genes; (a) without normalization, the center of viability log-ratio distribution has a bias from zero; (b) with normalization, the bias is removed.

FIG. 13 shows ROC curves (a) without normalization; and (b) with normalization. After normalization the detection power (sensitivity at given specificity) is increased. In (b) the dashed line is based on the current method in-use where fold-change detection is applied without replicates and without normalization.

5. DETAILED DESCRIPTION OF THE INVENTION

The present invention provides methods for detecting variations in measurements of a biological variable under different conditions, e.g., variations in cell viability or variations in expression level of a nucleic acid species or in abundance or activity of a protein species under different conditions, e.g., with or without treatment of a drug, under the treatments of different drugs, or under different environmental conditions. In the methods of the invention, one or more measurements of a variable under the first condition, is compared with one or more measurements of the variable under the second condition. A metric of the difference between the measurements under the first condition and the measurements under the second condition is determined and used to represent the variation in the variable between the two conditions. The error of the metric is determined based on predetermined measurement errors of the measurements and deviations among the replicate measurements.

The inventor has discovered that in assays in which the number of replicate reference measurements is low, approximating the errors of the measurements by a propagated error based on a predetermined error and a scattered error provides a more accurate estimate of the errors, which, in turn, provides a more accurate estimate of the error of the difference metric. The difference metric and its error provide a good representation of the variation in the measurement of the biological variable and provide a good basis for comparison of variations in the biological variable among different conditions.

In a most used embodiment of the invention, a measurement of a variable, e.g., a measurement of the variable under one condition, is compared with a reference value obtained from one or more reference measurements. A metric of the difference between the measurement and the reference value, e.g., a ratio or an arithmetic difference, is determined and used to represent the deviation in the measurement of the variable. The error of the metric is determined based on a predetermined measurement error of the measurement and the error of the reference value. The reference value can be a mean of the one or more reference measurements. The error in the reference value is a sum of a propagated error based on predetermined measurement errors of the reference measurements and a scattered error based on the deviation of each reference from the reference mean.

In some embodiments of the invention, more than one replicate measurement is obtained for a variable. In such embodiments, a mean of the difference metric and the error of the mean of the difference metric can be determined. The error of the mean of the difference metric can be determined as a sum of a propagated error and a scattered error. The propagated error can be determined based on the errors for each difference metric including the corresponding reference error. The scattered error can be determined as the deviation of each difference metric from the mean of the difference metric.

The variations in measurements of a biological variable, e.g., viability of cells under a perturbation relative to cells under a normal condition, can be characterized by any convenient metric, e.g., arithmetic difference, ratio, log(ratio), etc. The mathematical operation log can be any logarithm operation. Preferably, it is the natural log or log10.

The mean of the measurements and/or the difference metrics can be a weighted mean, e.g., an error-weighted mean that is weighted by the error of each metric of difference. The known errors of the measurements and/or difference metrics indicate that some of the measurements and/or difference metrics have greater errors than others. It may be desirable to give them smaller weights in the calculation of the mean. This allows minimizing their impacts to the accuracy of the mean estimation.

In the invention, multiple biological variables of a particular sample, e.g., a particular type of cells, a cell sample under a particular condition or perturbation, such as exposure to a drug, a genetic mutation and so on, may be measured. The sample can be a single cell or a population of cells. In this application, a cell type refers to a particular type of cell, e.g., a type of cells that can be distinguished from other types of cells by one or more phenotypic and/or genotypic characteristics. For example, a cell type can be but is not limited to a particular cell line, e.g., a tumor cell line, a particular tissue type, e.g., liver cell, erythrocyte, etc. In this disclosure, a collection of measurements of one or more biological variables is also referred to as a profile. Each of the variables measured in a profile can be any measurable variable of the sample including but not limited to the expression or transcript level of a gene or abundance of a protein, level or concentration of a small cellular molecule, e.g., a metabolite, level or concentration of ions, e.g., $Ca^{2+}$, $Na^+$, and $K^+$, level of a clinical indicator, e.g., level or concentration of a chemical in blood or in a cell culture, a measure of cell health, a measure of interactions between molecules, e.g., binding of a molecule to a protein, a measure of a molecular event/process, a measure of activity of a protein or other molecule, etc. As an example, a profile of measurements may contain a set of gene expression levels of a biological sample which has undergone a particular drug treatment. Each of the measurements in a profile may be a relative measurement, i.e., a measurement relative to a reference value. The methods of the invention can be applied to one or more measurements in a profile.

The invention provides a method for comparing variations in measurements. Using the metric representing the variations of measurements of the variable, and its error, changes in measurements under different conditions are compared.

The present invention also provides methods for analyzing measurement data representing the effects of a set of different perturbations. The measurement data comprise measurements of a biological variable in a sample under each of the set of different perturbations, e.g., measured viability of cells having been subject to different drug perturbations. Measurement data of a biological variable A monitored on each of N samples can be represented as $\{A(k)\}$, k=1, 2, ..., N. Herein, for convenience, such a data set is often referred to as A. One or more references are associated with the set of measurements. Measurement of each sample can be compared with the references.

The invention is particularly useful in performing large scale interaction screening, e.g., screens of interactions between a drug and genes or gene products.

Figure 1:
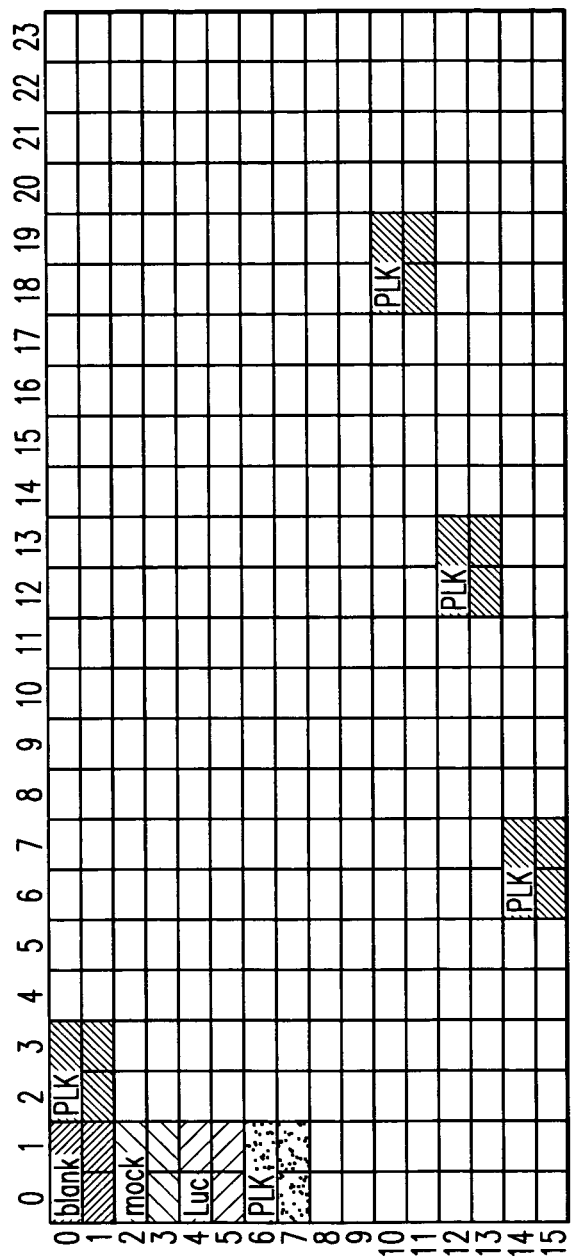
FIG. 1 is an illustration of an exemplary layout of a 384-well plate.
Figure 2:
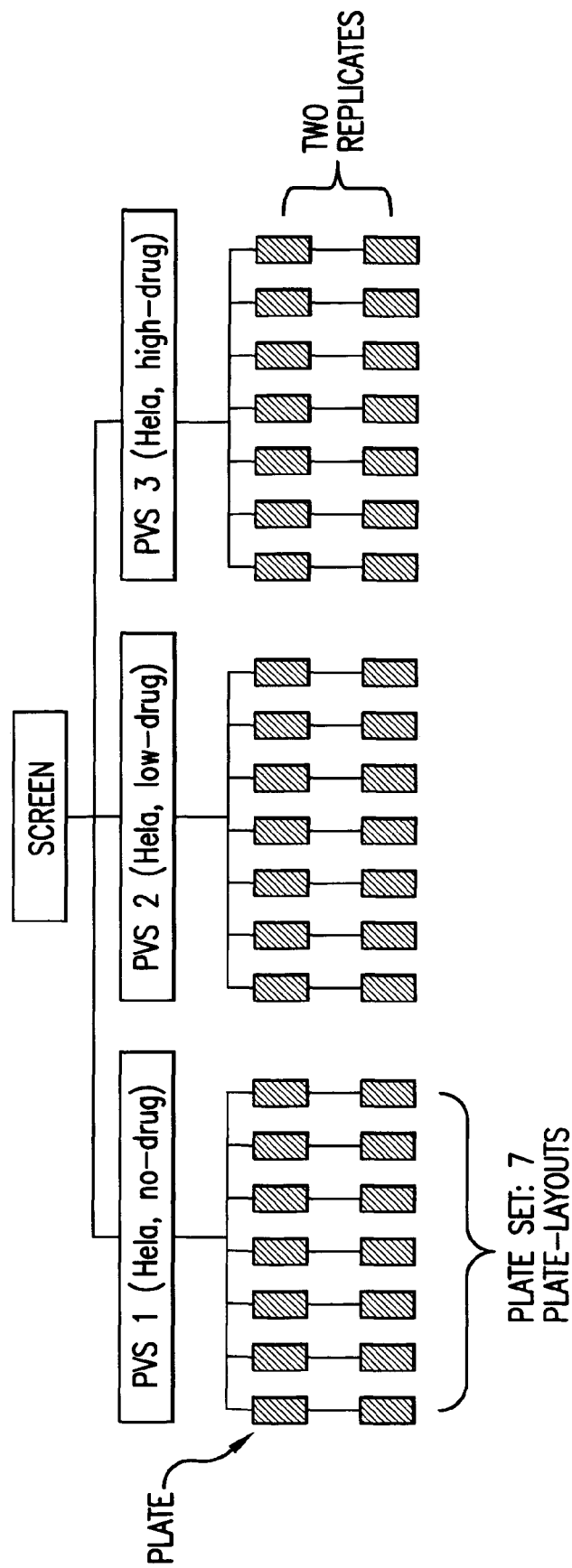
FIG. 2 shows an example of a screen.

As used herein, a layout refers to a particular arrangement of different samples in a parallel experiment, e.g., a particular arrangement of different samples among the wells of a plate. In this application, for simplicity reasons, the invention is often described with reference to the microtiter plate format of an experiment. It will be apparent to one skilled person in the art that the invention is also applicable to other types of parallel experiments and layouts. FIG. 1 shows an exemplary layout of a 384-well plate. For example, in the layout shown in FIG. 1, each well of the plate has assigned to it a cell sample subject to a particular siRNA targeting a particular gene. Thus, the plate shown in FIG. 1 is configured in such a manner that a plurality of different siRNA treated samples are assigned to different wells, with the identities of the siRNAs and their corresponding locations on a plate defined. As an example, in the layout shown in FIG. 1, several groups of 4 PLK siRNA wells located at various places across the plate are illustrated. When the number of different samples, e.g., the number of samples of cells of a cell type subject to different siRNAs, is larger than the number of wells on a plate, multiple plates, each having a particular layout can be used to assay the whole set of samples. For example, to assay a set of approximately 2,000 different cell samples, each having a different gene silenced by one or more siRNAs targeting the gene, a set of 7 386-well microtiter plates can be used (see, FIG. 2). Such a set of plates can be used for assaying the set of samples under different conditions, e.g., under different drugs and/or drug doses. A set of measurements under each condition is termed "a treatment group" or a PVS, such as no-drug, low-dose drug-treated, or high-dose drug-treated, etc. In some embodiments, two or more replicated plates are used for each treatment group. The collection of all measurements under different conditions is termed a "screen." Thus, a screen can contain several treatment groups. FIG. 2 shows an exemplary screen having three treatment groups, i.e., HeLa no-drug, HeLa low-dose drug-treated, and HeLa high-dose drug-treated, in a seven plate layouts with two replicates.

Measurements obtained from a plate for a condition can be viewed as a profile. To build an "experiment", multiple layouts are "stitched" together, e.g., different "profiles" are combined into a larger profile. Each data point in a screen corresponds to a measurement of a biological variable, e.g., a fluorescence intensity measurement. Thus, each data point can be identified by two indices, a plate index and a well index. For example, I_raw (i, j ) is used to designate the raw fluorescent intensity measurement in the ith well of the jth plate in a plate set. In the example shown in FIG. 2, i: 1-384, and j: 1-7. In each plate, a group of one or more replicate measurements of a particular type of sample may be assigned to different wells. Such a group of replicate measurements may be additionally designated. For example, in the exemplary layout shown in FIG. 1, there are 4 wells of Blank and 4 wells containing Luciferase ("Luc") treated sample. A Blank can be a sample which contains reagents, e.g., buffer, but does not contain any cells. Blanks can be used to determine the background. Measurements correspond to these wells are respectively designated as the BlankSet and the LucSet, with each well corresponding to Blank or Luc indexed for the set. Mock samples can also be included. A mock sample can be a sample which contains the cells under no perturbation, e.g., cells without siRNA.

As used herein, a "same-type" or "same vs. same" experiment is often referred to. As used herein, a same-type experiment refers to an experiment for which the two conditions are the same, e.g., C vs. C. In some embodiment, a same-type experiment contains data measured from a biological sample in a base-line state. As used herein, a "baseline state" refers to a state of a biological sample that is a reference or control state.

The methods of the invention can be applied to an experiment in which one reference value based on a set of one or more reference measurements is obtained for a plurality of different measurements, such as in a microtiter plate experiment. In such an experiment, a reference value is obtained for each plate and is used to determine the difference metric for all measurements obtained from the same plate. The methods can also be applied to a microarray experiment in which one or more control probes are used to normalize the measured intensities.

The methods of the invention can also be applied to an experiment in which paired measurements and references are involved, such as in a DNA microarray experiment. In such an experiment, each probe measurement has one or more corresponding reference measurements. The methods of the invention can be applied to each probe measurement and the associated reference measurements.

In this disclosure, the methods of the present invention are often described in terms of viability measurements in cell-based RNA interference and/or drug assays. It will be apparent to a person of ordinary skill in the art that the methods of the present invention are equally applicable to data measured in many other kinds of experiments, e.g., data measured in an ELISA assay, a kinase assay, or a DNA or protein microarray assay.

For simplicity, the methods of the present invention are often described in terms of fluorescence signals. It will be apparent to a person of ordinary skill in the art that the methods of the present invention are equally applicable to other types of measured data, e.g., colorimetric, luminescent, etc.

5.1. Biological Variables

The state of a cell or other biological sample can be characterized by one or more measurable biological variables. These variables may vary in response to perturbations, or under different conditions. As used herein, the term "biological sample" is broadly defined to include any cell, tissue, organ or multicellular organism. A biological sample can be derived, for example, from cell or tissue cultures in vitro. A biological sample can also be a sample containing one or more biologically or biochemically active molecular species.

The state of a biological sample can be measured by the content, activities or structures of its cellular constituents. The state of a biological sample, as used herein, is characterized by a collection of measurements of biological variables, which are used to characterize the cell or organism for an intended purpose, including, but not limited to characterizing the effects of a drug or other perturbation. The diversity of live cells and their environments often makes it desirable to combine several different measures to characterize the cells. For example, cell health can be characterized by enzymatic activity, membrane permeability and oxidation-reduction (redox) potential. Each assay method has inherent advantages and limitations and may introduce specific biases into the experiment; thus, different applications often call for different approaches. Thus, in preferred embodiments, a plurality of variables are monitored for a cell.

The biological variables can be the abundances (i.e., amounts or concentrations), activities, states of modification (e.g., phosphorylation) of molecular species in a cell. For example, biological variables of a biological sample (e.g., a cell or cell culture) which are of interest in the present invention include the identities and abundances of the constituent RNA species, especially mRNAs, in the cell under a given set of conditions. The identity and abundance of a RNA species can be conveniently determined by, e.g., measuring cDNA abundances by any of several existing gene expression technologies. One embodiment of the invention employs DNA arrays for measuring mRNA or transcript level of a gene. Types of biological variable of a biological sample of interest in the present invention also include the identities and abundances of the constituent protein species in a biological sample under a given set of conditions. Types of biological variable of a biological sample of interest in the present invention also include the activities of the constituent protein species (and also optionally catalytically active nucleic acid species) in the biological sample under a given set of conditions.

The biological variables can be other measurements relevant to the biology of a biological sample, such as cell viability, cell proliferation and various cellular processes, including but are not limited to apoptosis, cell adhesion, chemotaxis, multidrug resistance, endocytosis, secretion and signal transduction. Cell viability and cytotoxicity can be measured by enumerating the proportion of live and/or dead cells in a population. Cell proliferation assays can be measured by monitoring the growth rate of a cell population or to detect daughter cells in a growing population. Cell proliferation assays can also be measured by monitoring the numbers of adherent or nonadherent cells based on the presence of newly replicated DNA, the total nucleic acid content or the total protein content. Cell status and cellular processes may also be measured through monitoring the associated changes in intracellular radicals, free-ion concentrations, e.g., concentrations of $Ca^{2+}$, $N^+$, and $K^+$, and pH, or membrane potential.

The biological state of a biological sample (e.g., a cell or cell culture) can be represented by a profile of measurements of some number of biological variables. Such a profile of biological variables can be represented by the vector S: $S=[S_1, \ldots S_i, \ldots S_k]$, where $S_i$ is the measurement of the ith biological variable, for example, the transcript level of gene i, or alternatively, the abundance or activity level of protein i.

The responses of a biological sample to a perturbation, i.e., under a condition, such as the application of a drug, can be measured by observing the changes in the biological state of the biological sample. A response profile is a collection of changes in measurements of biological variables. Such changes can be monitored with various chemical and biological reagents, such as appropriately responsive fluorescent indicators. These processes can be monitored either in living cells or in fixed-cell preparations, and either on a single cell basis or on a cell population basis by, e.g., microscopy, flow cytometry, or a microplate reader. In some embodiments of the invention, the response is simply the difference between measurements of biological variables under the perturbation and measurements of the variables in a reference sample. In some preferred embodiments, the response is defined as the ratio of measurements of the variables under the perturbation and measurements of the variables in a reference sample. In the present invention, the response profile of a biological sample (e.g., a cell or cell culture) to the perturbation m can be described as the vector $v^{(m)}$: $v^{(m)}=[v_1^{(m)}, \ldots v_i^{(m)}, \ldots v_k^{(m)}]$, where $v_i^m$ is the value of measured change of the ith biological variable under the perturbation m. In one embodiment, the response profile contains measurements of variables characterizing cell viability.

The state of a biological sample may also include measurements of biological variables in more than one type of cells. In one embodiment, simultaneous multi-color measurements of numbers of live and dead cells are used to monitor the viability status of a mixed-cell population, e.g., following treatment by one or more drugs that have effects on one or more types of cells in the population.

In a preferred embodiment, fluorescence-based assays, e.g., fluorescence-based cell viability and proliferation assays, are used. Such fluorescence-based assays are generally less hazardous and less expensive than radioisotopic techniques, while more sensitive than calorimetric methods and more convenient than animal testing methods. A person skilled in the art will understand that in addition to cell-based assays, fluorescence-based assays are also widely used in kinase assays, immunoassays, e.g., ELISA, and DNA and protein arrays.

5.2. Methods of Determining Changes in Measurements

The present invention provides a method for detecting variations in measurements of a biological variable under different conditions based on one or more measurements of the variable under one condition and one or more measurements of the variable under another condition. In preferred embodiments, the second condition can be a reference condition against which the variations in measurements of the variable under the first condition are of interest. For example, the biological variable can be cell viability of cells of a cell type, and the variation of interest is the variation in cell viability in a cell subject to a drug treatment relative to a cell not subject to the drug. In preferred embodiments, the measurements of the variable under the first condition and the measurements of the variable under the reference condition are obtained in the same parallel experiment, e.g., measured on the same microtiter plate.

In one embodiment, a measurement x of a biological variable, e.g., a variable in a cell of a cell type, under the first condition is compared with a reference value obtained based on one or more reference measurements $\{y_i\}$ of the variable under the reference condition, where i=1, 2, ..., $n_r$, $n_r$ being the number of reference measurements. The reference value can be a reference mean $\bar{y}$ of the one or more reference measurements $\{y_i\}$. In preferred embodiments, the comparison is performed by determining a metric of difference between x and the reference mean $\bar{y}$. Any suitable metric of difference, e.g., arithmetic difference, e.g., x-$\bar{y}$; ratio, e.g., x/$\bar{y}$; or log(ratio), e.g., log(x/$\bar{y}$), can be used as the metric of difference. In a preferred embodiment, the metric of difference is the ratio of measurement x and the reference mean $\bar{y}$, e.g., x/$\bar{y}$.

In preferred embodiments, an error of the metric of difference is also determined. In a preferred embodiment, the error of the difference metric is determined based on a predetermined measurement error of x and a reference error $\sigma_y$ of the reference value, e.g., the reference mean $\bar{y}$. In a preferred embodiment, the reference error comprises a propagated reference error $\sigma_{y,p}$ and a scattered reference error $\sigma_{y,s}$. In one embodiment, the propagated error is determined based on predetermined experiment errors of the reference measurements, whereas the scattered error is determined based on deviation of each of the reference measurement with respect to the reference value, e.g., the reference mean.

In the present invention, a predetermined measurement error is often used in determining the measurement error and the reference error. As used herein, a "predetermined error" is an error that can be determined without using information gained from error analysis of the current measurement(s). For example, the predetermined error of a measurement can be a function of some parameters determined based on measured data which are obtained either prior to or concurrently but independently with the current measurements to be analyzed. The predetermined error can be a function of the measurement. In one embodiment, the predetermined error of a measurement of a variable is determined based on prior measurements of the same variable using the same measurement technological platform, e.g., prior measurements of fluorescence intensity of living cells of a cell type using the same measurement method. The predetermined error can be determined from such prior measurements using a suitable error model. In this disclosure, a predetermined measurement error is also referred to as a "prior," which is intended to encompass a predetermined error determined by any of the methods using any information about the error available but without error information gained from the current measurements. In one embodiment, the predetermined error of a measurement of a variable is an error that is determined prior to carrying out the methods of the invention.

In a preferred embodiment, a technology platform specific error model is used to determine the predetermined measurement error. Such estimated measurement error is used as a predetermined error or a "prior" in the error estimation. In a more preferred embodiment, the errors are estimated using an error model described in Section 5.4., infra. Preferably, the predetermined error comes from an application-specific error model, e.g., a two-term error model as described by Eq. 23. Based on the knowledge of data noise sources and training data, the error model provides an estimation of the measurement error in a measured quantity. Predetermined measurement error may contain errors from various sources, including sample preparation, labeling and dye related bias, sample variation, signal scanning and image feature extraction. Preferably, the predetermined measurement error sets the lower bound of the total variation in the measurement that includes biological variations. When the number of replicates is limited, the predetermined measurement error can be used as a "prior" in the error estimation. The predetermined measurement error thus provides additional information to obtain better error estimations. The improved error estimation can help increase the accuracy in detecting changes.

When replicate measurements are available, the predetermined error for each measurement can be "propagated" as a component of the total error in the mean of the replicate measurements. The propagated error is then combined with a scattered error to obtain an estimate of the total error. Preferably the propagated error and the scattered error are combined in such a manner that when the number of replicate measurements is small, the propagated error is dominant, whereas when the number of replicate measurements increases, the scattered error becomes more and more dominant, and when the number of replicate measurements becomes very large, the error approaches the scattered error. In a preferred embodiment, the propagated error and the scattered error are combined according to Eq. 1

$$\sigma = \frac{\sigma_p + (n-1) \cdot \sigma_s}{n} \quad (1)$$

where $\sigma_p$ and $\sigma_s$ represent the propagated error and the scattered error, respectively. For example, for the reference measurements described above, the total error of the reference mean can be determined using equation 1 by substituting $\sigma$ with $\sigma_y$, $\sigma_p$ with $\sigma_{y,p}$, $\sigma_s$ with $\sigma_{y,s}$, and n with $n_r$, respectively. For simple average of the reference meaurements, $\sigma_{y,p}$ and $\sigma_{y,s}$ can be determined according to Eqs. 2 and 3

$$\sigma_{y,p} = \frac{\sqrt{\sum_i \sigma_y^2(i)}}{n_r} \quad (2)$$

and $$\sigma_{y,s} = \underset{i \in 1, \ldots, n_r}{stdev(y_i)} \Big/ \sqrt{n_r} \quad (3)$$

where $\sigma_y^2(i)$ is a predetermined experiment error of measurement $y_i$.

In general, the predetermined experiment errors of measurement x and each reference measurement $y_i$ can be any errors that are determined based on each individual measurement. In preferred embodiments, the predetermined errors are determined according to an error model described in Section 5.4., infra. In one embodiment, the predetermined errors are determined according to a three term error model as described by Eq. (25). In another embodiment, the predetermined errors are determined according to a two term error model as described by Eq. (23).

In a preferred embodiment, the metric of difference is a ratio of measurement x and the reference value y: x/y. In this embodiment, the error of the metric is determined according to Eq. 4

$$\sigma_{ratio} = \sqrt{\sigma_{Logx}^2 + \sigma_{Logy}^2} \cdot \frac{x/y}{\text{Log}_{10}(e)} \quad (4)$$

where $$\sigma_{Logx} = \text{Log}_{10}(e) \cdot \frac{\sigma_x}{x} \quad (5)$$

and $$\sigma_{Logy} = \text{Log}_{10}(e) \cdot \frac{\sigma_y}{y} \quad (6)$$

In some embodiments of the invention, more than one replicate measurement $\{x_i\}$ of a biological variable are obtained, where $i=1, 2, \ldots, n_x$, $n_x$ being the number of said one or more replicate measurement. There can be one or more reference measurements associated with each measurement $x_i$. For example, viability of cells of a cell type subject to a drug can be measured along with one or more reference measurements in duplicate or triplicate. In such embodiments, a metric of difference $D_i$ between each measurement $x_i$ and a corresponding reference value, e.g., a reference mean $\bar{y}(i)$, of one or more reference measurements of the variable associated with measurement $x_i$ but under the reference condition, and its associated error $\sigma_D(i)$ can be determined using a method described supra. The error can be used as the predetermined error of the difference $D_i$ since it does not depend on any replicates of $D_i$. A mean of the metrics of difference is then preferably obtained. The error of the mean of the difference metric can be determined as a sum of a propagated error and a scattered error. The propagated error can be determined based on the errors for each difference metric including the corresponding reference error, i.e., the predetermined error. The scattered error can be determined as the deviation of each difference metric from the mean of the difference metric. A mean of the difference metric, $\bar{D}$, and the error of $\bar{D}$ can then be determined and used to represent the detected variation.

In one embodiment, for each measurement $x_i$, a set of reference measurements $\{y_j(i)\}$ is used to determine the corresponding reference mean $\bar{y}(i)$, where $j=1, 2, \ldots, n_y(i)$, $n_y(i)$ being the number of reference measurements associated with measurement $x_i$. As used herein, reference measurements associated with measurement $x_i$ means that the reference measurements are made in connection with measurement $x_i$, e.g., measured in different wells on the same microtiter plate. The predetermined error associated with difference metric $D_i$, $\sigma_D(i)$, is determined based on a predetermined experiment error $\sigma_x(i)$ of measurement $x_i$ and a reference error $\sigma_y(i)$ of reference mean $\bar{y}(i)$. The reference error comprises a propagated error $\sigma_{y,p}(i)$ and a scattered error $\sigma_{y,s}(i)$. The propagated error is determined based on predetermined experiment errors of the reference measurements $\{y_j(i)\}$, and the scattered error is determined based on deviation of each of the reference measurement $y_j(i)$ with respect to the reference mean $\bar{y}(i)$. In a preferred embodiment, the metric of difference is a ratio of measurement $x_i$ and the reference mean $\bar{y}(i)$: $x_i/\bar{y}(i)$. In this embodiment, the error of each difference metric can be determined according to Eqs. 4-6.

In one embodiment, the mean of the difference metric $\bar{D}$ is a simple average of the set of difference metrics $\{D_i\}$. In another embodiment, the mean of the difference metric $\bar{D}$ is a weighted mean of the set of difference metrics $\{D_i\}$ according to Eq. 7

$$\bar{D} = \frac{\sum_i w_i D(i)}{\sum_i w_i} \quad (7)$$

where $\omega_i$ is a weight of $D_i$.

Any suitable weighting scheme can be used to weight the difference metrics. In a preferred embodiment, the weight for the ith difference metric $D_i$ is determined according to Eq. 8

$$w_i = \frac{1}{\sigma_D^2(i)} \quad (8)$$

where $\sigma_D(i)$ is the predetermined error associated with the difference metric $D_i$ described above. In a preferred embodiment, $\sigma_D(i)$ is determined based on a predetermined experiment error $\sigma_x(i)$ of measurement $x_i$ and a reference error $\sigma_y(i)$ of the reference mean $\bar{y}(i)$.

In a preferred embodiment, the error of the mean of the difference metric $\bar{D}$, $\sigma_{\bar{D}}$, is also determined. In one embodiment, $\sigma_{\bar{D}}$ comprises a propagated error $\sigma_{\bar{D},p}$ and a scattered error $\sigma_{\bar{D},s}$. In a preferred embodiment, the propagated error $\sigma_{\bar{D},p}$ is determined based on the set of predetermined errors of the difference metric $\{\sigma_D(i)\}$, and the scattered error is determined based on deviation of each of the metric of difference $D_i$ with respect to the mean of the metric of difference $\bar{D}$. In one embodiment, $\sigma_{\bar{D}}$ is determined using the propagated error $\sigma_{\bar{D},p}$ and the scattered error $\sigma_{\bar{D},s}$ according to Eq. 1. In embodiments a weighted mean of the difference metric is used, $\sigma_{\bar{D}}$ can be determined based on a propagated error $\sigma_{\bar{D},p}$ and a scattered error $\sigma_{\bar{D},s}$ determined respectively according to Eqs. 9 and 10

$$\sigma_{\bar{D},p}^2 = \frac{1}{\sum_i w_i} \quad (9)$$

and $$\sigma_{\bar{D},s}^2 = \frac{1}{(n_x - 1) \cdot \sum_i w_i} \cdot \sum_i w_i \cdot [D(i) - \bar{D}]^2 \quad (10)$$

In another embodiment, one or more replicate measurements of a biological variable are performed along with one or more reference measurements in the same parallel experiment. For example, two or more wells in a microtiter plate may contained replicate samples. In such an embodiment, respective means can be determined for the one or more replicate measurements and the one or more reference measurements separately. A difference metric between the mean of the measurements and the mean of the reference measurement and its associated error can then be determined and used to represent the detected variation.

In a specific embodiment, a mean $\bar{x}$ of the one or more measurements $\{x_i\}$ of a variable under a particular condition, where $i=1, 2, \ldots, n_x$, $n_x$ being the number of the measurements, is determined. An error $\sigma_{\bar{x}}$ of the mean $\bar{x}$ is then determined. In a preferred embodiment, the error comprises a propagated error $\sigma_{x,p}(i)$ and a scattered error $\sigma_{x,s}(i)$. The propagated error is determined based on predetermined experiment errors of said one or more measurements $\{x_i\}$, and the scattered error is determined based on deviation of each of said measurement $x_i$ with respect to said mean $\bar{x}$. A metric of difference D between this mean $\bar{x}$ and a reference mean $\bar{y}$ is then determined. The reference mean $\bar{y}$ is a mean of one or more reference measurements $\{y_j\}$ of the variable under the reference condition, where $j=1, 2, \ldots, n_y$, $n_y$ being the number of reference measurements. The error $\sigma_D$ for the metric of difference D is determined based on $\sigma_{\bar{x}}$ and a reference error $\sigma_{\bar{y}}$ comprising a propagated error $\sigma_{y,p}$ and a scattered error $\sigma_{y,x}$. The propagated error is determined based on predetermined experiment errors of the reference measurements $\{y_j\}$, and the scattered error is determined based on deviation of each of said reference measurement $y_j$ with respect to said reference mean $\bar{y}$.

The mean $\bar{x}$ and the reference mean $\bar{y}$ can be simple averages or weighted means. In one embodiment, the mean $\bar{x}$ and the reference mean $\bar{y}$ are weighted means determined according to Eqs. 11 and 12

$$\bar{x} = \frac{\sum_i w_{x,i} x_i}{\sum_i w_{x,i}} \quad (11)$$

and $$\bar{y} = \frac{\sum_j w_{y,j} y_j}{\sum_j w_{y,j}} \quad (12)$$

where $$w_{x,i} = \frac{1}{\sigma_x^2(i)}$$

and $$w_{y,j} = \frac{1}{\sigma_y^2(j)},$$

and where the propagated errors $\sigma_{x,p}$ and $\sigma_{y,p}$ are determined according to Eqs. 13 and 14

$$\sigma_{x,p}^2 = \frac{1}{\sum_i w_{x,i}} \quad (13)$$

and $$\sigma_{y,p}^2 = \frac{1}{\sum_j w_{y,j}} \quad (14)$$

and the scattered errors $\sigma_{x,s}$ and $\sigma_{y,s}$ are determined according to Eqs. 15 and 16

$$\sigma_{x,s}^2 = \frac{1}{(n_x - 1) \cdot \sum_i w_{x,i}} \cdot \sum_i w_{x,i} \cdot (x_i - \bar{x})^2 \quad (15)$$

and $$\sigma_{y,s}^2 = \frac{1}{(n_y - 1) \cdot \sum_j w_{y,j}} \cdot \sum_j w_{y,j} \cdot (y_j - \bar{y})^2 \quad (16)$$

The invention also provides methods for comparing variations detected under difference conditions based on the measure of the variations. For example, comparison of changes in cell viability in cells under different conditions, e.g., subject to a drug treatment relative to a cell not subject to the drug or subject to treatments of different types and/or doses of drugs, is often of great importance in drug discovery. In the methods of the present invention, variations and their associated errors representing such changes as obtained by any method described above are used to accurately compare such changes.

In a preferred embodiment, changes in measurements of a biological variable under two different conditions are represented by $\{z_1, \sigma_1\}$ and $\{z_2, \sigma_2\}$, respectively. Herein, $z_1$ and $z_2$ represent respectively variations detected in the measurements under the first and the second condition, and $\sigma_1$ and $\sigma_2$ represent respectively the associated errors of $z_1$ and $z_2$. For example, $z_1$ and $z_2$ can each be a difference metric determined according to a method described above. In one embodiment, the comparison is carried out by a method comprising determining a parameter xdev according to Eq. 17

$$xdev = \frac{z_1 - z_2}{\sqrt{\sigma_1^2 + \sigma_2^2}} \quad (17)$$

In another embodiment, the method also comprises determining a p-value for the parameter xdev according to Eq. 18

$$p\text{-value} = 2 \cdot Erf(|xdev|) \quad (18)$$

The xdev and p-value are then used as quantitative measures of the comparison.

In another embodiment, the method further comprises determining a log ratio according to Eq. 19

$$lratio = \log_{10}(z_1/z_2) \quad (19)$$

and an error of the log ratio according to Eq. 20

$$\sigma_{lratio} = \left| \frac{lratio}{xdev} \right| \quad (20)$$

The lratio and $\sigma_{lratio}$ can also be used as quantitative measures of the comparison.

In embodiments where more than one replicate measurement of a variable are obtained for each condition, the changes in measurements of a biological variable under different conditions can be represented by groups of detected variations and their associated errors: $\{z_1(i), \sigma_1(i), i=1, 2, \ldots, n_1\}$, $\{z_2(j), \sigma_2(j), j=1, 2, \ldots, n_2\}, \ldots$, respectively, where $n_1, n_2, \ldots$, designate the number of measurements in each group. Each detected variation $z_1(i)$ and its associated error $\sigma_1(i)$ can be obtained by a method described above. For example, each $z_1(i)$ can be a weighted difference metric determined according to Eqs. 7.

In another embodiment, the groups of detected variations and their associated errors are compared using the improved ANOVA method disclosed in U.S. Patent Application Publication No. 2004-0143399, published on Jul. 22, 2004, which is incorporated herein by reference in its entirety.

In another embodiment, the changes in measurements of a biological variable under different conditions are represented by the means of detected variations and the associated errors: $\{z_1, \sigma_1\}, \{z_2, \sigma_2\}, \ldots$ For example, each $z_1$ and $\sigma_1$ can be the mean of the difference metric $\bar{D}$ and its error $\sigma_D$ as described above. The changes in measurements can be compared by comparing variations under different pair of conditions by the xdev method described above (see, e.g., Eqs. 17-20).

In one embodiment, a change in measurements of a biological variable under two different conditions is identified if the fold-change is above a cutoff value, e.g., >2 fold cutoff. Preferably, the fold-change threshold is adjusted based on number of replicates. In one embodiment, when the number of replicates is smaller, the threshold should be higher, because more false positives are detected at a given fold change cutoff if no/few replicates are available. Such adjustment may be difficult and impractical in certain cases because it is often not known how many false positives there will be for any combination of the fold-change threshold and the number of replicates.

In a preferred embodiment, a statistically significant change in measurements of a biological variable under two different conditions is identified if the p-value is within a given p-value threshold (e.g. <0.01). The threshold of the p-value can be chosen based on various factors, including desired false positive rate. Such a p-value based method does not depend on number of replicates. Thus, a p-value threshold can be used for different number of replicates.

In another preferred embodiment, a statistically significant change in measurements of a biological variable under two different conditions is identified if the fold-change is above a cutoff value, e.g., >2 fold cutoff, and the p-value is within a given p-value threshold, e.g. <0.01.

5.3. Methods of Analyzing High-Throughput Screens

A high-throughput screen, e.g., assays of a plurality of samples conducted in paralled, is herein called a "screen". Each screen may contain several sets of measurements, each set containing measurements of a plurality of samples under a particular condition. As an example, an siRNA screen can contain several treatment groups of a plurality of different cells each having a different gene silenced by an siRNA. Each treatment group comprises the plurality of cells under one treatment, such as no-drug, low-dose drug-treated, or high-dose drug-treated). Each treatment group is also called a PVS. Each set under a particular condition can be performed in one or more parallel experimental runs, e.g., one or more 384-well plates. Each plate can have a unique layout (pattern). FIG. 1 is an example of a layout. Each plate can comprise one or more wells of blanks. Each plate can also comprise one or more wells for each of one or more other types of controls, e.g., mock. There can be several plate layouts (e.g., 7) in each screen to cover a large number of samples, e.g., a large number of different genes. The same set of layouts is applied to all treatment groups in the screen. Replicated plates can also be included in each layout in each treatment group. FIG. 2 illustrates an example of a screen. In this example of screen, there are three treatment groups, seven plate layouts, and two replicates. There are a total of forty-two 384-well plates used in this screen. Each plate provides 384 raw-intensity measurements. Each plate can be viewed as a profile.

To build an "experiment", multiple layouts can be "stitched" together. In one embodiment, multiple layouts are stitched by merging the profiles of measurements into a larger profile. In one embodiment, a total of J profiles are obtained in J runs. The jth profile, e.g., obtained in the jth plate, can be represented by the vector $I_j$: $I_j = [I_j(1), \ldots I_j(i), \ldots I_j(K)]$, where $I_j(i)$ is the ith measurement in the jth profile. The profiles for different runs can then be stitched together into a single profile I: $I = [I_1(1), \ldots I_1(i), \ldots I_1(K); \ldots, I_j(1), \ldots I_j(i), \ldots I_J(K); \ldots]$. $I_j(i)$ can be a measurement x of a variable, or a reference measurement y of Section 5.2.

The methods described in Section 5.2 can be applied to the larger profile to determine an appropriate difference metric $\vec{z}$ and the associated error $\vec{\sigma}$, $\vec{z} = [z_1(1), \ldots z_1(i), \ldots z_1(K); \ldots, z_j(1), \ldots z_j(i), \ldots z_j(K); \ldots]$ and $\vec{\sigma} = [\sigma_1(1), \ldots \sigma_1(i), \ldots \sigma_1(K); \ldots, \sigma_j(1), \ldots \sigma_j(i), \ldots \sigma_j(K); \ldots]$ are then built from the experiments.

The replicates can also be combined. In the example shown in FIG. 2, three viability ("intensity") experiments (PVS1, PVS2 and PVS3) are carried out.

In some embodiments, a step of preprocessing is used to remove certain systematic biases. In one embodiment, background subtraction is used to remove the systematic additive-bias in each plate. In one embodiment, the background level for the jth profile is estimated as the median of intensity measurements in the blanks:

$$bkg(j) = \underset{l \in BlankSet}{MEDIAN}(I_j(l)) \qquad (21)$$

The background-subtracted measurement of the ith measurement in the jth profile can be determined as:

$$I_j(i) = I_j(i) - bkg(j) \qquad (22)$$

In one embodiment, to avoid negative intensities, the intensity in Equation 22 is set to one if it is less than one.

In one embodiment, to develop an error model, the error of the background, i.e., the error that is subtracted from raw intensities in Equation 22, is first determined. The error of the background is estimated as the standard deviation of the blanks:

$$\sigma_{bkg}(i) = \underset{l \in BlankSet}{STDEV}(I_j(l)) \qquad (23)$$

$\sigma_{bkg}(i)$ is then used to calculate errors using the error model according to Eq. 28 or Eq. 30, infra.

In a preferred embodiment, metrics of changes obtained by the methods described in Section 5.2 are normalized using all or a portion of the obtained metrics of change of control samples, e.g., mock or reference under the same condition to reduce or remove errors in obtained changes of measurements. In one embodiment, an average of all of the obtained metrics of changes under the same conditions is determined, and each individual metric of changes are normalized with the average. In this embodiment, the average is calculated according to $$\bar{z} = \frac{\sum_{j}^{J} \sum_{l \in control}^{L_j} z_j(l)}{\sum_{j}^{J} L_j} \qquad (24)$$

where $L_j$ is the number of control samples in the jth profile, e.g., profile obtained using the jth plate. Each data point of z is then normalized according to $$\bar{z}_j(i) = \frac{z_j(i)}{\bar{z}} \qquad (25)$$

In another embodiment, normalization is performed on measurements of the biological variable before determination of the metrics of changes. An average of all or a portion of the measurements under each same condition is determined, and each individual measurement is normalized with the average. Appropriate metrics of changes are then determined using the normalized measurements according to a method described in this section.

5.4. Error Models

Measured data obtained in an experiment often contain errors due both to the inherent fluctuation of the biological variable and to measurement errors from various external sources. The many sources of measurement error that may occur in a measured signal include those that fall into three categories—additive error, multiplicative error, and Poisson error. The signal magnitude-independent or intensity-independent additive error includes errors resulted from, e.g., background fluctuation, or spot-to-spot variations in signal intensity among negative control spots, etc. The signal magnitude-dependent or intensity-dependent multiplicative error, which is assumed to be directly proportional to the signal intensity, includes errors resulted from, e.g., the scatter observed for ratios that should be unity. The multiplicative error is also termed fractional error. The third type of error is a result of variation in the efficiency in labeling of a biological variable for observation. This type of error can depend on the square-root of the signal magnitude, e.g., measured intensity. For example, it can be a Poisson error, if the number of labels in a sample follows a Poisson distribution, and has a variance which is proportional to the average number of labels. A Poisson error also occurs as a result of variation in number of available binding sites in a microarray spot, because the number of binding sites on a microarray spot follows a Poisson distribution, and has a variance which is proportional to the average number of binding sites. Additional error terms can also be included, dependent on the particular measurement methodology and/or biological variable.

Errors in measured data can be described by error models (see, e.g., Supplementary material to Roberts et al, 2000, Science, 287:873-880; and Rocke et al., 2001, J. Computational Biology 8:557-569). In preferred embodiments, an error model (see, e.g., Supplementary material to Roberts et al, 2000, Science, 287:873-880; and Rocke et al., 2001, J. Computational Biology 8:557-569) contains two or three error terms to describe the dominant error sources. In a two-term error model, a first error term is used to describe the low-level additive error which comes from, e.g., the background of the array chip. Since this additive error has a constant variance, in this disclosure, it is also called the constant error. The constant error is independent from the hybridization levels of individual spots on a microarray. It may come from scanner electronics noise and/or fluorescence due to nonspecific labeling or nonspecific binding of fluorescence molecules to, e.g, the surface of a microarray or microtiter well. In one embodiment, this constant additive error is taken to have a normal distribution with a mean bkg and a standard deviation $\sigma_{bkg}$. After background level subtraction, which is typically applied in microarray data processing, the additive mean bkg becomes zero. In this disclosure, it is often assumed that the background intensity offset has been corrected. An ordinary skilled artisan in the art will appreciate that in cases where the background mean is not corrected, the methods of the invention can be used with an additional step of making such a correction.

The second error source is the multiplicative error that can be, for example, the combined result of the speckle noise inherent in the coherent laser scanner and the fluorescence dye related noise. The multiplicative error is also called fractional error because its level is directly proportional to the magnitude of the measured signal, e.g., the measured intensity level. It is the dominant error source at high intensity levels. In one embodiment in which the measured signal is obtained from a microarray experiment, the standard deviation of the fractional error in the k'th spot can be approximated as $$\sigma_{frac}(k) \approx a \cdot x(k) \quad (26)$$

where x(k) is the measured intensity in the k'th spot. The constant a in Equation 26 is termed fractional error coefficient, and describes the proportion of the fractional error to the intensity of the measured signal. In one embodiment, the constant has a value in the range of 0.1 to 0.2. In another embodiment, for cell viability assays, the constant is chosen to be 0.25. This constant may vary depending on the particular measurement methodology used for obtaining the measured signal and/or the particular hybridization protocol used in the measurement. In one embodiment, parameter a is determined during the error building phase by measuring the variance of the log ratio near the high intensity side in a same-vs.-same ratio experiment where the intensities in the ratio numerator and denominator come from the same sample and treatment. At high intensities, the variance of log ratio $x_1$ over $x_2$ relates to parameter a:

$$\text{Var}\{\ln(x_1/x_2)\} \approx \frac{(a \cdot x_1)^2}{x_1^2} + \frac{(a \cdot x_2)^2}{x_2^2} = 2 \cdot a^2 \quad (27)$$

when $x_1$ and $x_2 \gg \sigma_{bkg}$. In one embodiment, $x_1$ and $x_2$ are at least 4, 10, 50, 100, or 200 times $\sigma_{bkg}$.

In a two-term error model, the measurement error in a measured signal, e.g., measured intensity, x(k), can be defined as $$\sigma_x(k) = \sqrt{\sigma_{bkg}(k)^2 + \sigma_{frac}(k)^2} \approx \sqrt{\sigma_{bkg}(k)^2 + a^2 \cdot x(k)^2} \quad (28)$$

In a preferred embodiment of the invention, the background noise variances in Equation 28 are taken as slightly different in different microarray spots or regions of a microarray chip. In one embodiment, the difference is less than 20%, 10%, 5%, or 1%. In one embodiment, the background noise variances are determined based on measurements of blank control samples.

In a three-term error model, an extra square-root term is included to describe measurement errors originated from variation in the number of available binding sites in a microarray spot or in number of labels among different wells. In one embodiment, a term proportional to the measured intensity is used to provide an estimate of the average number of binding sites or number of label molecules when actual number of binding sites in microarray spot or actual number of label molecules in a well is not known. The term is also called the Poisson term. In such an embodiment, the Poisson error can be approximated as $$\sigma_{Poisson}(k) \approx b \cdot \sqrt{x(k)} \quad (29)$$

where parameter b is an overall proportional factor, termed Poisson error coefficient. In a three-term error model, the measurement error in a measured signal, e.g, a measured fluorescence intensity, x(k) can be defined as $$\sigma_x(k) = \sqrt{\sigma_{bkg}(k)^2 + \sigma_{Poisson}(k)^2 + \sigma_{frac}(k)^2} \quad (30)$$

-continued $$\approx \sqrt{\sigma_{bkg}(k)^2 + b^2 \cdot x(k) + a^2 \cdot x(k)^2}$$

In a preferred embodiment, during error model development, when $\sigma_{bkg}$ and parameter a have been determined, parameter b in Equation 30 is determined by measuring the intensity variance in the middle intensity ranges of the same-vs.-same experiments. In one embodiment, the intensity variance is measured in the 25 to 75 percentile range, 35 to 65 percentile range, or 45 to 50 percentile range for determination of b.

In a preferred embodiment, after the error model development phase, parameters a and b are fixed for an error model under a given microarray technology and experiment protocol. The background noise $\sigma_{bkg}$ can be estimated for each particular microarray experiment. In another preferred embodiment, when a set of replicate experiments are carried out, the background noise $\sigma_{bkg}$ for the set can be obtained by averaging the background noise estimated for each of the replicate experiments.

The two-term error model as described by Equation 28 can been seen as a simplified version of the three-term error model described by Equation 30 by setting the Poisson parameter b to zero. In this disclosure, Equation 28 is used as the general mathematical description of error models. It will be apparent to an ordinarily skilled artisan that any results obtained based on Equation 30 are also applicable to a two-term error model by setting the Poisson parameter b to zero.

It will be apparent to an ordinarily skilled artisan that other methods may also be used to determine an error model (see, e.g., Rocke et al., 2001, J. Computational Biology 8:557-569).

5.5. Intensity Transformations

The methods of the invention can be applied to transformed measurements.

5.5.1. Error Model Based Transformations

In a preferred embodiment, measured data are first transformed by an error model based transformation before analyzed by the improved ANOVA method of the invention. The results from the ANOVA analysis can be transformed back by an appropriate inverse transformation. An error model based data transformation method is described in U.S. Patent Application Publication No.2003-0226098, published on Dec. 4, 2003, which is incorporated by reference herewith in its entirety.

It is clear from Equation 30 that microarray intensity measurements do not meet the constant-variance requirement. There are different measurement errors (or variances) in different intensities. The intensity error is a function of intensity itself. To overcome this problem, a function f( ) is needed to transform measured data, e.g. the intensity data, x to a new domain y in which the variance becomes a constant. All analysis and data processing can then be carried out in the transformed domain. In a preferred embodiment, such a transformation is described as $$y(k)=f(x(k)), \text{ for all } x \text{ and} \tag{31}$$

$$\sigma_y(k) \approx C, \text{ for all } x \text{ where } C \text{ is a constant.} \tag{32}$$

Preferably the transformation works for both positive and negative (e.g, negative signals obtained after background subtraction) x. More preferably the transformation meets the following additional constraints:

(i) Monotonic: If $x(k1)>x(k2)$, then $y(k1)>y(k2)$ for all x;

(ii) Zero intercept: $f(0)=0$; and (iii) Smooth: The first and the second derivatives of the function f should be continuous functions.

Still more preferably, an inverse transformation function g exists so that the transformed data in the transformed domain can be transformed back to the original domain. The inverse transformation does the following operation:

$$x(k)=g(y(k)), \text{ for all } y \tag{33}$$

Preferably, the inverse transformation function g meets above four constraints as well. In one embodiment, the error in the inversely transformed intensity can be determined when the first derivative f'( ) of the forward transformation function f is available:

$$\sigma_x(k) \approx \frac{\sigma_y(k)}{df(x(k))/dx(k)} = \frac{\sigma_y(k)}{f'(x(k))} \tag{34}$$

It is most preferable that the forward transformation function f, its first derivative f', and the inverse transformation function g are all in analytical closed-forms.

In one embodiment, a transformation based on an error model is provided and used to transform measured data obtained in an experiment to a transformed domain such that the measurement errors in transformed data are equal to the measurement errors in the measured data normalized by errors determined based on an error model. As used in this disclosure, such an measurement error, i.e., a measurement error which equals the measurement error in the measured signal normalized by an error determined based on an error model, is also referred to as a normalized error. Any suitable error model can be used in the invention. In a preferred embodiment, the error model is a two-term or a three-term error model described in Section 5.4. In a particularly preferred embodiment, the variance of the transformed data in the transformed domain is close to a constant. More preferably, the transformation meets all requirements discussed in Section 5.4. The basic concept of the new transformation method is to apply an error model to normalize errors in real measurements, e.g., standard deviations in measured data, such that the normalized errors are close to a constant. Then a transformation function f( ) is found by the integration of the normalization function. The methods are applicable to any set of measured data whose errors can be described by a particular error model.

In a specific embodiment, the real measurement standard deviation $\Delta x$ is for the positive intensity $x>0$. The real standard deviation $\Delta x$ is usually known before the transformation. An error model in Equation 30 provides $\sigma_x$ that is an estimate of the real standard deviation $\Delta x$ for different intensities. In one embodiment, $\Delta x$ is an error determined by the experiment. In another embodiment, $\Delta x$ is calculated using an error model of the experiment. In a preferred embodiment, $\Delta x$ is chosen to be the larger of an experimentally determined error or an error model-calculated error. Assuming the transformed standard deviation is $\Delta y$, the following approximation relates the two errors with the first derivative function of the transformation:

$$f'(x) = \frac{dy}{dx} \approx \frac{\Delta y}{\Delta x} \quad (35)$$

If the equation is rearranged, one obtains $$\Delta y \approx \Delta x \cdot f'(x) \quad (36)$$

Because Equation 30 is an approximation of $\Delta x$, if a normalization function y' is defined as follows:

$$y' = f'(x) = \frac{1}{\sqrt{c^2 + b^2 \cdot x + a^2 \cdot x^2}}, \quad \text{for } x > 0, \quad (37)$$

where a, b, and c are defined as in Section 5.4., one can expect that the variance of y is close to a constant.

Equation 37 provides an analytical form of the first derivative function of the desired transformation. To obtain the transformation function itself, both sides of Equation 37 are integrated:

$$y = f(x) = \int f'(x) \cdot dx = \int \frac{dx}{\sqrt{c^2 + b^2 \cdot x + a^2 \cdot x^2}}, \quad \text{for } x > 0 \quad (38)$$

The integral in Equation 38 does have an analytical solution. The solution is described by equation $$y = f(x) = \frac{\ln\left(\frac{b^2 + 2 \cdot a^2 \cdot x}{a} + 2 \cdot \sqrt{c^2 + b^2 \cdot x + a^2 \cdot x^2}\right)}{a} + d, \quad (39)$$

for $x > 0$

Applying the zero intercept constraint (ii) in Section 5.4., i.e., y=0 when x=0, the constant d in Equation 39 is found to be $$d = \frac{-\ln\left(\frac{b^2}{a} + 2 \cdot c\right)}{a} \quad (40)$$

As indicated in Equation 33 in Section 5.5.1., preferably one finds the inverse transformation function g(y) so that the transformed intensity y can be converted back to the original x scale whenever necessary. By using linear algebra or a symbolic-solution software, such as Maple, one finds $$x = g(y) \quad (41)$$

$$= \frac{-(4 \cdot a^2 \cdot c^2 - a^2 \cdot e^{2a \cdot (y-d)} + 2 \cdot a \cdot b^2 \cdot e^{a \cdot (y-d)} - b^4)}{4 \cdot a^3 \cdot e^{a \cdot (y-d)}}, \quad \text{for } y > 0$$

To complete the forward and the inverse transformation pair for both intensity and its error, the standard deviation of the inversely transformed intensity can be estimated by using Equation 34.

In a specific embodiment, the transformation function can be further defined to be symmetric to zero for all x. When x<0, the absolute value |x| is used to replace x in the forward transformation in Equation 39 and to give a negative sign to the result y. In the inverse transformation in Equation 41, when y<0, the absolute value |y| is used to replace y and to give a negative sign to the result x. Under the forward transformation, the estimated transformed error $\sigma_y$ is one over all intensity ranges of x or y, so that constant C=1 in Equation 32. The transformation also meets all other requirements and constraints described above. In addition, the transformation has several other interesting properties:

$$y = f(x) \approx \frac{\ln(4 \cdot a \cdot x)}{a}, \quad \text{when } x \text{ is very large} \quad (42)$$

$$y' = f'(x) \approx \frac{1}{c}, \quad \text{when } |x| \text{ is very small} \quad (43)$$

The transformation described in this section is applicable to any measured data in which the errors can be described by a three-term error model. In preferred embodiments, the measured data are measured in a microarray gene expression experiment. In other preferred embodiments, the measured data are measured in a protein array experiment or a 2D gel protein experiment.

5.5.2. Other Transformations

Another transformation that can be used to transform the data before applying the method described in Section 5.2. is a logarithm transformation:

$$y(k)=f(x(k))=\ln(x(k)), \text{ for } x>0 \quad (44)$$

In Equation 30, when intensity x is very high, the fractional error is the dominant error source. In this case, the standard deviation of y is approximately a constant:

$$\sigma_y(k) \approx \sigma_x(k) \cdot f'(x(k)) \approx \frac{a \cdot x(k)}{x(k)} = a, \quad \text{when } x \text{ is very large} \quad (45)$$

When intensity x is low, the standard deviation of y is inversely proportional to x, and is approaching infinity:

$$\sigma_y(k) \approx \sigma_x(k) \cdot f'(x(k)) \approx \frac{\sigma_{bkg}(k)}{x(k)}, \text{ when } x \text{ is very small} \quad (41)$$

Still another transformation that can be used to transform the data is a piecewise hybrid transformation (see, e.g., D. Holder, et al, "Quantitation of Gene Expression for High-Density Oligonucleotide Arrays: A SAFER Approach", presented in Genelogic Workshop on Low Level Analysis of Affymetrix Genechip® data, Nov. 19, 2001, Bethesda, Md., This hybrid transformation uses a linear function at the low intensity side and a logarithm function for high intensities. An arbitrary parameter c' defines the boundary between the linear and the logarithmic functions. Equation 47 is the mathematical definition of the hybrid transformation function.

$$y(k)=f(x(k))=x(k), \text{ for } 0 \leq x(k) < c'$$

$$y(k)=f(x(k))=c' \cdot \ln(x(k)/c')+c', \text{ for } x(k) \geq c' \quad (47)$$

$$y(k)=f(x(k))=0, \text{ for } x(k)<0$$

In one embodiment, parameter c' in Equation 47 is chosen to be 20. Errors of the hybrid-transformed intensities can be estimated as $$\sigma_y(k) \approx \sigma_x(k) \cdot f'(x(k)) = \sigma_x(k), \text{ for } 0 \leq x(k) < c'$$

$$\sigma_y(k) \approx \sigma_x(k) \cdot f'(x(k)) = c' \cdot \sigma_x(k)/x(k), \text{ for } x(k) \geq c' \quad (48)$$

5.6. Implementation Systems and Methods

The analytical methods of the present invention can preferably be implemented using a computer system, such as the computer system described in this section, according to the following programs and methods. Such a computer system can also preferably store and manipulate a compendium of the present invention which comprises a plurality of perturbation response profiles and which can be used by a computer system in implementing the analytical methods of this invention. Accordingly, such computer systems are also considered part of the present invention.

An exemplary computer system suitable from implementing the analytic methods of this invention is illustrated in FIG. 9. Computer system 901 is illustrated here as comprising internal components and as being linked to external components. The internal components of this computer system include a processor element 902 interconnected with a main memory 903. For example, computer system 901 can be an Intel Pentium®-based processor of 200 MHZ or greater clock rate and with 32 MB or more main memory. In a preferred embodiment, computer system 901 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 904. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 905, which is most typically a monitor and a keyboard together with a graphical input device 906 such as a "mouse." The computer system is also typically linked to a network link 907 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 9. The software components comprise both software components that are standard in the art and components that are special to the present invention. These software components are typically stored on mass storage such as the hard drive 904, but can be stored on other computer readable media as well including, for example, one or more floppy disks, one or more CD-ROMs, one or more DVDs or one or more DATs. Software component 910 represents an operating system which is responsible for managing the computer system and its network interconnections. The operating system can be, for example, of the Microsoft Windows™ family such as Windows 95, Window 98, Windows NT, Windows 2000, or Windows XP. Alternatively, the operating software can be a Macintosh operating system, a UNIX operating system or the LINUX operating system. Software components 911 comprises common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 912 comprises any analytic methods of the present invention described supra, preferably programmed in a procedural language or symbolic package. For example, software component 912 preferably includes programs that cause the processor to implement steps of accepting a plurality of measured expression profiles and storing the profiles in the memory. For example, the computer system can accept exon expression profiles that are manually entered by a user (e.g., by means of the user interface). More preferably, however, the programs cause the computer system to retrieve measured expression profiles from a database. Such a database can be stored on a mass storage (e.g., a hard drive) or other computer readable medium and loaded into the memory of the computer, or the compendium can be accessed by the computer system by means of the network 907.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

5.7. High-Throughput Screening Assays

This section describes some exemplary high-throughput screening assays, which can be used to generate measurements to which the methods and programs of the present invention can be applied.

Various types of cell-based assays are widely used in drug discovery/development and biological investigations. Cell-based assays that can be used in conjunction with the present invention include those for monitoring cell health and cell death under various conditions, e.g., for quantitation of cell viability and cell proliferation. Cell-based assays can be used in conjunction with the present invention also include those for monitoring molecular processes in cells, such as activation of particular signaling pathways, receptor binding, ion concentrations, membrane potential, specific translocations, enzyme activities, gene expression, as well as the presence, amounts and patterns of cellular molecules, e.g., metabolites, proteins, lipids, carbohydrates, and nucleic acid sequences. Cell-based assays can be used in conjunction with the present invention can be performed with either living cells or fixed-cell preparations, and either on a single cell basis or on a cell population basis.

In one embodiment, cell-based assays are carried out using a parallel assay format in which multiple samples are screened concurrently. For example, high throughput screens of a large number of different chemical compounds and/or biological agents are often carried out using arrays of wells, e.g., in standard microtiter plates with 96, 384 or 1536 wells. An exemplary assay for large scale cell-based screens of interactions between drugs and an siRNA library was disclosed in U.S. Patent Application Publication No. 2005-0181385, published on Aug. 18, 2005.

There are various types of cell proliferation or growth inhibition assays that can be used to assay cell viability. In a preferred embodiment, an MTT proliferation assay (see, e.g., van de Loosdrechet, et al., 1994, J. Immunol. Methods 174: 311-320; Ohno et al., 1991, J. Immunol. Methods 145:199-203; Ferrari et al., 1990, J. Immunol. Methods 131: 165-172; Alley et al., 1988, Cancer Res. 48: 589-601; Carmichael et al., 1987, Cancer Res. 47:936-942; Gerlier et al., 1986, J. Immunol. Methods 65:55-63; Mosmann, 1983, J. Immunological Methods 65:55-63) is used to assay the effect of one or more agents in inhibiting the growth of cells. The cells are treated with chosen concentrations of one or more candidate agents for a chosen period of time, e.g., for 4 to 72 hours. The cells are then incubated with a suitable amount of 3-(4,5-dimethylthiazol-2-yl)-2,5-diphenyltetrazolium bromide (MTT) for a chosen period of time, e.g., 1-8 hours, such that viable cells convert MTT into an intracellular deposit of insoluble formazan. After removing the excess MTT contained in the supernatant, a suitable MTT solvent, e.g., a DMSO solution, is added to dissolved the formazan. The concentration of MTT, which is proportional to the number of viable cells, is then measured by determining the optical density at e.g., 570 nm. A plurality of different concentrations of the candidate agent can be assayed to allow the determination of the concentrations of the candidate agent or agents which causes 50% inhibition.

In another preferred embodiment, an alamarBlue™ Assay for cell proliferation is used, e.g., to screen for one or more candidate agents that can be used to inhibit the growth of cells (see, e.g., Page et al., 1993, Int. J. Oncol. 3:473-476). An alamarBlue™ assay measures cellular respiration and uses it as a measure of the number of living cells. The internal environment of proliferating cells is more reduced than that of non-proliferating cells. For example, the ratios of NADPH/NADP, FADH/FAD, FMNH/FMN, and NADH/NAF increase during proliferation. AlamarBlue can be reduced by these metabolic intermediates and, therefore, can be used to monitor cell proliferation. The cell number of a treated sample as measured by alamarBlue can be expressed in percent relative to that of an untreated control sample. alamarBlue reduction can be measured by either absorption or fluorescence spectroscopy. In one embodiment, the alamarBlue reduction is determined by absorbance and calculated as percent reduced using the equation:

$$\% \text{ Reduced} = \frac{(\varepsilon_{ox}\lambda_2)(A\lambda_1) - (\varepsilon_{ox}\lambda_1)(A\lambda_2)}{(\varepsilon_{red}\lambda_1)(A'\lambda_2) - (\varepsilon_{red}\lambda_2)(A'\lambda_1)} \times 100 \quad (1)$$

where:
$\lambda_1 = 570$ nm
$\lambda_2 = 600$ nm
$(\varepsilon_{red}\lambda_1) = 155,677$ (Molar extinction coefficient of reduced alamarBlue at 570 nm)
$(\varepsilon_{red}\lambda_2) = 14,652$ (Molar extinction coefficient of reduced alamarBlue at 600 nm)
$(\varepsilon_{ox}\lambda_1) = 80,586$ (Molar extinction coefficient of oxidized alamarBlue at 570 nm)
$(\varepsilon_{ox}\lambda_2) = 117,216$ (Molar extinction coefficient of oxidized alamarBlue at 600 nm)
$(A\lambda_1) = $ Absorbance of test wells at 570 nm
$(A\lambda_2) = $ Absorbance of test wells at 600 nm
$(A'\lambda_1) = $ Absorbance of negative control wells which contain medium plus alamar Blue but to which no cells have been added at 570 nm.
$(A'\lambda_2) = $ Absorbance of negative control wells which contain medium plus alamar Blue but to which no cells have been added at 600 nm. Preferably, the % Reduced of wells containing no cell was subtracted from the % Reduced of wells containing samples to determine the % Reduced above background.

Cell cycle analysis can be carried out using standard method known in the art. In one embodiment, the supernatant from each well is combined with the cells that have been harvested by trypsinization. The mixture is then centrifuged at a suitable speed. The cells are then fixed with, e.g., ice cold 70% ethanol for a suitable period of time, e.g., ~30 minutes. Fixed cells can be washed once with PBS and resuspended, e.g., in 0.5 ml of PBS containing Propidium Iodide (10 microgram/ml) and RNase A (1 mg/ml), and incubated at a suitable temperature, e.g., 37° C., for a suitable period of time, e.g., 30 min. Flow cytometric analysis is then carried out using a flow cytometer. In one embodiment, the Sub-G1 cell population is used as a measure of cell death. For example, the cells are said to have been sensitized to an agent if the Sub-G1 population from the sample treated with the agent is larger than the Sub-G1 population of sample not treated with the agent.

High-content screens can be performed by monitoring multiple molecules and/or processes of each sample. In one embodiment, high-content screens are performed by using multiple fluorescence labels of different colors to label different cellular molecules and/or processes (Giuliano et al., 1995, Curr. Op. Cell Biol. 7:4; Giuliano et al., 1995, Ann. Rev. Biophys. Biomol. Struct. 24:405). In another embodiment, both spatial and temporal dynamics of various cellular processes are monitored (Farkas et al., 1993, Ann. Rev. Physiol. 55:785; Giuliano et al., 1990, In Optical Microscopy for Biology. B. Herman and K. Jacobson (eds.), pp. 543-557, Wiley-Liss, New York; Hahn et al., 1992, Nature 359:736; Waggoner et al., 1996, Hum. Pathol. 27:494). Single cell measurements can also be performed. Each cell can be treated as a "well" that has spatial and temporal information on the activities of the labeled constituents.

In another embodiment, cell-based assays can also be performed using cell microarrays (Ziauddin et al., Nature 411: 107-110; Bailey et al., DDT 7, No. 18 (supplement):1-6). cDNA Cell microarrays can be generated by printing cDNA-containing plasmids on a surface. siRNA Cell microarrays can be generated by printing plasmids each containing a sequence encoding an siRNA on a surface. The printed arrays are then exposed to a lipid transfection reagent to form lipid-DNA complexes on the surface. Cells are then added to the surface. Clusters of cells transfected by cDNA contained in a plasmid printed on the surface are generated at the location of the printed plasmid. Such cell microarrays can contain as high as 6,000 to 10,000 spots per slide. Each spot contains a cluster of about 100 transfected cells.

In one embodiment, the assays are used for interaction screening. For example, one or more genes in a cell of a cell type which interact with, e.g., modulate the effect of, an agent, e.g., a drug, can be screened using an siRNA cell-based assay. As used herein, interaction of a gene with an agent or another gene includes interactions of the gene and/or its products with the agent or another gene/gene product. For example, an identified gene may confer resistance or sensitivity to a drug, i.e., reduces or enhances the effect of the drug. Such gene or genes can be identified by knocking down a plurality of different genes in cells of the cell type using a plurality of small interfering RNAs (knockdown cells), each of which targets one of the plurality of different genes, and determining which gene or genes among the plurality of different genes whose knockdown modulates the response of the cell to the agent. In one embodiment, a plurality of different knockdown cells (a knockdown library) are generated, each knockdown cell in the knockdown library comprising a different gene that is knockdown, e.g., by an siRNA. In another embodiment, a plurality of different knockdown cells (a knockdown library) are generated, each knockdown cell in the knockdown library comprising 2 or more different genes that are knockdown, e.g., by shRNA and siRNA targeting different genes. In one embodiment, the knockdown library comprises a plurality of cells, each of which expresses an siRNA targeting a primary gene and is supertransfected with one or more siRNAs targeting a secondary gene. It will be apparent to one skilled in the art that a knockdown cell may also be generated by other means, e.g., by using antisense, ribozyme, antibody, or a small organic or inorganic molecule that target the gene or its product. It is envisioned that any of these other means and means utilizing siRNA can be used alone or in combination to generate a knockdown library. Any method for siRNA silencing may be used, including methods that allow tuning of the level of silencing of the target gene.

In one embodiment, the interaction screening assays use an siRNA knockdown library comprising a plurality of cells of a cell type each comprising one of a plurality of siRNAs, each of the plurality of siRNAs targeting and silencing (i.e., knocking down) one of a plurality of different genes in the cell (i.e., knockdown cells). Any known method of introducing siRNAs into a cell can be used for this purpose. Preferably, each of the plurality of cells is generated and maintained separately such that they can be studied separately. Each of the plurality of cells is then treated with an agent, and the effect of the agent on the cell is determined. The effect of the agent on a cell comprising a gene silenced by an siRNA is then compared with the effect of the agent on cells of the cell type which do not comprise an siRNA, i.e., normal cells of the cell type. Knockdown cell or cells which exhibit a change in response to the agent are identified. The gene which is silenced by the comprised siRNA in such a knockdown cell is a gene which modulates the effect of the agent. Preferably, the plurality of siRNAs comprises siRNAs targeting and silencing at least 5, 10, 100, or 1,000 different genes in the cells. In a preferred embodiment, the plurality of siRNAs targets and silences endogenous genes.

In a preferred embodiment, the knockdown library comprises a plurality of different knockdown cells having the same gene knocked down, e.g., each cell having a different siRNA targeting and silencing a same gene. The plurality of different knockdown cells having the same gene knocked down can comprises at least 2, 3, 4, 5, 6 or 10 different knockdown cells, each of which comprises an siRNA targeting a different region of the knocked down gene. In another preferred embodiment, the knockdown library comprises a plurality of different knockdown cells, e.g., at least 2, 3, 4, 5, 6, or 10, for each of a plurality of different genes represented in the knockdown library. In still another preferred embodiment, the knockdown library comprises a plurality of different knockdown cells, e.g., at least 2, 3, 4, 5, 6, or 10, for each of all different genes represented in the knockdown library.

In another preferred embodiment, the knockdown library comprises a plurality of different knockdown cells having different genes knocked down, each of the different knockdown cells has two or more different siRNA targeting and silencing a same gene. In preferred embodiment, each different knockdown cell can comprises at least 2, 3, 4, 5, 6 or 10 different siRNAs targeting the same gene at different regions.

In a preferred embodiment, the interaction of a gene with an agent is evaluated based on responses of a plurality of different knockdown cells having the gene knocked down, e.g., each cell having a different siRNA targeting and silencing a same gene. Utilizing the responses of a plurality of different siRNAs allows determination of the on-target and off-target effect of different siRNAs (see, e.g., International Publication No. WO 2005/018534, published on Mar. 3, 2005).

The effect of the agent on a cell of a cell type may be reduced in a knockdown cell as compared to that of a normal cell of the cell type, i.e., the knockdown of the gene mitigates the effect of the agent. The gene which is knocked down in such a cell is said to confer sensitivity to the agent. Thus, in one embodiment, the siRNA interaction assay is used for identifying one or more genes that confer sensitivity to an agent.

The effect of the agent on a cell of a cell type may be enhanced in a knockdown cell as compared to that of a normal cell of the cell type. The gene which is knocked down in such a cell is said to confer resistance to the agent. Thus, in another embodiment, the method of the invention is used for identifying a gene or genes that confers resistance to an agent. The enhancement of an effect of an agent may be additive or synergistic.

The assays can be used for evaluating a plurality of different agents. For example, sensitivity to a plurality of different DNA damaging agents may be evaluated. In a preferred embodiment, sensitivity of each knockdown cell in the knockdown library to each of the plurality of different agents is evaluated using a set of microtiter plates for each different agent and/or different dosage.

The assays may be used for identifying interaction between different genes by using an agent that regulates, e.g., suppresses or enhances, the expression of a gene and/or an activity of a protein encoded by the gene. Examples of such agents include but are not limited to siRNA, antisense, ribozyme, antibody, and small organic or inorganic molecules that target the gene or its product. The gene targeted by such an agent is termed the primary target. Such an agent can be used in conjunction with a knockdown library to identify gene or genes which modulates the response of the cell to the agent. The primary target can be different from any of the plurality of genes represented in the knockdown library (secondary genes). The gene or genes identified as modulating the effect of the agent are therefore gene or genes that interact with the primary target.

In a preferred embodiment, assays using a dual siRNA approach can be used for indentifying interaction between different genes. In a preferred embodiment, dual RNAi screens is achieved through the use of stable in vivo delivery of an shRNA disrupting the primary target gene and supertransfection of an siRNA targeting a secondary target gene. This approach provides matched (isogenic) cell line pairs (plus or minus the shRNA) and does not result in competition between the shRNA and siRNA. In the method, short hairpin RNAs (shRNAs) are expressed from recombinant vectors introduced either transiently or stably integrated into the genome (see, e.g., Paddison et al., 2002, *Genes Dev* 16:948-958; Sui et al., 2002, *Proc Natl Acad Sci USA* 99:5515-5520; Yu et al., 2002, *Proc Natl Acad Sci USA* 99:6047-6052; Miyagishi et al., 2002, *Nat Biotechnol* 20:497-500; Paul et al., 2002, *Nat Biotechnol* 20:505-508; Kwak et al., 2003, *J Pharmacol Sci* 93:214-217; Brummelkamp et al., 2002, *Science* 296:550-553; Boden et al., 2003, *Nucleic Acids Res* 31:5033-5038; Kawasaki et al., 2003, *Nucleic Acids Res* 31:700-707). The siRNA that disrupts the primary gene can be expressed (via an shRNA) by any suitable vector which encodes the shRNA. The vector can also encode a marker which can be used for selecting clones in which the vector or a sufficient portion thereof is integrated in the host genome such that the shRNA is expressed. Any standard method known in the art can be used to deliver the vector into the cells. In one embodiment, cells expressing the shRNA are generated by transfecting suitable cells with a plasmid containing the vector. Cells can then be selected by the appropriate marker. Clones are then picked, and tested for knockdown. In another embodiment, cell microarray comprising a plurality of cells comprising the shRNA can be used to carry out a dual siRNA assay. In a preferred embodiment, the expression of the shRNA is under the control of an inducible promoter such that the silencing of its target gene can be turned on when desired. Inducible expression of an siRNA is particularly useful for targeting essential genes.

In one embodiment, the expression of the shRNA is under the control of a regulated promoter that allows tuning of the silencing level of the target gene. This allows screening against cells in which the target gene is partially knocked out. As used herein, a "regulated promoter" refers to a promoter that can be activated when an appropriate inducing agent is present. An "inducing agent" can be any molecule that can be used to activate transcription by activating the regulated promoter. An inducing agent can be, but is not limited to, a peptide or polypeptide, a hormone, or an organic small molecule. An analogue of an inducing agent, i.e., a molecule that activates the regulated promoter as the inducing agent does, can also be used. The level of activity of the regulated promoter induced by different analogues may be different, thus allowing more flexibility in tuning the activity level of the regulated promoter. The regulated promoter in the vector can be any mammalian transcription regulation system known in the art (see, e.g., Gossen et al, 1995, Science 268:1766-1769; Lucas et al, 1992, Annu. Rev. Biochem. 61:1131; Li et al., 1996, Cell 85:319-329; Saez et al., 2000, Proc. Natl. Acad. Sci. USA 97:14512-14517; and Pollock et al., 2000, Proc. Natl. Acad. Sci. USA 97:13221-13226). In preferred embodiments, the regulated promoter is regulated in a dosage and/or analogue dependent manner. In one embodiment, the level of activity of the regulated promoter is tuned to a desired level by a method comprising adjusting the concentration of the inducing agent to which the regulated promoter is responsive.

The desired level of activity of the regulated promoter, as obtained by applying a particular concentration of the inducing agent, can be determined based on the desired silencing level of the target gene.

In one embodiment, a tetracycline regulated gene expression system is used (see, e.g., Gossen et al, 1995, Science 268:1766-1769; U.S. Pat. No. 6,004,941). A tet regulated system utilizes components of the tet repressor/operator/inducer system of prokaryotes to regulate gene expression in eukaryotic cells. Thus, the invention provides methods for using the tet regulatory system for regulating the expression of an shRNA linked to one or more tet operator sequences. The methods involve introducing into a cell a vector encoding a fusion protein that activates transcription. The fusion protein comprises a first polypeptide that binds to a tet operator sequence in the presence of tetracycline or a tetracycline analogue operatively linked to a second polypeptide that activates transcription in cells. By modulating the concentration of a tetracycline, or a tetracycline analogue, expression of the tet operator-linked shRNA is regulated.

In other embodiments, an ecdyson regulated gene expression system (see, e.g., Saez et al., 2000, Proc. Natl. Acad. Sci. USA 97:14512-14517), or an MMTV glucocorticoid response element regulated gene expression system (see, e.g., Lucas et al, 1992, Annu. Rev. Biochem. 61:1131) may be used to regulate the expression of the shRNA.

In one embodiment, a pRETRO-SUPER (pRS) vector which encodes a puromycin-resistance marker and drives shRNA expression from an H1 (RNA Pol III) promoter is used. The pRS-shRNA plasmid can be generated by any standard method known in the art. In one embodiment, the pRS-shRNA is deconvoluted from a library plasmid pool for a chosen gene by transforming bacteria with the pool and looking for clones containing only the plasmid of interest. Preferably, a 19 mer siRNA sequence is used along with suitable forward and reverse primers for sequence specific PCR. Plasmids are identified by sequence specific PCR, and confirmed by sequencing. Cells expressing the shRNA are generated by transfecting suitable cells with the pRS-shRNA plasmid. Cells are selected by the appropriate marker, e.g., puromycin, and maintained until colonies are evident. Clones are then picked, and tested for knockdown.

In another embodiment, an shRNA is expressed by a plasmid, e.g., a pRS-shRNA. The knockdown by the pRS-shRNA plasmid, can be achieved by transfecting cells using Lipofectamine 2000 (Invitrogen).

In a preferred embodiment, matched cell lines (±primary target gene) are generated by selecting stable clones containing either empty pRS vector or pRS-shRNA.

Silencing of the secondary target gene are then carried out using cells of a generated shRNA primary target clone. Silencing of the secondary target gene can be achieved using any known method of RNA interference (see, e.g., Section 5.2.). For example, secondary target gene can be silenced by transfection with siRNA and/or plasmid encoding an shRNA. In one embodiment, cells of a generated shRNA primary target clone are supertransfected with one or more siRNAs targeting a secondary target gene. In one embodiment, the one or more siRNAs targeting the secondary gene are transfected into the cells directly. In another embodiment, the one or more siRNAs targeting the secondary gene are transfected into the cells via shRNAs using one or more suitable plasmids. RNA can be harvested 24 hours post transfection and knockdown assessed by TaqMan analysis. In a preferred embodiment, an siRNA pool containing at least k (k=2, 3, 4, 5, 6 or 10) different siRNAs targeting the secondary target gene at different sequence regions is used to supertransfect the cells. In another preferred embodiment, an siRNA pool containing at least k (k=2, 3, 4, 5, 6 or 10) different siRNAs targeting two or more different secondary target genes is used to supertransfect the cells.

In a preferred embodiment, the total siRNA concentration of the pool is about the same as the concentration of a single siRNA when used individually, e.g., 100 nM. Preferably, the total concentration of the pool of siRNAs is an optimal concentration for silencing the intended target gene. An optimal concentration is a concentration further increase of which does not increase the level of silencing substantially. In one embodiment, the optimal concentration is a concentration further increase of which does not increase the level of silencing by more than 5%, 10% or 20%. In a preferred embodiment, the composition of the pool, including the number of different siRNAs in the pool and the concentration of each different siRNA, is chosen such that the pool of siRNAs causes less than 30%, 20%, 10% or 5%, 1%, 0.1% or 0.01% of silencing of any off-target genes. In another preferred embodiment, the concentration of each different siRNA in the pool of different siRNAs is about the same. In still another preferred embodiment, the respective concentrations of different siRNAs in the pool are different from each other by less than 5%, 10%, 20% or 50%. In still another preferred embodiment, at least one siRNA in the pool of different siRNAs constitutes more than 90%, 80%, 70%, 50%, or 20% of the total siRNA concentration in the pool. In still another preferred embodiment, none of the siRNAs in the pool of different siRNAs constitutes more than 90%, 80%, 70%, 50%, or 20% of the total siRNA concentration in the pool. In other embodiments, each siRNA in the pool has an concentration that is lower than the optimal concentration when used individually. In a preferred embodiment, each different siRNA in the pool has an concentration that is lower than the concentration of the siRNA that is effective to achieve at least 30%, 50%, 75%, 80%, 85%, 90% or 95% silencing when used in the absence of other siRNAs or in the absence of other siRNAs designed to silence the gene. In another preferred embodiment, each different siRNA in the pool has a concentration that causes less than 30%, 20%, 10% or 5% of silencing of the gene when used in the absence of other siRNAs or in the absence of other siRNAs designed to silence the gene. In a preferred embodiment, each siRNA has a concentration that causes less than 30%, 20%, 10% or 5% of silencing of the target gene when used alone, while the plurality of siRNAs causes at least 80% or 90% of silencing of the target gene.

In one embodiment, siRNA assays can be used for identifying one or more genes which exhibit synthetic lethal interaction with a primary target gene. In the method, an agent that is an inhibitor of the primary target gene in the cell type is used to screen against a knockdown library. The gene or genes identified as enhancing the effect of the agent are therefore gene or genes that have synthetic lethal interaction with the primary target. In a preferred embodiment, the agent is an siRNA targeting and silencing the primary target.

The method for determining the effect of an agent on cells depends on the particular effect to be evaluated. For example, if the agent is an anti-cancer drug, and the effect to be evaluated is the growth inhibitory effect of the drug, an MTT assay or an alamarBlue assay may be used (see, supra). One skilled person in the art will be able to choose a method known in the art based on the particular effect to be evaluated.

In another embodiment, siRNA assays can be used for determining the effect of an agent on the growth of cells having the primary target gene and the secondary target gene silenced. In a preferred embodiment, matched cell lines (±primary target gene) are generated as described above. Both cell lines are then supertransfected with either a control siRNA (e.g., luciferase) or one or more siRNAs targeting a secondary target gene. The cell cycle profiles are examined with or without exposure to the agent. Cell cycle analysis can be carried out using standard method known in the art. In one embodiment, the supernatant from each well is combined with the cells that have been harvested by trypsinization. The mixture is then centrifuged at a suitable speed. The cells are then fixed with ice cold 70% ethanol for a suitable period of time, e.g., ~30 minutes. Fixed cells can be washed once with PBS and resuspended, e.g., in 0.5 ml of PBS containing Propidium Iodide (10 microgram/ml) and RNase A(1 mg/ml), and incubated at a suitable temperature, e.g., 37° C., for a suitable period of time, e.g., 30 min. Flow cytometric analysis is carried out using a flow cytometer. In one embodiment, the Sub-G1 cell population is used to measure cell death. An increase of sub-G1 cell population in cells having the primary target gene and the secondary target gene silenced indicates synthetic lethality between the primary and secondary target genes in the presence of the agent.

In one embodiment, siRNA transfection was carried out as follows: one day prior to transfection, 2000 (or 100) microliters of a chosen cell line, e.g., cervical cancer HeLa cells (ATCC, Cat. No. CCL-2), grown in DMEM/10% fetal bovine serum (Invitrogen, Carlsbad, Calif.) to approximately 90% confluency were seeded in a 6-well(or 96-well) tissue culture plate at 45,000 (or 2000) cells/well. For each transfection 70 microliters of OptiMEM (Invitrogen) was mixed with 5 microliter of siRNA (Dharmacon, Lafayette, Colo.) from a 20 micromolar stock. For each transfection, a ratio of 20 microliter of OptiMEM was mixed with 5 microliter of Oligofectamine reagent (Invitrogen) and incubated 5 minutes at room temperature. Then 25-microliter OptiMEM/Oligofectamine mixture was mixed with the 75-microliter of OptiMEM/siRNA mixture, and incubated 15-20 minutes at room temperature. 100 (or 10) microliter of the transfection mixture was aliquoted into each well of the 6-well (or 96-well) plate and incubated for 4 hours at 37° C. and 5% $CO_2$.

After 4 hours, 100 microliter/well of DMEM/10% fetal bovine serum with or without DNA damage agents was added to each well to reach the final concentration of each agents as described above. The plates were incubated at 37° C. and 5% $CO_2$ for another 68 hours. Samples from the 6-well plates were analyzed for cell cycle profiles and samples from 96-well plates were analyzed for cell growth with Alamar Blue assay.

For cell cycle analysis, the supernatant from each well was combined with the cells that were harvested by trypsinization. The mixture was then centrifuged at 1200 rpm for 5 minutes. The cells were then fixed with ice cold 70% ethanol for ~30 minutes. Fixed cells were washed once with PBS and resuspended in 0.5 ml of PBS containing Propidium Iodide (10 microgram/ml) and RNase A (1 mg/ml), and incubated at 37° C. for 30 min. Flow cytometric analysis was carried out using a FACSCalibur flow cytometer (Becton Dickinson) and the data was analyzed using FlowJo software (Tree Star, Inc). The Sub-G1 cell population was used to measure cell death. If the summation of the Sub-G1 population from the (siRNA+ DMSO) sample and (Luc+drug) sample is larger than the Sub-G1 population of (siRNA+drug) sample, it is said that the siRNA silencing sensitize the cells to DNA damage.

For Alamar Blue assay, the media from the 96-well plates was removed, and 100 uL/well complete media containing 10% (vol/vol) alamarBlue reagent (BioSource International, Inc) and $1/100^{th}$ volume 1M Hepes buffer tissue culture reagent was added. The plates were then incubated 1-4 hours at 37° C. and fluorescence was measured by exciting at 544 nm and detecting emission at 590 nm with SPECTRAMax Gemini-Xs Spectrofluorometer (Molceular Devices). The fluorescence signal was corrected for background (no cells). Cell response (survival) in the presence of DNA damaging agents was measured as a percentage of control cell growth in the absence of DNA damaging agents.

6. EXAMPLES

The following examples are presented by way of illustration of the present invention, and are not intended to limit the present invention in any way.
RNAi Data RNAi data were measured from 384-well plates. Fluorescent intensities were measured from all wells. The intensity was proportional to the concentration of cells in the well. Cells in different wells were subject to treatment of a different siRNA. Some siRNA and some drug treatments reduced the cell growth or killed cells in the wells, which resulted in reduced measured intensities in those wells. Each plate had a unique layout (pattern). FIG. 1 is an example of a layout used.

In the layout shown in FIG. 1, wells in light gray were loaded with samples (cells) under study. One plate had one sample type, such as no-drug, low-dose drug-treated, or high-dose drug-treated. In each sample well, a particular siRNA was added to the sample. Other wells were blanks or controls (mock, Luciferase, PLK). Here Luc was used as the in-plate reference control in deriving the relative cell viability percentage.

Plate layout information (siRNA ID and location) and measured intensities of each plate were loaded into RESOLVER® through a MAGE file. Each experiment set was called a "screen". Each screen contained several treatment groups (such as no-drug, low-dose drug-treated, or high-dose drug-treated) of a given sample (such as Hela). Each treatment group was called a PVS. There were several plate layouts (for example 7) in each screen to cover a large number of siRNAs in the study. The same set of layouts was applied to all treatment groups in the screen. To improve the measurement confidence, two replicated plates were included in each layout in each treatment group. FIG. 2 illustrates an example of a screen. In this example of screen, there were three treatment groups, seven plate layouts, and two replicates. There were a total of forty-two 384-well plates used in this screen. Each plate provided 384 raw-intensity measurements. The plate-set format of multiple layouts was similar to Affymetrix chip-set format of multiple chips (e.g. U95A, U95B, U95C and U95D). Each plate can be viewed as a profile. To build an "experiment", multiple layouts were "stitched" together. The replicates could also be combined. In the example shown in FIG. 2, three viability ("intensity") experiments (PVS1, PVS2 and PVS3) were carried out. "Ratio" comparison experiments, such as no-drug vs. low-drug, and no-drug vs. high-drug, were then built from the experiments.

To simplify the following description of error model, the input measurement is designated as follows I_raw (i, j )—the raw fluorescent intensity measurement in the ith well of the jth plate in the plate set. In the example shown in FIG. 2, i: 1-384, and j: 1-7.

BlankSet—the i index set of wells containing Blank. In the exemplary layout shown in FIG. 1, there were 4 wells of Black.

LucSet—the i index set of wells containing Luc. In the exemplary layout in FIG. 1, there were 4 wells of Luc.

When implementing the error model in RESOLVER®, Blank and Luc can have number other than 4, and can locate in other wells different those shown in the example shown in FIG. 1.
Data Preprocessing The goal of preprocessing was to remove systematic biases. For the RNAi data, the only preprocessing used was background subtraction to remove the systematic additive-bias in each plate. The background level was estimated as the median of intensity measurements in the blanks:

$$bkg(j) = \underset{i \in BlankSet}{MEDIAN} (I\_raw(i, j)) \qquad (E1)$$

The background-subtracted intensities were:

$$I(i, j) = I\_raw(i, j) - bkg(j) \qquad (E2)$$

To avoid negative intensities, the intensity in Equation E2 was set to one if it was less than one.
Intensity Error Modeling To develop an error model, the error of the background that is subtracted from raw intensities in Equation E2 was first determined. Here the error of the background was estimated as the standard deviation of the blanks:

$$bkgstd(j) = \underset{i \in BlankSet}{STDEV} (I\_raw(i, j)) \qquad (E3)$$

A two-term error model was applied to the RNAi intensity data. The error of intensity I(i,j) was modeled as:

$$\sigma_I(i, j) = \sqrt{bkgstd(j)^2 + (FRACTION \cdot I(i,j))^2} \qquad (E4)$$

The first term on the right side of Equation E4 is the additive noise from background. The second term is the fractional, or multiplicative, noise from the fluorescent measurement.

The parameter FRACTION was tuned to 0.25 by fitting to the replicated data. This parameter was fixed when applying the error model to new data.

Logarithmic intensity was defined as $$Log\,I(i, j) = LOG_{10}(I(i, j)) \qquad (E5)$$

Error of the log intensity was estimated as $$\sigma_{LogI}(i, j) = LOG_{10}(e) \cdot \frac{\sigma_I(i, j)}{I(i, j)} \qquad (E6)$$

Estimating Percentage Viability

The relative viability of each RNAi measurement was defined as the relative percentage change of the measured RNAi intensity I(i,j) compared to the mean intensity of Luc:

$$Via(i, j) = 100 \cdot \frac{I(i, j)}{I\_Luc(j)} \qquad (E7)$$

where $$I\_Luc(j) = \underset{i \in LucSet}{MEAN} (I(i, j)) \qquad (E8)$$

Figure 3:
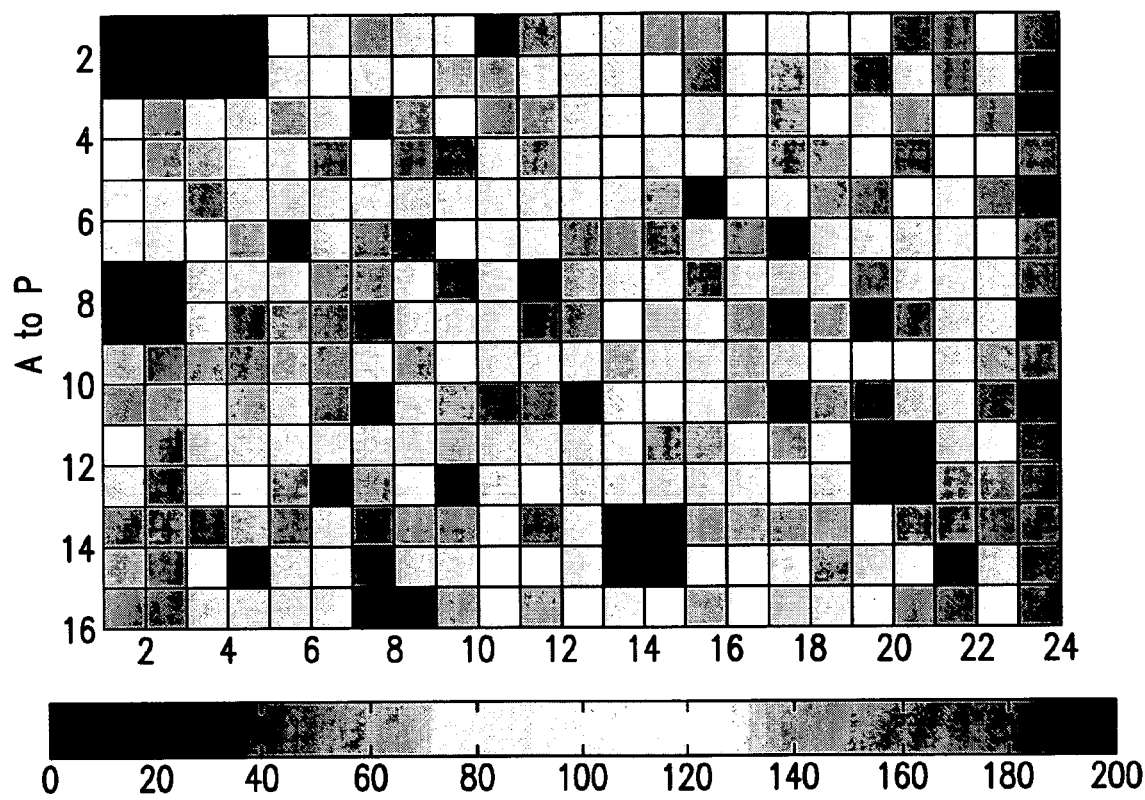
FIG. 3 shows an example of pseudo-colored viability measurements using a 384-well plate.
Figure 4:
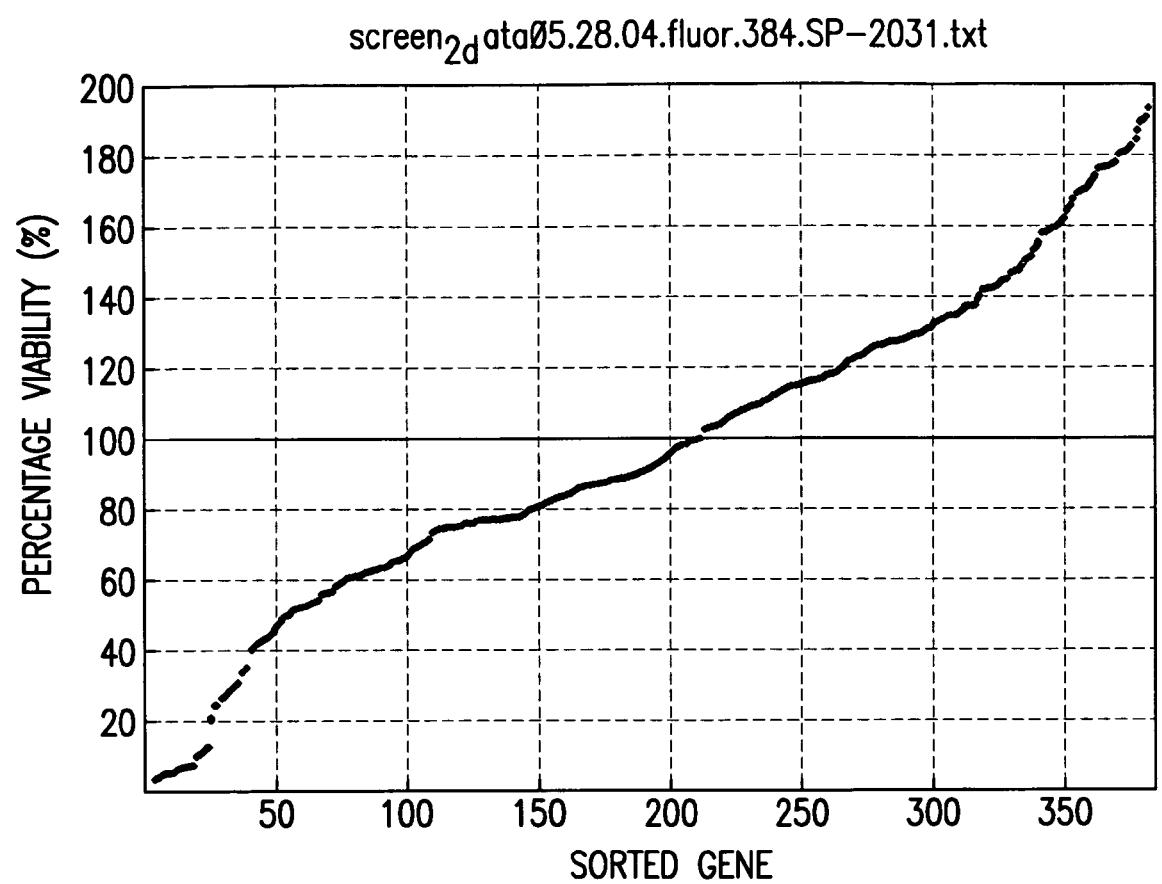
FIG. 4 shows an example of sorted viability measurements corresponding to the measurements of the plate shown in FIG. 3.

FIG. 3 shows an example of viability measurements in a plate of no-drug, which had the layout shown in FIG. 1. The viability value is pseudo-colored in the display. The light gray was near 100, which was the mean of Luc. FIG. 4 is the sorted viability measurements of this plate.

To estimate the error of the viability, the error of the Luc mean in Equation E8 was first determined. When the number of Luc wells was small, such as 4, the standard error of the mean estimated from the Luc wells may not be stable. The replicates were combined by blending the propagated error from the error model and the scattered error from the sample. Assuming there are $N_{Luc}$ of Luc wells in a plate, the scattered error was:

$$errs(j) = \underset{i \in LucSet}{STDEV}(I(i, j)) / \sqrt{N_{Luc}} \quad (E9)$$

The propagated error was $$errp(j) = \frac{\sqrt{\sum_{i \in LucSet} \sigma_I(i, j)^2}}{N_{Luc}} \quad (E10)$$

The blended error of the Luc mean was $$\sigma_{I\_Luc}(j) = \frac{errp(j) + (N_{Luc} - 1) \cdot errs(j)}{N_{Luc}} \quad (E11)$$

This Luc error is termed the "reference error". In the logarithmic domain, the Luc error in Equation E11 can be transformed to $$\sigma_{LogI\_Luc}(j) = LOG_{10}(e) \cdot \frac{\sigma_{I\_Luc}(j)}{I\_Luc(j)} \quad (E12)$$

In the log domain, the error of the ratio between intensity and the mean Luc in Equation E7 was $$\sigma_{LogRatioLuc}(i, j) = \sqrt{\sigma_{LogI}(i,j)^2 + \sigma_{LogI\_Luc}(j)^2} \quad (E13)$$

This log-ratio error was transformed back to the linear domain $$\sigma_{RatioLuc}(i, j) = \sigma_{LogRatioLuc}(i, j) \cdot \frac{I(i, j)/I\_Luc(j)}{LOG_{10}(e)} \quad (E14)$$

The error of the percentage viability in Equation E7 was $$\sigma_{Via}(i, j) = 100 \cdot \sigma_{RatioLuc}(i, j) \quad (E15)$$

Figure 5:
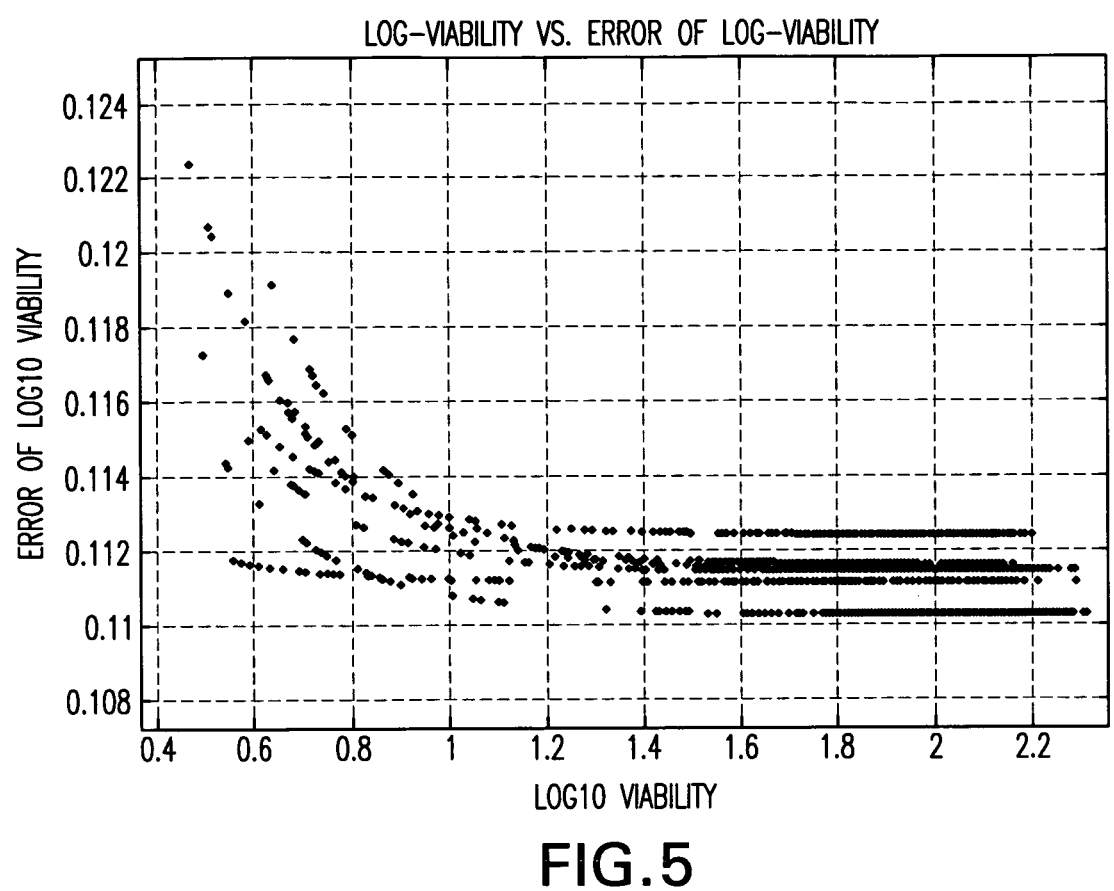
FIG. 5 shows Log-Viability versus Error of Log-Viability plots of seven different plates of different layouts in one PVS (no-drug).

FIG. 5 shows the log-viability vs. error of log-variability of seven no-drug plates of different layouts. It illustrates three main error sources in the viability measurements. The additive error dominated at the low measurement level. The multiplicative (fractional) error dominated at the high measurement level. The modeled multiplicative error had a constant CV defined by the parameter FRACTION in Equation E4. Different Luc reference errors from different plates spread the constant CV apart.

Viability Ratio Error Model for Comparative Analysis

A ratio error model was used to compare different viability measurements under different treatment conditions. To simplify the following discussion and use the same convenient terminology in two-color microarrays, the control viability is designated by g and viability error $\sigma_g$, and the perturbed viability is designated by r and error $\sigma_r$. Similar to other RESOLVER® error models developed in the past, a parameter xdev in the ratio error model was defined as:

$$xdev = \frac{r - g}{\sqrt{\sigma_r^2 + \sigma_g^2}}. \quad (E16)$$

The confidence level, e.g., the p-value, of differential viability was calculated from the parameter xdev as $$p\text{value} = 2 \cdot (1 - Erf(|xdev|)). \quad (E17)$$

The log ratio of the perturbed and control viabilities was $$lratio = \log_{10}\left(\frac{r}{g}\right). \quad (E18)$$

Error bar of the log ratio was estimated as $$\sigma_{lratio} = \left|\frac{lratio}{xdev}\right|. \quad (E19)$$

It is important to note that certain preprocessing steps, such as detrending, were not applied before the ratio error model. This was because the percentage viability measurement was a relative measurement already. The percentage viability had been normalized internally in the plate by the reference measurement of Luc.

FIG. 6 shows two examples of same-vs-same viability comparisons. One was between two replicated sets of 7 plates each in the no-drug PVS shown in FIG. 2. The other was between replicated sets of 7 plates each in the low-drug PVS shown in FIG. 2. For a given p-value threshold (<0.01), some false positive changes were detected in the same-vs-same experiments. There were a total of 2688 viability measurement comparisons between the two sets of 7 plates. Because the conservative nature of the error model, the false positive rates in these two examples were 0.002 and 0.003, respectively, which were below the p-value threshold.

FIG. 7 is an example of viability comparison between low-drug (7-gemcitabine) and no-drug without replicates. In this comparison, only one set of 7 plates was used in each condition shown in FIG. 2. Some genes showing differential viability were detected. But because there were no replicates, the sensitivity was low. FIG. 8 shows the viability comparison when two sets of replicates were used in both conditions. The same error-weighted log-ratio combining method used in RESOLVER® was applied. More signatures were detected when replicates are used. The additional information from the replicates significantly increased the sensitivity of differential viability detection.

The modeled viability error included the measurement uncertainty of the internal Luc reference. When the reference was noisy in some cases, the estimated viability error would increase, so that the risk of getting more false positives was reduced. FIG. 10 shows one example where the error model helped reduce false positives when the Luc reference was noisy.

To test how much benefit can be gained by adding more replicates in RNAi screens, the ROC (receiver operation characteristics) curve method was used to measure the difference in sensitivity and specificity when no-replicates, 2 replicates and 3 replicates are available. FIG. 11 shows the results. In this study, to identify a set of true positives, 263 affected non-control genes were selected under three replicates of high-drug treatment when comparing to three replicates of no-drug. They were detected by t-test for p-value<0.01 and absolute fold-change<1.2. The selected genes were used in independent low-drug treatment experiments to assess sensitivity. The specificity was measured in no-drug same-versus-same experiments.

The ROC curves demonstrated that there were significant improvements in the detection sensitivity and specificity when two replicates were available, but only a marginal incremental increase in sensitivity when moving from two to three replicates. For example, when the number of false positives was 10 genes, nearly 60 more genes were detected with two replicates, comparing to about total 30 genes without replicates. Adding one more replicate to a total of three, the total number of detected genes was only increased by 15 at this threshold.

Figure 12A:
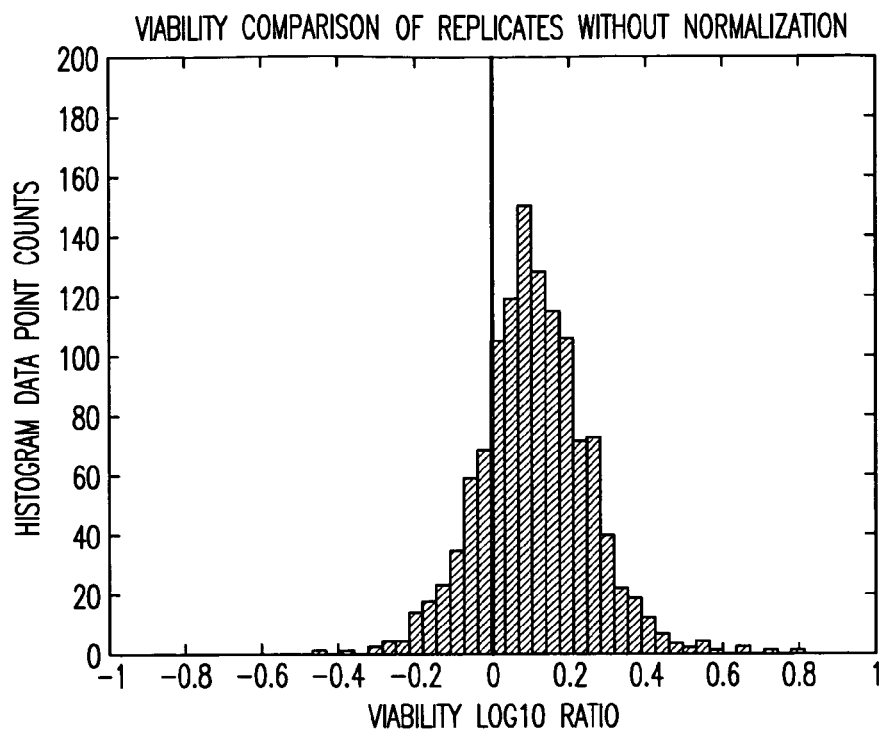
Figure 12B:
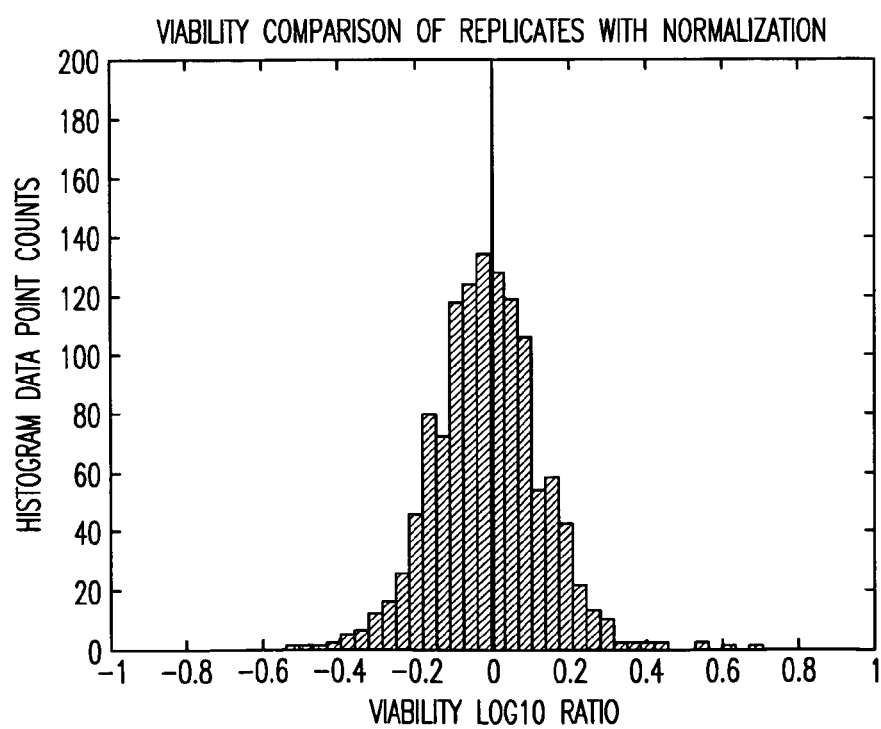
Figure 13A:
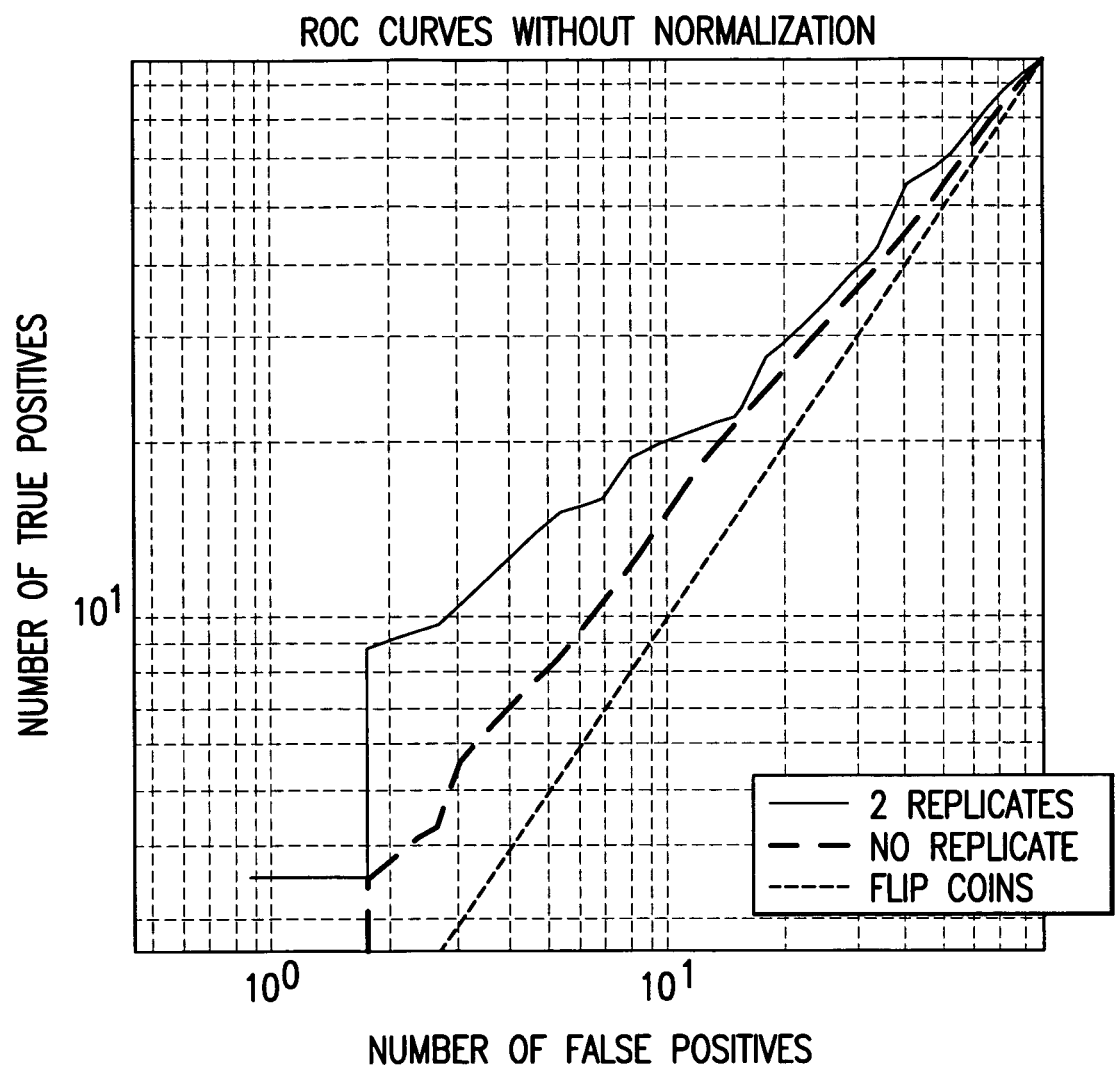
Figure 13B:
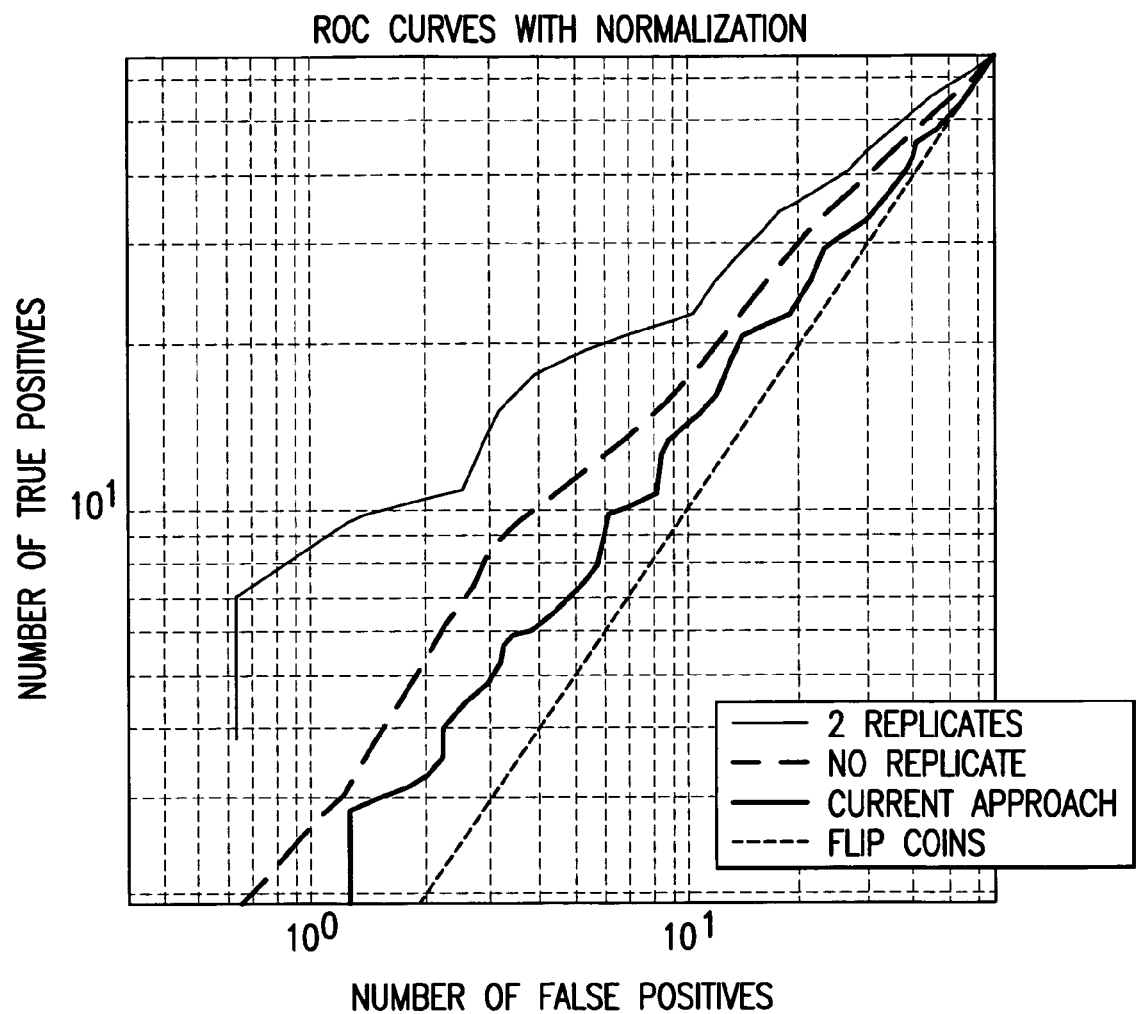

Data normalization was also used to further remove residue bias. Although using the internal Luc reference could significantly reduce plate-to-plate measurement variations, there were still residual biases in relative viability among different plates. A normalization method was used to further reduce the residual bias by balancing the average viability of all plates under the same treatment. FIGS. 12(a) and 12(b) demonstrate a significant reduction in the residual bias in the data set after applying the new normalization method. FIGS. 13(a) and 13(b) compare the ROC curves without and with the normalization. For a given specificity, the detection sensitivity was increased after the normalization was applied. The improved method provided higher detection power than the fold-change method where there are no replicates and no normalization (shown as the dashed line in FIG. 13(b)). In this comparison, the ROC curves were the results of no-replicates and two-replicates at low dose (50 ng/ml cisplatin) versus the no-drug condition. The true positive signatures were selected by t-test from an independent experiment where there were three replicates at high dose (200 ng/ml).

To summarize, this example demonstrates an error model for RNAi variability measurements. The error model contained three components, an additive error, a multiplicative error, and a reference error. The error model helped reduce false positives in viability comparisons when the number of replicates was small. With the prior information from the error model, differential viability changes below 2-fold were detected when the replicated measurements were consistent. At the same time, those average fold-changes larger than 2 but inconsistent in replicated measurements were avoided (see FIG. 8).

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of determining an effect of a perturbation on a biological variable in one or more cells of a cell type relative to one or more cells of said cell type under a reference condition, comprising
    (a) determining, using a processor,
        (i) a reference mean $\bar{y}$ of one or more reference measurements $\{y_i\}$ of said biological variable in one or more respective reference cell samples each comprising one or more cells of said cell type under said reference condition, wherein $i=1, 2, \ldots, n_r$, $n_r$ being the number of reference measurements; and
        (ii) a reference error $\sigma_y$, wherein said reference error comprises a propagated error $\sigma_p$ and a scattered error $\sigma_s$, said propagated error being determined based on predetermined experiment errors of said reference measurements, and said scattered error being determined based on deviation of each of said reference measurements with respect to said reference mean, the predetermined experiment errors being errors that can be determined without using information gained from error analysis of the one or more reference measurements;
    (b) determining, using the processor, a metric of difference between
        (iii) a measurement x of said biological variable in a cell sample comprising one or more cells of said cell type under said perturbation and
        (iv) said reference mean; and
    (c) determining, using the processor, an error of said metric using a predetermined experiment error $\sigma_x$ of said measurement x and said reference error $\sigma_y$,
wherein said metric of difference is a ratio of said measurement x and said reference mean $\bar{y}$: $x/\bar{y}$;
wherein said error of said metric is determined according to the equation $$\sigma_{ratio} = \sqrt{\sigma_{Logx}^2 + \sigma_{Logy}^2} \cdot \frac{x/\bar{y}}{\text{Log}_{10}(e)}$$

where $$\sigma_{Logx} = \text{Log}_{10}(e) \cdot \frac{\sigma_x}{x}$$

and $$\sigma_{Logy} = \text{Log}_{10}(e) \cdot \frac{\sigma_y}{y}.$$

2. The method of claim 1, wherein said propagated error is determined according to the equation $$\sigma_p = \frac{\sqrt{\sum_i \sigma_y^2(i)}}{n_r}$$

where $\sigma_y^2(i)$ is a predetermined experiment error of measurement $y_i$; wherein said scattered error is determined according to the equation $$\sigma_s = \underset{i \in 1, \ldots, n_r}{stdev(y_i)} \Big/ \sqrt{n_r}$$

and wherein said reference error is determined according to the equation $$\sigma_y = \frac{\sigma_p + (n_r - 1) \cdot \sigma_s}{n_r}.$$

3. The method of claim 2, further comprising:
prior to said step (a) a step of determining said predetermined experiment error $\sigma_y(i)$ for each said measurement $y_i$; and
prior to said step (b) a step of determining said predetermined experiment error $\sigma_x$ for said measurement x.

4. The method of claim 3, wherein background noise is present during the determining the effect of the perturbation, and wherein said predetermined experiment error $\sigma_x$ for said measurement x and said predetermined error $\sigma_y(i)$ for said measurement $y_i$ are determined according to an error model selected from the group consisting of (A) a three-term error model according to the equations $$\sigma_x = \sqrt{\sigma_{bkg}^2 + b^2 \cdot x + a^2 \cdot x^2}$$

and $$\sigma_y(i) = \sqrt{\sigma_{bkg}^2 + b^2 \cdot y_i + a^2 \cdot y_i^2}$$

wherein a is a fractional error coefficient, b is a Poisson error coefficient, and $\sigma_{bkg}$ is a standard deviation of background noise; and (B) a two-term error model according to the equations $$\sigma_x = \sqrt{\sigma_{bkg}^2 + a^2 \cdot x^2}$$

and $$\sigma_y(i) = \sqrt{\sigma_{bkg}^2 + a^2 \cdot y_i^2}$$

wherein a is a fractional error coefficient and $\sigma_{bkg}$ is a standard deviation of the background noise.

5. The method of claim 4, wherein said $\sigma_{bkg}$ is determined based on one or more measurements, different than the reference measurements, of said biological variable in a negative control sample.

6. The method of claim 1, wherein each said measurement of said biological variable is a fluorescence intensity.

7. The method of claim 1, wherein said biological variable is a survival rate of cells of said cell type as represented by the number of living cells measured after a chosen period of time after said perturbation.

8. The method of claim 1, wherein said reference condition is a condition free of said perturbation, and said ratio represents viability of cells of said cell type under said perturbation.

9. The method of claim 1, wherein said perturbation comprises subjecting cells of said cell type to one or more agents.

10. The method of claim 9, wherein said reference condition is selected from the group consisting of a mock treatment of cells of said cell type, a negative control condition, and a positive control condition.

11. The method of claim 10, wherein said one or more agents comprise an siRNA targeting a gene in a cell of said cell type.

12. A method of determining an effect of a perturbation on a biological variable in one or more cells of a cell type relative to one or more cells of said cell type under a reference condition, comprising
(a) determining, for each of one or more measurements $\{x_i\}$ of said biological variable in one or more respective cell samples each comprising one or more cells of said cell type under said perturbation, a metric of difference $D_i$ between said measurement and a reference mean $\bar{y}(i)$, wherein $i=1, 2, \ldots, n_x$, $n_x$ being the number of said one or more measurements, wherein said reference mean $\bar{y}(i)$ is a mean of one or more reference measurements $\{y_j(i)\}$ of said biological variable in one or more respective reference cell samples each comprising one or more cells of said cell type under said reference condition, wherein $j=1, 2, \ldots, n_y(i)$, $n_y(i)$ being the number of reference measurements associated with measurement $x_i$;
(b) determining, for each of said metric of difference $D_i$, an error $\sigma_D(i)$ based on
(bi) a predetermined experiment error $\sigma_x(i)$ of said measurement $x_i$ and
(bii) a reference error $\sigma_y(i)$, wherein said reference error comprises a propagated error $\sigma_{y,p}(i)$ and a scattered error $\sigma_{y,s}(i)$, said propagated error being determined based on predetermined experiment errors of said reference measurements $\{y_j(i)\}$, and said scattered error being determined based on deviations of said reference measurements $\{y_j(i)\}$ with respect to said reference mean $\bar{y}(i)$;
(c) determining, using the processor, a mean $\bar{D}$ of said metric of difference; and
(d) determining, using the processor, an error $\sigma_D$ for said mean $\bar{D}$ of said metric of difference, wherein said error $\sigma_D$ comprises a propagated error $\sigma_{D,p}$ and a scattered error $\sigma_{D,s}$, said propagated error being determined based on said $\sigma_D(i)$, and said scattered error being determined based on deviations of said metric of difference $\{D_i\}$ with respect to said mean $\bar{D}$ of said metric of difference,
wherein said metric of difference is a ratio of said measurement $x_i$ and said reference mean $\bar{y}(i)$;
wherein said error is determined according to the equation $$\sigma_{ratio} = \sqrt{\sigma_{Logx}^2 + \sigma_{Logy}^2} \cdot \frac{x/\bar{y}}{\text{Log}_{10}(e)}.$$

13. A computer system comprising
a processor, and
a memory coupled to said processor and encoding one or more programs, wherein said one or more programs cause the processor to carry out a method, comprising:
(a) determining a reference mean $\bar{y}$ of one or more reference measurements $\{y_i\}$ of a biological variable in a cell sample comprising one or more cells, wherein $i=1, 2, \ldots, n_r$, $n_r$ being the number of reference measurements; and determining a reference error $\sigma_y$, wherein said reference error comprises a propagated error $\sigma_p$ and a scattered error $\sigma_s$, said scattered error being determined based on deviation of each of said reference measurements with respect to said reference mean;
(b) determining a metric of difference between a measurement x of said biological variable in the cell sample and said reference mean; and
(c) determining an error of said metric using a predetermined experiment error $\sigma_x$ of said measurement x and said reference error $\sigma_y$,
wherein said error is determined according to an equation $$\sigma_{ratio} = \sqrt{\sigma_{Logx}^2 + \sigma_{Logy}^2} \cdot \frac{x/\bar{y}}{\text{Log}_{10}(e)}$$

where $$\sigma_{Logx} = \text{Log}_{10}(e) \cdot \frac{\sigma_x}{x}$$

and $$\sigma_{Logy} = \text{Log}_{10}(e) \cdot \frac{\sigma_y}{\bar{y}}.$$

14. A computer program product for use in conjunction with a computer having a processor and a memory connected to the processor, said computer program product comprising a non-transitory computer readable storage medium having a computer program mechanism encoded thereon, wherein said computer program mechanism may be loaded into the memory of said computer and cause said computer to carry out the method of claim 1.

15. The computer system of claim 13, wherein said propagated error is determined according to the equation $$\sigma_p = \frac{\sqrt{\sum_i \sigma_y^2(i)}}{n_r}$$

where $\sigma_y^2(i)$ is a predetermined experiment error of measurement $y_i$; wherein said scattered error is determined according to the equation $$\sigma_s = \underset{i \in 1, \ldots, n_r}{stdev}(y_i) / \sqrt{n_r}$$

and wherein said reference error is determined according to the equation $$\sigma_y = \frac{\sigma_p + (n_r - 1) \cdot \sigma_s}{n_r}.$$

16. The computer system of claim 13, further comprising:
determining said predetermined experiment error $\sigma_y(i)$ for each said measurement $y_i$; and
determining said predetermined experiment error $\sigma_x$.

17. The computer system of claim 16, wherein background noise is present during the one or more reference measurements, and wherein said predetermined experiment error $\sigma_x$ and said predetermined error $\sigma_y(i)$ are determined according to an error model selected from the group consisting of a three-term error model according to the equations $$\sigma_x = \sqrt{\sigma_{bkg}^2 + b^2 \cdot x + a^2 \cdot x^2}$$

and $$\sigma_y(i) = \sqrt{\sigma_{bkg}^2 + b^2 \cdot y_i + a^2 \cdot y_i^2}$$

wherein a is a fraction error coefficient, b is a Poisson error coefficient, and $\sigma_{bkg}$ is a standard deviation of the background noise; and a two-term error model according to the equations $$\sigma_x = \sqrt{\sigma_{bkg}^2 + a^2 \cdot x^2}$$

and $$\sigma_y(i) = \sqrt{\sigma_{bkg}^2 + a^2 \cdot y_i^2}$$

wherein a is a fractional error coefficient and $\sigma_{bkg}$ is a standard deviation of the background noise.

18. The computer system of claim 17, wherein said $\sigma_{bkg}$ is determined based on one or more measurements, different than the reference measurements, of said biological variable in a negative control sample.

19. A method of determining an effect of a perturbation on a biological variable in one or more cells of a cell type relative to one or more cells of said cell type under a reference condition, comprising
(a) determining, using a processor,
(i) a reference mean $\bar{y}$ of one or more reference measurements $\{y_i\}$ of said biological variable in one or more respective reference cell samples each comprising one or more cells of said cell type under said reference condition, wherein $i = 1, 2, \ldots, n_r$, $n_r$ being the number of reference measurements; and
(ii) a reference error $\sigma_y$, wherein said reference error comprises a propagated error $\sigma_p$ and a scattered error $\sigma_s$, said propagated error being determined based on predetermined experiment errors of said reference measurements, and said scattered error being determined based on deviation of each of said reference measurements with respect to said reference mean;
(b) determining, using the processor, a metric of difference between
(iii) a measurement x of said biological variable in a cell sample comprising one or more cells of said cell type under said perturbation and
(iv) said reference mean; and
(c) determining, using the processor, an error of said metric using a predetermined experiment error $\sigma_x$ of said measurement x and said reference error $\sigma_y$,
wherein said metric of difference is a ratio of said measurement x and said reference mean $\bar{y}$; $x/\bar{y}$
wherein said error of said metric is determined using the ratio $x/\bar{y}$.

* * * * *